United States Patent
Bate et al.

(10) Patent No.: US 9,000,262 B2
(45) Date of Patent: Apr. 7, 2015

(54) ETO1 GENES AND USE OF SAME FOR REDUCED ETHYLENE AND IMPROVED STRESS TOLERANCE IN PLANTS

(71) Applicant: Pioneer Hi Bred International Inc, Johnston, IA (US)

(72) Inventors: Nicholas J Bate, Raleigh, NC (US); Xiaoming Bao, Beijing (CN)

(73) Assignee: Pioneer Hi Bred International Inc, Johnston, IA (US)

( * ) Notice: Subject to any disclaimer, the term of this patent is extended or adjusted under 35 U.S.C. 154(b) by 0 days.

(21) Appl. No.: 14/071,206

(22) Filed: Nov. 4, 2013

(65) Prior Publication Data

US 2014/0137293 A1    May 15, 2014

Related U.S. Application Data

(63) Continuation of application No. 12/850,717, filed on Aug. 5, 2010, now abandoned.

(60) Provisional application No. 61/231,379, filed on Aug. 5, 2009.

(51) Int. Cl.
| | |
|---|---|
| *C12N 15/82* | (2006.01) |
| *C12N 15/87* | (2006.01) |
| *A01H 5/00* | (2006.01) |
| *C07K 14/415* | (2006.01) |

(52) U.S. Cl.
CPC .......... *C12N 15/8249* (2013.01); *C07K 14/415* (2013.01)

(58) Field of Classification Search
None
See application file for complete search history.

(56) References Cited

U.S. PATENT DOCUMENTS

| | | | | |
|---|---|---|---|---|
| 5,702,933 | A * | 12/1997 | Klee et al. | 800/283 |
| 2004/0031072 | A1 * | 2/2004 | La Rosa et al. | 800/278 |
| 2008/0229439 | A1 | 9/2008 | La Rosa et al. | |
| 2013/0333061 | A1 * | 12/2013 | Wu et al. | 800/260 |

FOREIGN PATENT DOCUMENTS

WO    0157063 A1    8/2001

OTHER PUBLICATIONS

Friedberg I., Automated protein function prediction—the genomic challenge, Brief. Bioinformatics (2006) 7:225-242.*
Yoshida et al, *Arabidopsis* ETO1 specifically interacts with and negatively regulates type2 I-aminocyclopropane-I-carboxylate synthases, BMC Plant Biol. (2005) 5:14 (p. 1-13).*
Wang et al, Regulation of ethylene gas biosynthesis by the *Arabidopsis* ETO1 protein, Nature (2004) 428:945-950.*
Colliver et al, Differential modification of flavonoid and isoflavonoid biosynthesis with an antisense chalcone synthase construct in transgenic Lotus corniculatus, Plant Mol. Bio. (1997) 35:509-522.*
Yoshida, et al.; "*Arabidopsis* ETOI Specifically Interacts With And Negatively Regulates Type 2 I-Aminocyclopropane-I-Carboxylate Synthases"; BMC Plant Biology (2005) 5:14.
Friedberg, I.; "Automated Protein Function Prediction—the Genomic Challenge"; Brief. Bioinfomatics (2006).
Wang, et al.; "Regulation of ethylene gas biosynthesis by the *Arabidopsis* ETO1 protein"; Nature (2004) 428(6986):945-950.
Database EMBL [Online], Accession No. AK244938, "Glycine max cDNA clone"; GMFL01-17-G21, 2008, 2 pp.

* cited by examiner

*Primary Examiner* — Cathy Kingdon Worley
*Assistant Examiner* — Mykola Kovalenko
(74) *Attorney, Agent, or Firm* — Pioneer Hi-Bred Int'l Inc.

(57) ABSTRACT

The invention provides isolated ethylene over-producer 1 (ETO1) nucleic acid molecules which are associated with ethylene production in plants and their encoded proteins. The present invention provides methods and compositions relating to altering ethylene production and abiotic stress response in plants. The invention further provides recombinant expression cassettes, host cells, transgenic plants and antibody compositions.

7 Claims, No Drawings

ETO1 GENES AND USE OF SAME FOR REDUCED ETHYLENE AND IMPROVED STRESS TOLERANCE IN PLANTS

CROSS-REFERENCE TO RELATED APPLICATIONS

This application is a continuation of U.S. patent application Ser. No. 12/850,717 filed Aug. 5, 2010 and claims the benefit of U.S. Provisional Patent Application No. 61/231,379, filed Aug. 5, 2009, both of which are hereby incorporated herein in their entirety by reference.

TECHNICAL FIELD

The present invention relates generally to plant molecular biology. More specifically, it relates to nucleic acids and methods for modulating their expression in plants.

BACKGROUND OF THE INVENTION

Plant hormones have been intensively studied for decades for their diverse and complex effects on plant life. Of the five main hormones-auxins, ethylene, abscisic acid, cytokinins and gibberellins-the molecular signaling and mode of action of ethylene has been the most fully researched.

Ethylene ($C_2H_4$) is a gaseous plant hormone that affects myriad developmental processes and fitness responses in plants, such as germination, flower and leaf senescence, fruit ripening, leaf abscission, root nodulation, programmed cell death and responsiveness to stress and pathogen attack. Over the past decade, genetic screens have identified more than a dozen genes involved in the ethylene response in plants.

Ethylene and the ethylene response pathways govern diverse processes in plants, and these effects are sometimes affected by the action of other plant hormones, other physiological signals and the environment, both biotic and abiotic. For example, it is known that cytokinin can cause ethylene like effects through the action of ethylene. In addition, abscisic acid can inhibit ethylene production and signaling. Auxin and ethylene are also known to cooperate in various physiological phenomena. Such physiological activities of ethylene include, but are not limited to, promotion of food ripening, abscission of leaves and fruit of dicotyledonous species, flower senescence, stem extension of aquatic plants, gas space (aerenchyma) development in roots, leaf epinastic curvatures, stem and shoot swelling (in association with stunting), femaleness in cucurbits, fruit growth in certain species, apical hook closure in etiolated shoots, root hair formation, flowering in the Bromeliaceae, diageotropism of etiolated shoots, and increased gene expression (e.g., of polygalacturonase, cellulase, chitinases, β1,3-glucanases, etc.). Ethylene is released naturally by ripening fruit and is also produced by most plant tissues, e.g., in response to stress (e.g., drought, crowding, disease or pathogen attack, temperature (cold or heat) stress, wounding, etc.) and in maturing and senescing organs.

Ethylene is generated from methionine by a well-defined pathway involving the conversion of S-adenosyl-L-methionine (SAM or Ado Met) to the cyclic amino acid 1-aminocyclopropane-1-carboxylic acid (ACC) which is facilitated by ACC synthase. ACC synthase is an aminotransferase which catalyzes the rate limiting step in the formation of ethylene by converting S-adenosylmethionine to ACC.

Ethylene is then produced from the oxidation of ACC through the action of ACC oxidase (also known as the ethylene forming enzyme) with hydrogen cyanide as a secondary product that is detoxified by β-cyanoalanine synthase. Finally, ethylene can be metabolized by oxidation to $CO_2$ or to ethylene oxide and ethylene glycol.

There is a continuing need for modulation of ethylene production and its response pathways in plants for manipulating plant development or stress responses. This invention relates to novel ethylene over-producer 1 (ETO1) sequences and their use in plants to inhibit ethylene production by removal of a critical component on the ethylene synthesis pathway. The invention includes novel polynucleotide sequences, expression constructs, vectors, plant cells and resultant plants. These and other features of the invention will become apparent upon review of the following materials.

SUMMARY OF THE INVENTION

This invention involves the identification and characterization of novel ETO1 genes from maize and soybean which may be introduced into plants to modulate ethylene production and improve stress tolerance in plants. ETO1 is a protein that negatively regulates ACS activity and concomitant ethylene production. ACS refers to ACC synthase, where ACC is 1-aminocyclopropane-1-carboxylic acid.

The invention comprises polynucleotides, related polypeptides and all conservatively modified variants of the maize and soybean ETO1 sequences presented herein.

The invention also includes methods to alter the genetic composition of crop plants, especially maize and soybean, so that such crops can be more tolerant to abiotic stress conditions and to modulate other ethylene mediated responses. The utility of this class of invention is then both yield enhancement and stress tolerance.

Ethylene-mediated responses include but are not limited to those involving: crowding tolerance, seed set and development, growth in compacted soils, flooding tolerance, maturation and senescence, drought tolerance and disease resistance. This invention provides methods and compositions to effect various alterations in the ethylene-mediated response in a plant that would result in improved agronomic performance, particularly under stress.

Therefore, in one aspect, the present invention relates to an isolated nucleic acid molecule comprising an isolated polynucleotide sequence encoding an ETO1 protein which will bind to the C-terminus of ACS6 and target the molecule for degradation. One embodiment of the invention is an isolated polynucleotide comprising a nucleotide sequence selected from the group consisting of: (a) the nucleotide sequence comprising SEQ ID NO: 1, 3, 5, 7 or 9; (b) the nucleotide sequence encoding an amino acid sequence comprising SEQ ID NO: 2, 4, 6, 8 or 10; (c) a polynucleotide having a specified sequence identity to a polynucleotide encoding a polypeptide of the present invention; (d) a polynucleotide which is complementary to the polynucleotide of (a) and (e) a polynucleotide comprising a specified number of contiguous nucleotides from a polynucleotide of (a) or (b). The isolated nucleic acid molecule can be DNA.

Compositions of the invention include an isolated polypeptide comprising an amino acid sequence selected from the group consisting of: (a) SEQ ID NO: 2, 4, 6, 8 or 10 and (b) the amino acid sequence comprising a specified sequence identity to SEQ ID NO: 2, 4, 6, 8 or 10, wherein said polypeptide has ETO1 activity.

In another aspect, the present invention relates to a recombinant expression cassette comprising a nucleic acid molecule as described. Additionally, the present invention relates to a vector containing the recombinant expression cassette. Further, the vector containing the recombinant expression cassette can facilitate the transcription and translation of the nucleic acid molecule in a host cell. The present invention also relates to the host cells able to express the polynucleotide of the present invention. A number of host cells could be used, such as but not limited to, microbial, mammalian, plant or insect. Preferably, the host cells are non-human host cells.

In yet another embodiment, the present invention is directed to a transgenic plant or plant cell, containing the nucleic acid molecules of the present invention. Preferred plants containing the polynucleotides of the present invention include but are not limited to maize, soybean, sunflower, sorghum, canola, wheat, alfalfa, cotton, rice, barley, tomato and millet. In another embodiment, the transgenic plant is a maize plant or plant cell. Another embodiment is the transgenic seeds from the transgenic plant.

The plants of the invention can have altered ethylene production/response as compared to a control plant. In some plants, the altered ethylene production/response is directed to a vegetative tissue, a reproductive tissue or a vegetative tissue and a reproductive tissue. Plants of the invention can have at least one of the following phenotypes including but not limited to: differences in crowding tolerance, seed set and development, growth in compacted soils, flooding tolerance, drought tolerance, maturation and senescence and disease resistance, compared to non transformed plants.

Methods for decreasing ethylene synthesis in a plant are provided by introducing to the same an ETO1 protein, thereby targeting ACS6 for degradation and removing it from the ethylene synthesis pathway. The method can comprise introducing into the plant an ETO1 polynucleotide of the invention.

In a further aspect, the present invention relates to a polynucleotide amplified from a *Zea mays* or *Glycine max* nucleic acid library using primers which selectively hybridize, under stringent hybridization conditions, to loci within polynucleotides of the present invention.

DETAILED DESCRIPTION OF THE INVENTION

Definitions

Units, prefixes and symbols may be denoted in their SI accepted form. Unless otherwise indicated, nucleic acids are written left to right in 5' to 3' orientation; amino acid sequences are written left to right in amino to carboxy orientation, respectively. Numeric ranges recited within the specification are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5th edition, 1993). The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Diagnostic Molecular Microbiology Principles and Applications, Persing, et al., Ed., American Society for Microbiology, Washington, D.C. (1993). The product of amplification is termed an amplicon.

The term "antibody" includes reference to antigen binding forms of antibodies (e.g., Faba, F (ab) 2). The term "antibody" frequently refers to a polypeptide substantially encoded by an immunoglobulin gene or immunoglobulin genes or fragments thereof which specifically bind and recognize an analyte (antigen). However, while various antibody fragments can be defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain FV, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

The term "antigen" includes reference to a substance to which an antibody can be generated and/or to which the antibody is specifically immunoreactive. The specific immunoreactive sites within the antigen are known as epitopes or antigenic determinants. These epitopes can be a linear array of monomers in a polymeric composition-such as amino acids in a protein- or consist of or comprise a more complex secondary or tertiary structure. Those of skill will recognize that all immunogens (i.e., substances capable of eliciting an immune response) are antigens; however some antigens, such as haptens, are not immunogens but may be made immunogenic by coupling to a carrier molecule. An antibody immunologically reactive with a particular antigen can be generated in vivo or by recombinant methods such as selection of libraries of recombinant antibodies in phage or similar vectors. See, e.g., Huse, et al., (1989) *Science* 246:1275-1281 and Ward, et al., (1989) *Nature* 341:544-546 and Vaughan, et al., (1996) *Nature Biotech.* 14:309-314.

As used herein, "antisense orientation" includes reference to a duplex polynucleotide sequence that is operably linked to a promoter in an orientation where the antisense strand is transcribed. The antisense strand is sufficiently complementary to an endogenous transcription product such that translation of the endogenous transcription product is often inhibited.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid.

One of ordinary skill will recognize that each codon in a nucleic acid (except AUG, which is ordinarily the only codon for methionine and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitution, deletion or addition to a nucleic acid, peptide, polypeptide or protein sequence which alters, adds or deletes a single amino acid or a small percentage of amino acids in the encoded sequence results in a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7 or 10 alterations can be made.

Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80% or 90% of the native protein for its native substrate. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). See also, Creighton (1984) Proteins W. H. Freeman and Company.

By "encoding" or "encoded", with respect to a specified nucleic acid molecule, is meant comprising the information for translation into the specified protein. A nucleic acid molecule encoding a protein may comprise intervening sequences (e.g., introns) within translated regions of the nucleic acid molecule, or may lack such intervening non-translated sequences (e.g., as in cDNA). The information by which a protein is encoded is specified by the use of codons. Typically, the amino acid sequence is encoded by the nucleic acid molecule using the "universal" genetic code. However, variants of the universal code, such as are present in some plant, animal and fungal mitochondria, the bacterium *Mycoplasma capricolumn* or the ciliate *Macronucleus*, may be used when the nucleic acid is expressed therein. When the nucleic acid is prepared or altered synthetically, advantage can be taken of known codon preferences of the intended host where the nucleic acid is to be expressed.

For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray, et al., (1989) *Nucl. Acids Res.* 17:477-498). Thus, the maize preferred codon for a particular amino acid may be derived from known gene sequences from maize. Maize codon usage for 28 genes from maize plants is listed in Table 4 of Murray, et al., supra.

As used herein "full-length sequence" in reference to a specified polynucleotide or its encoded protein means having the entire amino acid sequence of, a native (nonsynthetic), endogenous, biologically active form of the specified protein. Methods to determine whether a sequence is full-length are well known in the art including such exemplary techniques as northern or western blots, primer extension, S 1 protection, and ribonuclease protection. See, e.g., Plant Molecular Biology: A Laboratory Manual, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNNAUGG, where the AUG codon therein represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the vector. Host cells may be prokaryotic cells such as *E. coli* or eukaryotic cells such as yeast, insect, amphibian or mammalian cells. Preferably, host cells are monocotyledonous or dicotyledonous plant cells. A particularly preferred monocotyledonous host cell is a maize host cell.

The term "hybridization complex" includes reference to a duplex nucleic acid structure formed by two single-stranded nucleic acid sequences selectively hybridized with each other.

By "immunologically reactive conditions" or "immunoreactive conditions" is meant conditions which allow an antibody, reactive to a particular epitope, to bind to that epitope to a detectably greater degree (e.g., at least 2-fold over background) than the antibody binds to substantially any other epitopes in a reaction mixture comprising the particular epitope. Immunologically reactive conditions are dependent upon the format of the antibody binding reaction and typically are those utilized in immunoassay protocols. See Harlow and Lane, Antibodies, A Laboratory Manual, Cold Spring Harbor Publications, New York (1988), for a description of immunoassay formats and conditions.

The term "introduced" in the context of inserting a nucleic acid molecule into a cell, means "transfection" or "transformation" or "transduction" and includes reference to the incorporation of a nucleic acid molecule into a eukaryotic or prokaryotic cell where the nucleic acid molecule may be incorporated into the genome of the cell (e.g., chromosome, plasmid, plastid or mitochondrial DNA), converted into an autonomous replicon or transiently expressed (e.g., transfected mRNA).

The term "isolated" refers to material, such as a nucleic acid molecule or a protein, which is: (1) substantially or essentially free from components that normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material can be performed on the material within or removed from its natural state. For example, a naturally occurring nucleic acid molecule becomes an isolated nucleic acid molecule if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid molecule (e.g., a promoter) becomes isolated if it is introduced by nonmaturally occurring means to a locus of the genome not native to that nucleic acid molecule. Nucleic acid molecules which are "isolated" as defined herein are also referred to as "heterologous" nucleic acid molecules.

Unless otherwise stated, the term "ETO1 nucleic acid" (also referred to herein as "ETO1 nucleic acid molecule") is a nucleic acid (also referred to herein as a "nucleic acid molecule") of the present invention and means a nucleic acid comprising a polynucleotide of the present invention (an "ETO1 polynucleotide") encoding an ETO1 polypeptide with ETO1 activity. An "ETO1 gene" is a gene of the present invention and refers to a heterologous genomic form of a full-length ETO1 polynucleotide.

A "subject plant or plant cell" is one in which genetic alteration, such as transformation, has been affected as to a gene of interest or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes of that pair to be followed. A genotype may be defined by use of one or a plurality of markers.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, Guide to Molecular Cloning Techniques, Methods in Enzymology, Vol. 152, Academic Press, Inc., San Diego, Calif. (Berger); Sambrook, et al., Molecular Cloning-A Laboratory Manual, 2nd ed., Vol. 1-3 (1989); and Current Protocols in Molecular Biology, Ausubel, et al., Eds., Current Protocols, a joint venture between Greene Publishing Associates, Inc. and John Wiley & Sons, Inc. (1994).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and where necessary to join two protein coding regions, contiguous and in the same reading frame.

As used herein, the term "plant" includes reference to whole plants, plant organs (e.g., leaves, stems, roots, etc.), seeds and progeny of same. Plant cell, as used herein includes, without limitation, a cell derived from a seed, suspension culture, embryo, meristematic region, callus tissue, leaf, root, shoot, gametophyte, sporophyte, pollen or microspore. The class of plants which can be used in the methods of the invention is generally as broad as the class of higher plants amenable to transformation techniques, including both monocotyledonous and dicotyledonous plants. A particularly preferred plant is *Zea mays*.

As used herein, "polynucleotide" includes reference to a deoxyribopolynucleotide, ribopolynucleotide or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art.

The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not always entirely linear. For instance, polypeptides may be branched as a result of ubiquitization, and they may be circular, with or without branching, generally as a result of post translation events, including natural processing event and events brought about by human manipulation which do not occur naturally. Circular, branched and branched circular polypeptides may be synthesized by non-translation natural process and by entirely synthetic methods, as well. Further, this invention contemplates the use of both the methionine-containing and the methionine-less amino terminal variants of the protein of the invention.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether or not its origin is a plant cell. Exemplary plant promoters include, but are not limited to, those that are obtained from plants, plant viruses, and bacteria which comprise genes expressed in plant cells such as *Agrobacterium* or *Rhizobium*. Examples of promoters under developmental control include promoters that preferentially initiate transcription in certain tissues, such as leaves, roots, or seeds. Such promoters are referred to as "tissue preferred". Promoters which initiate transcription only in certain tissue are referred to as "tissue specific". A "cell type" preferred promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions or the presence of light. Tissue specific, tissue preferred, cell type preferred, and inducible promoters are members of the class of "non-constitutive" promoters. A "constitutive" promoter is a promoter which is active under most environmental conditions and/or in most tissues of a plant and/or at most developmental stages.

The term "ETO1 polypeptide" refers to a polypeptide of the present invention which has ETO1 activity and refers to one or more amino acid sequences, in glycosylated or non-glycosylated form. The term is also inclusive of fragments, variants, homologs, alleles or precursors (e.g., preproproteins or proproteins) thereof which retain activity. An "ETO1 protein" is a protein of the present invention and comprises an ETO1 polypeptide. "ETO1 activity" means that the polypeptide is capable of binding to the C-terminus of ACS Class II enzymes and ushering them to the 26S proteasome for degradation resulting in a decrease in ethylene production as measurable by any of a number of available protocols.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all, as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus or nucleic acid fragment. Typically, the recombinant expression cassette portion of an expression vector includes, among other sequences, a nucleic acid to be transcribed and a promoter.

As used herein, a chimeric gene comprises a coding sequence operably linked to a transcription initiation region that is heterologous to the coding sequence.

The terms "residue" and "amino acid residue" and "amino acid" are used interchangeably herein to refer to an amino acid that is incorporated into a protein, polypeptide, or peptide (collectively "protein"). The amino acid may be a naturally occurring amino acid and unless otherwise limited, may encompass non-natural analogs of natural amino acids that can function in a similar manner as naturally occurring amino acids.

The term "selectively hybridizes" includes reference to hybridization, under stringent hybridization conditions, of a nucleic acid sequence to as other biologics. Thus, under designated immunoassay conditions, the specified antibodies bind to an analyte having the recognized epitope to a substantially greater degree (e.g., at least 2-fold over background) than to substantially all analytes lacking the epitope which are present in the sample. Specific binding to an antibody under such conditions may require an antibody that is selected for its specificity for a particular protein. For example, antibodies raised to the polypeptides of the present invention can be selected from to obtain antibodies specifically reactive with polypeptides of the present invention. The proteins used as immunogens can be in native conformation or denatured so as to provide a linear epitope.

A variety of immunoassay formats may be used to select antibodies specifically reactive with a particular protein (or other analyte). For example, solid-phase ELISA immunoassays are routinely used to select monoclonal antibodies specifically immunoreactive with a protein. See, Harlow and Lane, Antibodies, A Laboratory Manual, Cold Spring Harbor Publications, New York (1988), for a description of immunoassay formats and conditions that can be used to determine selective reactivity.

The term "stringent conditions" or "stringent hybridization conditions" includes reference to conditions under which a probe will hybridize to its target sequence, to a detectably greater degree than to other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 MNaCl, 1% SDS (sodium dodecyl sulphate) at 37° C. and a wash in 1× to 2×SSC (20×SSC=3.0 MNaCl/0.3 M trisodium citrate) at 50 to 55° C. Exemplary moderate stringency conditions include hybridization in 40 to 45% formamide, 1 MNaCl, 1% SDS at 37° C., and a wash in <RTI 0.5× to 1×SSC at 55 to 60° C. Exemplary high stringency conditions include hybridization in 50% formamide, 1 MNaCl, 1% SDS at 37° C. and a wash in 0.1×SSC at 60 to 65° C. Specificity is typically the function of post-hybridization washes, the critical factors being the ionic strength and temperature of the final wash solution. For DNA/DNA hybrids, the Tm can be approximated from the equation of Meinkoth and Wahl, (1984) *Anal. Biochem.*, 138:267-284:$T_m=81.5°$ C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with >90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3 or 4° C. lower than the thermal melting point (Tm); moderately stringent conditions can utilize a hybridization and/or wash at 6, 7, 8, 9 or 10° C. lower than the thermal melting point (Tm); low stringency conditions can utilize a hybridization and/or wash at 11, 12, 13, 14, 15 or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridization of nucleic acids is found in Tijssen, Laboratory Techniques in Biochemistry and Molecular Biology-Hybridization with Nucleic Acid Probes, Part I, Chapter 2 "Overview of principles of hybridization and the strategy of nucleic acid probe assays", Elsevier, New York (1993); and Current Protocols in Molecular Biology, Chapter 2, Ausubel, et al., Eds., Greene Publishing and Wiley-Interscience, New York (1995).

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non recombinant viral infection, non-recombinant bacterial transformation, non-recombinant transposition or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between a polynucleotide/polypeptide of the present invention with a reference polynucleotide/polypeptide: (a) "reference sequence", (b) "comparison window", (c) "sequence identity" and (d) "percentage of sequence identity".

(a) As used herein, "reference sequence" is a defined sequence used as a basis for sequence comparison with a polynucleotide/polypeptide of the present invention. A reference sequence may be a subset or the entirety of a specified sequence; for example, as a segment of a full-length cDNA or gene sequence or the complete cDNA or gene sequence.

(b) As used herein, "comparison window" includes reference to a contiguous and specified segment of a polynucleotide/polypeptide sequence, wherein the polynucleotide/polypeptide sequence may be compared to a reference sequence and wherein the portion of the polynucleotide/polypeptide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides/amino acids residues in length and optionally can be 30, 40, 50, 100 or longer. Those of skill in the art understand that to avoid a high similarity to a reference sequence due to inclusion of gaps in the polynucleotide/polypeptide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, (1981) *Adv. Appl. Math.* 2:482; by the homology alignment algorithm of Needleman and Wunsch, (1970) *J. Mol. Biol.* 48:443; by the search for similarity method of Pearson and Lipman, (1988) *Proc. Natl. Acad. Sci.* 85:2444; by computerized implementations of these algorithms, including, but not limited to: CLUSTAL in the PC/Gene program by Intelligenetics, Mountain View, Calif.; GAP, BESTFIT, BLAST, FASTA and TFASTA in the GCG Wisconsin Genetics Software Package, Version 10 (available from Accelrys Inc., 9685 Scranton Road, San Diego, Calif., USA). The CLUSTAL program is well described by Higgins and Sharp, (1988) *Gene* 73:237-244; Higgins and Sharp, (1989) *CABIOS* 5:151-153; Corpet, et al., (1988) *Nucleic Acids Research* 16:10881-90; Huang, et al., (1992) *Computer Applications in the Biosciences* 8:155-65 and Pearson, et al., (1994) *Methods in Molecular Biology* 24:307-331.

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences and TBLASTX for nucleotide query sequences against nucleotide database sequences. See, Current Protocols in Molecular Biology, Chapter 19, Ausubel, et al., Eds., Greene Publishing and Wiley-Interscience, New York (1995); Altschul et al., (1990) *J. Mol. Biol.,* 215:403-410 and Altschul, et al., (1997) *Nucleic Acids Res.* 25:3389-3402.

Software for performing BLAST analyses is publicly available, e.g., through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score.

Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10 and the BLOSUM62 scoring matrix (see, Henikoff and Henikoff, (1989) *Proc. Natl. Acad. Sci. USA* 89:10915).

In addition to calculating percent sequence identity, the BLAST algorithm also performs a statistical analysis of the similarity between two sequences (see, e.g., Karlin and Altschul, (1993) *Proc. Nat'l. Acad. Sci. USA* 90:5873-5877). One measure of similarity provided by the BLAST algorithm is the smallest sum probability (P(N)), which provides an indication of the probability by which a match between two nucleotide or amino acid sequences would occur by chance. BLAST searches assume that proteins can be modeled as random sequences. However, many real proteins comprise regions of nonrandom sequences which may be homopolymeric tracts, short-period repeats or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) *Comput. Chem.,* 17:149-163) and XNU (Clayerie and States, (1993) *Comput. Chem.,* 17:191-201) low-complexity filters can be employed alone or in combination.

Unless otherwise stated, nucleotide and protein identity/similarity values provided herein are calculated using GAP (GCG Version 10) under default values. GAP (Global Alignment Program) can also be used to compare a polynucleotide or polypeptide of the present invention with a reference sequence. GAP uses the algorithm of Needleman and Wunsch (*J. Mol. Biol.* 48:443-453 (1970)) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 100. Thus, for example, the gap creation and gap extension penalties can each independently be: 3, 4, 5, 6, 7, 8, 9, 10, 15, 20, 30, 40, 50, 60 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, Henikoff and Henikoff (1989) *Proc. Natl. Acad. Sci. USA* 89:10915).

Multiple alignment of the sequences can be performed using the CLUSTAL method of alignment (Higgins and Sharp, (1989) *CABIOS* 5:151-153) with the default parameters (GAPPENALTY=10, GAP LENGTH PENALTY=10). Default parameters for pairwise alignments using the CLUSTAL method are KTUPLE 1, GAP PENALTY=3, WINDOW=5 and DIAGONALS SAVED=5.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) *Computer Applic. Biol. Sci.,* 4:11-17, e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Overview

The present invention provides, among other things, compositions and methods for modulating (i.e., increasing or decreasing) the level of polynucleotides and polypeptides of the present invention in plants. In particular, the polynucleotides and polypeptides of the present invention can be expressed temporally or spatially, e.g., at developmental stages, in tissues, and/or in quantities, which are uncharacteristic of non-recombinantly engineered plants. Thus, the present invention provides utility in such exemplary applications as provided below.

Applicants have isolated a novel ETO1 protein that may be used in the modulation of ethylene activity and production in plants. The novel protein, its nucleotide sequences encoding the same and resultant constructs, vectors and modified plant cells, tissues, seeds and organs form the basis of the invention. The enzyme thus finds utility in a number of stress response applications such as the following.

Crowding Tolerance

The agronomic performance of crop plants is often a function of how well they tolerate planting density. Overcrowded plants grow poorly. The stress of overcrowding can be due to simple limitations of nutrients, water and sunlight. Crowding stress may also be due to enhanced contact between plants. Plants often respond to physical contact by slowing growth and thickening their tissues.

Ethylene has been implicated in plant crowding response. For example, ethylene insensitive tobacco plants did not slow growth when contacting neighboring plants (Knoester, et al., (1998) *PNAS USA* 95:1933-1937). There is also evidence that ethylene, and the plant's response to it is involved in water deficit stress and that ethylene may be causing changes in the plant that limit its growth and aggravate the symptoms of drought stress beyond the loss of water itself.

The present invention provides for decreasing ethylene production in a plant, in particular cereals such as maize, by providing one or more novel ETO1 polynucleotides or their protein products to promote tolerance of close spacing with reduced stress and yield loss.

Seed Set and Development in Maize

Ethylene plays a number of roles in seed development. For example, in maize ethylene is linked to programmed cell death of developing endosperm cells (Young, et al., (1997) *Plant Physiol.*, 115:737-751). In addition, ethylene is linked to kernel abortion, such as occurs at the tips of ears, especially in plants grown under stressful conditions (Cheng and Lur, (1996) *Physiol. Plant* 98:245-252). Reduced kernel seed set is of course a contributor to reduced yields. Consequently, the present invention provides plants, in particular maize plants, that have reduced ethylene action by providing for and/or modulating the expression/activity of the novel ETO1 polynucleotides of the invention.

Growth in Compacted Soils

Plant growth is affected by the density and compaction of soils. Denser, more compacted soils typically result in poorer plant growth. The trend in agriculture towards more minimal till planting and cultivation practices, with the goal of soil and energy conservation, is increasing the need for crop plants that can perform well under these conditions.

Ethylene is well-known to affect plant growth and development and one effect of ethylene is to promote tissue thickening and growth retardation when encountering mechanical stress, such as compacted soils. This can affect both the roots and shoots. This effect is presumably adaptive in some circumstances in that it results in stronger, more compact tissues that can force their way through or around, obstacles such as compacted soils. However, in such conditions, the production of ethylene and the activation of the ethylene pathway may exceed what is needed for adaptive accommodation to the mechanical stress of the compacted soils. And, of course, any resulting unnecessary growth inhibition would be an undesired agronomic result.

The present invention provides for decreasing ethylene production in a plant, in particular cereals such as maize, by providing for and/or modulating the expression/activity of one or more novel ETO1 polynucleotides or their protein products. Such modulated plants grow and germinate better in compacted soils, resulting in higher stand counts, the herald of higher yields.

Flooding Tolerance

Flooding and water-logged soils cause substantial losses in crop yield each year around the world. Flooding can be both widespread or local, transitory or prolonged. Ethylene has been implicated in flooding mediated damage. In fact, in flooded conditions ethylene production can rise. There are two main reasons for this rise: 1) under such flooded conditions, which creates hypoxia, plants produce more ethylene and 2) under flooded conditions the diffusion of ethylene away from the plant is slowed, because ethylene is minimally soluble in water, resulting in a rise of intra-plant ethylene levels.

Ethylene in flooded maize roots can also inhibit gravitropism, which is normally adaptive during germination in that it orients the roots down and the shoots up. Gravitropism is a factor in determining root architecture, which in turn plays an important role in soil resource acquisition. Manipulation of ethylene levels could be used to impact root angle for drought tolerance, flood tolerance, greater standability and/or improved nutrient uptake. For example, a root growing at a more erect angle (steeper) would likely grow more deeply in soil and thus obtain water at greater depths, improving drought tolerance. In the absence of drought stress a converse argument could be made for more efficient root uptake of nutrients and water in the upper layers of the soil profile, by roots which are more parallel to the soil surface. In general, roots that have a angle nearer that of vertical (steep) are also more susceptible to root lodging than roots with a shallow angle (parallel to the surface) that can be more root lodging resistant.

In addition to inhibition of gravitropism, it is likely that ethylene evolution in flooded conditions inhibits growth, especially of roots. Such inhibition will likely contribute to poor plant growth overall, and consequently is a disadvantageous agronomic trait.

The present invention provides for decreasing ethylene production in a plant, in particular cereals such as maize, by providing for and/or modulating the expression/activity of one or more novel ETO1 polynucleotides or their protein products. Such plants should grow and germinate better in flooded conditions or water-logged soils, resulting in higher stand counts.

Plant Maturation and Senescence

Ethylene is known to be involved in controlling senescence, fruit ripening and abscission. The role of ethylene in fruit ripening is well-established and industrially applied. The prediction based on precedent would be that ethylene underproduction/insensitivity would result in slower seed ripening and the converse would result in more rapid seed ripening. Abscission is primarily studied for dicot plants and apparently has little application to monocots such as cereals. Ethylene mediated senescence also is mostly studied in dicots, but control of senescence is agronomically important for both dicot and monocot crop species. Ethylene insensitivity can cause a delay of, but not arrest, senescence. The senescence process mediated by ethylene bears some similarities to the cell death process in disease symptoms and in abscission zones.

Controlling ethylene production, as through the control of one or more novel ETO1 genes, could result in modulation of maturity rates for crop plants such as maize.

The present invention provides for decreasing ethylene production in a plant, in particular cereals such as maize, by providing for and/or modulating the expression/activity of one or more novel ETO1 polynucleotides or their protein products which may contribute to a later maturing plant, which is desirable for placing crop varieties in different maturity zones.

Tolerance to Other Abiotic Stresses

Many stresses on plants induce the production of ethylene (see, Morgan and Drew, (1997) *Physiol. Plant* 100:620-630). These stresses can be cold, heat, wounding, pollution, drought and hypersalinity. Mechanical impedance (soil compaction) and flooding stresses were addressed above. It appears that several of these stresses operate through common mechanisms, such as water deficit. Clearly drought causes water deficit; crowding stress may also cause water deficit. Additionally, in maize chilling can cause an elevation in ethylene production and activity, and this induction is apparently due to chilling causing water deficit in cells (Janowaik and Dorffling, (1995) *J. Plant Physiol.* 147:257-262).

Some of the ethylene production following stresses may serve an adaptive purpose by regulating ethylene-mediated processes in the plant that result in a plant reorganized in such manner to better acclimate to the stress encountered. However, there is also evidence that ethylene production during stress can result in an aggravation of negative symptoms resulting from the stress, such as yellowing, tissue death and senescence.

To the extent that ethylene production during stress causes or augments negative stress-related symptoms, it would be desirable to create a crop plant with reduced ethylene production. Towards that end, the present invention provides for decreasing ethylene production in a plant, in particular cereals such as maize, by providing for and/or modulating the expression/activity of one or more novel ETO1 polynucleotides or their protein products to create plants that avoid certain ethylene-mediated effects.

Disease Resistance

Crop plants can be susceptible to a wide variety of pathogens, whether viruses, bacteria, fungi or insects. This susceptibility results in large crop yield losses annually worldwide. Crop breeders have endeavored to breed more resistant or tolerant varieties which can withstand pathogen attack. Additional genetic engineering strategies seek the same end. In many plant-pathogen interactions the symptoms of disease, most often tissue necrosis and resulting poor plant growth, are known to be the result of an active plant defense response to the pathogen. That is, the symptoms are caused directly by the plant and not simply by the pathogen. From among the list of all crop plants and their potential list of pathogens, resistance is the rule, and susceptibility the exception. Susceptible interactions are often thought to result from an improper or insufficient activation defense by the plant that results in a runaway symptom development and an inability to contain the pathogen.

Ethylene has long been known to be associated with plant pathogen defense systems. Many pathogenesis related genes are induced in expression at the level of mRNA by ethylene. The trend in our understanding of the role of ethylene in plant pathogen defense is towards ethylene and ethylene mediated effects being viewed as principally part of the downstream reactions to pathogen attack, as in symptom development. Ethylene seems to be involved in the plant's response to the stress of pathogen attack and in tissue damage inflicted by the pathogen. In a susceptible interaction ethylene may actually promote tissue damage. Consequently, in such situations, blocking ethylene production or action may actually result in less tissue damage, that is, more apparent resistance, even though the pathogen is compatible with the plant. Blocking ethylene action is known to result in either more susceptibility (e.g., Knoester, et al., (1988)) or more resistance (e.g., Lund, et al., (1998) *Plant Cell* 10:371-382), which indicates that the role of ethylene action is complex, as is to be expected, for it depends upon the interactions of diverse plants and pathogens.

The present invention provides for the use of one or more novel ETO1 polynucleotides or their protein products to affect enhanced resistance to plant stresses, in particular for monocots such as maize.

For most applications this will involve the reduction in ethylene production by providing for and/or modulating the expression/activity of novel ETO1 polynucleotides or their proteins, with the goal of causing plants that produce less ethylene in response to stress and thereby plants that are less prone to tissue damage following exposure to abiotic stressors. ETO1 is a potent negative regulator of ACS and ethylene production, see, for example, Chae and Faure, et al., (2003) *Plant Cell* 15(2):545-559; Christians, et al., (2009) *The Plant Journal* 57(2):332-345; Wang, et al., (2004) *Nature* 428(6986):945-950; Yoshida, et al., (2005) *BMC Plant Biology* 5:14 and Yoshida, et al., (2006) *Plant Molecular Biology* 62(3):427-437.

Plant Transformation

The generation of transgenic plants is central to crop plant genetic engineering strategies. Transgenesis typically involves the introduction of exogenous DNA into the plants cells via a variety of methods, such as particle bombardment or *Agrobacterium* infection, which is usually followed by tissue culture and plant regeneration. Transgenic plant production remains a costly and rate limiting step in genetic engineering, especially for many of the most economically important crop plants, such as the cereals, like maize.

Improving the Efficiency of this Process is Therefore of Great Importance.

It has been accepted for a long time that ethylene action has negative consequences for plant transformation. As a result various approaches to bind, trap or otherwise block the accumulation of ethylene are employed in transformation and tissue culture (see, Songstad, et al., (1991) *Plant Cell Reports* 9:694-702). The particle bombardment method causes substantial tissue/cell damage and such damage is known to elicit ethylene accumulation. Moreover, in most tissue culture methods, some tissue grows better than others, as is designed in chemical selection of transformants. Such dying tissue can emit ethylene and cause inhibition of positive transformants. Aggravating these effects is the confinement of plant tissues in containers for the purpose of tissue regeneration that can result in the accumulation of ethylene, also causing growth retardation. As ethylene is known to promote slower tissue growth and even cell/tissue death, having a means to block or minimize ethylene action during transformation is desired.

Consequently, the present invention also provides for use of the ETO1 sequences herein to create transient or stable reductions in ethylene action by increasing the expression/activity of ETO1 polynucleotides or polypeptides.

Other Utilities

The present invention also provides isolated nucleic acids comprising polynucleotides of sufficient length and complementarity to a gene of the present invention to use as probes or amplification primers in the detection, quantitation or isolation of gene transcripts. For example, isolated nucleic acids of the present invention can be used as probes in detecting deficiencies in the level of mRNA in screenings for desired transgenic plants, for detecting mutations in the gene (e.g., substitutions, deletions or additions), for monitoring upregulation of expression or changes in enzyme activity in screening assays of compounds, for detection of any number of allelic variants (polymorphisms), orthologs or paralogs of the gene, or for site directed mutagenesis in eukaryotic cells (see, e.g., U.S. Pat. No. 5,565,350). The isolated nucleic acids of the present invention can also be used for recombinant expression of their encoded polypeptides, or for use as immunogens in the preparation and/or screening of antibodies. The isolated nucleic acids of the present invention can also be employed for use in sense or antisense suppression of one or more genes of the present invention in a host cell, tissue or plant. Attachment of chemical agents which bind, intercalate, cleave and/or cross-link to the isolated nucleic acids of the present invention can also be used to modulate transcription or translation.

The present invention also provides isolated proteins comprising a polypeptide of the present invention (e.g., preproenzyme, proenzyme or enzymes). The present invention also provides proteins comprising at least one epitope from a polypeptide of the present invention. The proteins of the present invention can be employed in assays for enzyme agonists or antagonists of enzyme function, or for use as immunogens or antigens to obtain antibodies specifically immunoreactive with a protein of the present invention. Such antibodies can be used in assays for expression levels, for identifying and/or isolating nucleic acids of the present invention from expression libraries, for identification of homologous polypeptides from other species or for purification of polypeptides of the present invention.

The isolated nucleic acids and polypeptides of the present invention can be used over a broad range of plant types, particularly monocots such as the species of the family Gramineae including *Hordeum, Secale, Tritium, Sorghum* (e.g., *S. bicolor*) and *Zea* (e.g., *Z. mays*). The isolated nucleic acid and proteins of the present invention can also be used in species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browallia, Glycine, Pisum, Phaseolus, Lolium, Oryza* and *Avena*.

Nucleic Acids

The present invention provides, among other things, isolated nucleic acids of RNA, DNA and analogs and/or chimeras thereof, comprising a polynucleotide of the present invention.

A polynucleotide of the present invention is inclusive of:
(a) a polynucleotide encoding a polypeptide of SEQ ID NO: 2, 4, 6, 8 or 10 and conservatively modified and polymorphic variants thereof, including exemplary polynucleotides of SEQ ID NO: 1, 3, 5, 7 or 9, (ETO1);
(b) an isolated polynucleotide which is the product of amplification from a plant nucleic acid library using primer pairs which selectively hybridize under stringent conditions to loci within a polynucleotide of the present invention;
(c) an isolated polynucleotide which selectively hybridizes to a polynucleotide of (a) or (b);
(d) an isolated polynucleotide having a specified sequence identity with polynucleotides of (a), (b) or (c);
(e) an isolated polynucleotide encoding a protein having a specified number of contiguous amino acids from a prototype polypeptide, wherein the protein is specifically recognized by antisera elicited by presentation of the protein and wherein the protein does not detectably immunoreact to antisera which has been fully immunosorbed with the protein;
(f) complementary sequences of polynucleotides of (a), (b), (c), (d) or (e); and
(g) an isolated polynucleotide comprising at least a specific number of contiguous nucleotides from a polynucleotide of (a), (b), (c), (d), (e) or (f);
(h) an isolated polynucleotide from a full-length enriched cDNA library having the physico-chemical property of selectively hybridizing to a polynucleotide of (a), (b), (c), (d), (e), (f) or (g);
(i) an isolated polynucleotide made by the process of: 1) providing a full-length enriched nucleic acid library, 2) selectively hybridizing the polynucleotide to a polynucleotide of (a), (b), (c), (d), (e), (f), (g) or (h), thereby isolating the polynucleotide from the nucleic acid library.

A. Polynucleotides Encoding a Polypeptide of the Present Invention

As indicated in (a), above, the present invention provides isolated nucleic acids comprising a polynucleotide of the present invention, wherein the polynucleotide encodes a polypeptide of the present invention. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine and UGG, which is ordinarily the only codon for tryptophan) can be modified to yield a functionally identical molecule. Thus, each silent variation of a nucleic acid which encodes a polypeptide of the present invention is implicit in each described polypeptide sequence and is within the scope of the present invention. Accordingly, the present invention includes polynucleotides of the present invention and polynucleotides encoding a polypeptide of the present invention.

B. Polynucleotides Amplified from a Plant Nucleic Acid Library

As indicated in (b), above, the present invention provides an isolated nucleic acid comprising a polynucleotide of the present invention, wherein the polynucleotides are amplified, under nucleic acid amplification conditions, from a plant nucleic acid library.

Nucleic acid amplification conditions for each of the variety of amplification methods are well known to those of ordinary skill in the art. The plant nucleic acid library can be constructed from a monocot such as a cereal crop. Exemplary cereals include corn, sorghum, alfalfa, canola, wheat or rice. The plant nucleic acid library can also be constructed from a dicot such as soybean. Zea mays lines B73, PHRE1, A632, BMP2#10, W23 and Mo17 are known and publicly available. Other publicly known and available maize lines can be obtained from the Maize Genetics Cooperation (Urbana, Ill.).

Wheat lines are available from the Wheat Genetics Resource Center (Manhattan, Kans.). The nucleic acid library may be a cDNA library, a genomic library or a library generally constructed from nuclear transcripts at any stage of intron processing. cDNA libraries can be normalized to increase the representation of relatively rare cDNAs. In optional embodiments, the cDNA library is constructed using an enriched full-length cDNA synthesis method. Examples of such methods include Oligo-Capping (Maruyama and Sugano, (1994) *Gene* 138:171-174), Biotinylated CAP Trapper (Carninci, et al., (1996) *Genomics* 37:327-336) and CAP Retention Procedure (Edery, et al., (1995) *Molecular and Cellular Biology* 15:3363-3371). Rapidly growing tissues or rapidly dividing cells are preferred for use as an mRNA source for construction of a cDNA library. Growth stages of corn are described in "How a Corn Plant Develops, "Special Report No. 48, Iowa State University of Science and Technology Cooperative Extension Service, Ames, Iowa, Reprinted February 1993.

A polynucleotide of this embodiment (or subsequences thereof) can be obtained, for example, by using amplification primers which are selectively hybridized and primer extended, under nucleic acid amplification conditions, to at least two sites within a polynucleotide of the present invention or to two sites within the nucleic acid which flank and comprise a polynucleotide of the present invention or to a site within a polynucleotide of the present invention and a site within the nucleic acid which comprises it. Methods for obtaining 5' and/or 3' ends of a vector insert are well known in the art. See, e.g., RACE (Rapid Amplification of Complementary Ends) as described in Frohman, in PCR Protocols: A Guide to Methods and Applications, Innis, et al., Eds. (Academic Press, Inc., San Diego), pp. 28-38 (1990)), see also, U.S. Pat. No. 5,470,722, and Current Protocols in Molecular Biology, Unit 15.6, Ausubel, et al., Eds., Greene Publishing and Wiley-Interscience, New York (1995); Frohman and Martin, (1989) *Techniques* 1:165.

Optionally, the primers are complementary to a subsequence of the target nucleic acid which they amplify but may have a sequence identity ranging from about 85% to 99% relative to the polynucleotide sequence which they are designed to anneal to. As those skilled in the art will appreciate, the sites to which the primer pairs will selectively hybridize are chosen such that a single contiguous nucleic acid can be formed under the desired nucleic acid amplification conditions. The primer length in nucleotides is selected from the group of integers consisting of from at least 15 to 50. Thus, the primers can be at least 15, 18, 20, 25, 30, 40 or 50 nucleotides in length. Those of skill will recognize that a lengthened primer sequence can be employed to increase specificity of binding (i.e., annealing) to a target sequence. A non-annealing sequence at the 5' end of a primer (a "tail") can be added, for example, to introduce a cloning site at the terminal ends of the amplicon.

The amplification products can be translated using expression systems well known to those of skill in the art. The resulting translation products can be confirmed as polypeptides of the present invention by, for example, assaying for the appropriate catalytic activity (e.g., specific activity and/or substrate specificity) or verifying the presence of one or more epitopes which are specific to a polypeptide of the present invention. Methods for protein synthesis from PCR derived templates are known in the art and available commercially. See, e.g., Amersham Life Sciences, Inc, Catalog '97, p. 354.

C. Polynucleotides which Selectively Hybridize to a Polynucleotide of (A) or (B)

As indicated in (c), above, the present invention provides isolated nucleic acids comprising polynucleotides of the present invention, wherein the polynucleotides selectively hybridize, under selective hybridization conditions, to a polynucleotide of sections (A) or (B) as discussed above. Thus, the polynucleotides of this embodiment can be used for isolating, detecting, and/or quantifying nucleic acids comprising the polynucleotides of (A) or (B). For example, polynucleotides of the present invention can be used to identify, isolate or amplify partial or full-length clones in a deposited library.

In some embodiments, the polynucleotides are genomic or cDNA sequences isolated or otherwise complementary to a cDNA from a dicot or monocot nucleic acid library.

Exemplary species of monocots and dicots include, but are not limited to: maize, canola, soybean, cotton, wheat, sorghum, sunflower, alfalfa, oats, sugar cane, millet, barley and rice. The cDNA library comprises at least 50% to 95% full-length sequences (for example, at least 50%, 60%, 70%, 80%, 90% or 95% full-length sequences). The cDNA libraries can be normalized to increase the representation of rare sequences. See, e.g., U.S. Pat. No. 5,482,845. Low stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% to 80% sequence identity and can be employed to identify orthologous or paralogous sequences.

D. Polynucleotides Having a Specific Sequence Identity with the Polynucleotides of (A), (B) or (C)

As indicated in (d), above, the present invention provides isolated nucleic acids comprising polynucleotides of the present invention, wherein the polynucleotides have a specified identity at the nucleotide level to a polynucleotide as disclosed above in sections (A), (B), or (C), above. Identity can be calculated using, for example, the BLAST, CLUSTALW or GAP algorithms under default conditions. The percentage of identity to a reference sequence is at least 60% and rounded upwards to the nearest integer, can be expressed as an integer selected from the group of integers consisting of from 60 to 99. Thus, for example, the percentage of identity to a reference sequence can be at least 70%, 75%, 80%, 85%, 90%, 91%, 92%, 93%, 94%, 95%, 96%, 97%, 98%, and 99% to a full-length sequence of the invention.

Optionally, the polynucleotides of this embodiment will encode a polypeptide that will share an epitope with a polypeptide encoded by the polynucleotides of sections (A), (B) or (C). Thus, these polynucleotides encode a first polypeptide which elicits production of antisera comprising antibodies which are specifically reactive to a second polypeptide encoded by a polynucleotide of (A), (B) or (C). However, the first polypeptide does not bind to antisera raised against itself when the antisera has been fully immunosorbed with the first polypeptide. Hence, the polynucleotides of this embodiment can be used to generate antibodies for use in, for example, the screening of expression libraries for nucleic acids comprising polynucleotides of (A), (B) or (C), or for purification of, or in immunoassays for, polypeptides encoded by the polynucleotides of (A), (B) or (C). The polynucleotides of this embodiment comprise nucleic acid sequences which can be employed for selective hybridization to a polynucleotide encoding a polypeptide of the present invention.

Screening polypeptides for specific binding to antisera can be conveniently achieved using peptide display libraries. This method involves the screening of large collections of peptides for individual members having the desired function or structure.

Antibody screening of peptide display libraries is well known in the art. The displayed peptide sequences can be from 3 to 5000 or more amino acids in length, frequently from 5100 amino acids long, and often from about 8 to 15 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Application Publication Numbers 1991/17271, 1991/18980, 1991/19818 and 1993/08278. Other systems for generating libraries of peptides have aspects of both in vitro chemical synthesis and recombinant methods. See, PCT Patent Application Publication Numbers 1992/05258, 1992/14843 and 1997/20078. See also, U.S. Pat. Nos. 5,658,754 and 5,643,768. Peptide display libraries, vectors and screening kits are commercially available from such suppliers as Invitrogen (Carlsbad, Calif.).

E. Polynucleotides Encoding a Protein Having a Subsequence from a Prototype Polypeptide and Cross-Reactive to the Prototype Polypeptide As indicated in (e), above, the present invention provides isolated nucleic acids comprising polynucleotides of the present invention, wherein the polynucleotides encode a protein having a subsequence of contiguous amino acids from a prototype polypeptide of the present invention such as are provided in (a), above. The length of contiguous amino acids from the prototype polypeptide is selected from the group of integers consisting of from at least 10 to the number of amino acids within the prototype sequence. Thus, for example, the polynucleotide can encode a polypeptide having a subsequence having at least 10, 15, 20, 25, 30, 35, 40, 45 or 50, contiguous amino acids from the prototype polypeptide. Further, the number of such subsequences encoded by a polynucleotide of the instant embodiment can be any integer selected from the group consisting of from 1 to 20, such as 2, 3, 4 or 5. The subsequences can be separated by any integer of nucleotides from 1 to the number of nucleotides in the sequence such as at least 5, 10, 15, 25, 50, 100 or 200 nucleotides.

The proteins encoded by polynucleotides of this embodiment, when presented as an immunogen, elicit the production of polyclonal antibodies which specifically bind to a prototype polypeptide such as but not limited to, a polypeptide encoded by the polynucleotide of (a) or (b), above. Generally, however, a protein encoded by a polynucleotide of this embodiment does not bind to antisera raised against the prototype polypeptide when the antisera has been fully immunosorbed with the prototype polypeptide. Methods of making and assaying for antibody binding specificity/affinity are well known in the art. Exemplary immunoassay formats include ELISA, competitive immunoassays, radioimmunoassays, Western blots, indirect immunofluorescent assays and the like.

In a preferred assay method, fully immunosorbed and pooled antisera which is elicited to the prototype polypeptide can be used in a competitive binding assay to test the protein. The concentration of the prototype polypeptide required to inhibit 50% of the binding of the antisera to the prototype polypeptide is determined. If the amount of the protein required to inhibit binding is less than twice the amount of the prototype protein, then the protein is said to specifically bind to the antisera elicited to the immunogen.

Accordingly, the proteins of the present invention embrace allelic variants, conservatively modified variants and minor recombinant modifications to a prototype polypeptide.

A polynucleotide of the present invention optionally encodes a protein having a molecular weight as the non-glycosylated protein within 20% of the molecular weight of the full-length non-glycosylated polypeptides of the present invention. Molecular weight can be readily determined by SDS-PAGE under reducing conditions. Optionally, the molecular weight is within 15% of a full length polypeptide of the present invention, more preferably within 10% or 5% and most preferably within 3%, 2% or 1% of a full length polypeptide of the present invention. Optionally, the polynucleotides of this embodiment will encode a protein having a specific enzymatic activity at least 50%, 60%, 80% or 90% of a cellular extract comprising the native, endogenous full-length polypeptide of the present invention.

Further, the proteins encoded by polynucleotides of this embodiment will optionally have a substantially similar affinity constant (Km) and/or catalytic activity (i.e., the microscopic rate constant, kcat) as the native endogenous, full-length protein. Those of skill in the art will recognize that kcat/Km value determines the specificity for competing substrates and is often referred to as the specificity constant. Proteins of this embodiment can have akcat/Km value at least 10% of a full-length polypeptide of the present invention as determined using the endogenous substrate of that polypeptide. Optionally, the kcat/Km value will be at least 20%, 30%, 40%, 50% and most preferably at least 60%, 70%, 80%, 90% or 95% the kcat/Km value of the full-length polypeptide of the present invention.

Determination of kcat, Km and kcat/Km can be determined by any number of means well known to those of skill in the art. For example, the initial rates (i.e., the first 5% or less of the reaction) can be determined using rapid mixing and sampling techniques (e.g., continuous-flow, stopped-flow or rapid quenching techniques), flash photolysis or relaxation methods (e.g., temperature jumps) in conjunction with such exemplary methods of measuring as spectrophotometry, spectrofluorimetry, nuclear magnetic resonance or radioactive procedures. Kinetic values are conveniently obtained using a Lineweaver Burk or Eadie-Hofstee plot.

F. Polynucleotides Complementary to the Polynucleotides of (A)-(E)

As indicated in (f), above, the present invention provides isolated nucleic acids comprising polynucleotides complementary to the polynucleotides of paragraphs A-E, above. As those of skill in the art will recognize, complementary sequences base-pair throughout the entirety of their length with the polynucleotides of sections (A)-(E) (i.e., have 100% sequence identity over their entire length). Complementary bases associate through hydrogen bonding in double stranded nucleic acids. For example, the following base pairs are complementary: guanine and cytosine; adenine and thymine and adenine and uracil.

G. Polynucleotides which are Subsequences of the Polynucleotides of (A)-(F)

As indicated in (g), above, the present invention provides isolated nucleic acids comprising polynucleotides which comprise at least 15 contiguous bases from the polynucleotides of sections (A) through (F) as discussed above. The length of the polynucleotide is given as an integer selected from the group consisting of from at least 15 to the length of the nucleic acid sequence from which the polynucleotide is a subsequence of. Thus, for example, polynucleotides of the present invention are inclusive of polynucleotides comprising at least 15, 20, 25, 30, 40, 50, 60, 75 or 100 contiguous nucleotides in length from the polynucleotides of (A)-(F). Optionally, the number of such subsequences encoded by a polynucleotide of the instant embodiment can be any integer selected from the group consisting of from 1 to 20, such as 2, 3, 4 or 5. The subsequences can be separated by any integer of nucleotides from 1 to the number of nucleotides in the sequence such as at least 5, 10, 15, 25, 50, 100 or 200 nucleotides.

Subsequences can be made by in vitro synthetic, in vitro biosynthetic or in vivo recombinant methods. In optional embodiments, subsequences can be made by nucleic acid amplification. For example, nucleic acid primers will be constructed to selectively hybridize to a sequence (or its complement) within, or co-extensive with, the coding region.

The subsequences of the present invention can comprise structural libraries as are known in the art and discussed briefly below. The cDNA library comprises at least 50% to 95% full-length sequences (for example, at least 50%, 60%, 70%, 80%, 90% or 95% full-length sequences). The cDNA library can be constructed from a variety of tissues from a monocot or dicot at a variety of developmental stages. Exemplary species include maize, wheat, rice, canola, soybean, cotton, sorghum, sunflower, alfalfa, oats, sugar cane, millet, barley and rice. Methods of selectively hybridizing, under selective hybridization conditions, a polynucleotide from a full-length enriched library to a polynucleotide of the present invention are known to those of ordinary skill in the art. Any number of stringency conditions can be employed to allow for selective hybridization. In optional embodiments, the stringency allows for selective hybridization of sequences having at least 70%, 75%, 80%, 85%, 90%, 95% or 98% sequence identity over the length of the hybridized region. Full-length enriched cDNA libraries can be normalized to increase the representation of rare sequences.

H. Polynucleotide Products Made by a cDNA Isolation Process

As indicated in (I), above, the present invention provides an isolated polynucleotide made by the process of: 1) providing a full-length enriched nucleic acid library, 2) selectively hybridizing the polynucleotide to a polynucleotide of paragraphs (A), (B), (C), (D), (E), (F), (G) or (H) as discussed above and thereby isolating the polynucleotide from the nucleic acid library. Full-length enriched nucleic acid libraries are constructed as discussed in paragraph (G) and below. Selective hybridization conditions are as discussed in paragraph (G). Nucleic acid purification procedures are well known in the art.

Purification can be conveniently accomplished using solid-phase methods; such methods are well known to those of skill in the art and kits are available from commercial suppliers such as Advanced Biotechnologies (Surrey, UK). For example, a polynucleotide of paragraphs (A)-(H) can be immobilized to a solid support such as a membrane, bead or particle. See, e.g., U.S. Pat. No. 5,667,976. The polynucleotide product of the present process is selectively hybridized to an immobilized polynucleotide and the solid support is subsequently isolated from non-hybridized polynucleotides by methods including, but not limited to, centrifugation, magnetic separation, filtration, electrophoresis, and the like.

Construction of Nucleic Acids

The isolated nucleic acids of the present invention can be made using (a) standard recombinant methods, (b) synthetic techniques or combinations thereof. In some embodiments, the polynucleotides of the present invention will be cloned, amplified or otherwise constructed from a monocot such as corn, rice or wheat or a dicot such as soybean.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexahistidine marker sequence provides a convenient means to purify the proteins of the present invention. A polynucleotide of the present invention can be attached to a vector, adapter or linker for cloning and/or expression of a polynucleotide of the present invention. Additional sequences may be added to such cloning and/or expression sequences to optimize their function in cloning and/or expression, to aid in isolation of the polynucleotide or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters, and linkers is well known and extensively described in the art. For a description of various nucleic acids see, for example, Stratagene Cloning Systems, Catalogs 1999 (La Jolla, Calif.); and Amersham Life Sciences, Inc, Catalog '99 (Arlington Heights, Ill.).

A. Recombinant Methods for Constructing Nucleic Acids

The isolated nucleic acid compositions of this invention, such as RNA, cDNA, genomic DNA or a hybrid thereof, can be obtained from plant biological sources using any number of cloning methodologies known to those of skill in the art. In some embodiments, oligonucleotide probes which selectively hybridize, under stringent conditions, to the polynucleotides of the present invention are used to identify the desired sequence in a cDNA or genomic DNA library. Isolation of RNA and construction of cDNA and genomic libraries is well known to those of ordinary skill in the art. See, e.g., Plant Molecular Biology: A Laboratory Manual, Clark, Ed., Springer-Verlag, Berlin (1997); and Current Protocols in Molecular Biology, Ausubel, et al., Eds., Greene Publishing and Wiley-Interscience, New York (1995).

A1. Full-Length Enriched cDNA Libraries

A number of cDNA synthesis protocols have been described which provide enriched full-length cDNA libraries. Enriched full-length cDNA libraries are constructed to comprise at least 60%, and more preferably at least 70%, 80%, 90% or 95% full-length inserts amongst clones containing inserts. The length of insert in such libraries can be at least 2, 3, 4, 5, 6, 7, 8, 9, 10 or more kilobase pairs. Vectors to accommodate inserts of these sizes are known in the art and available commercially. See, e.g., Stratagene's lambda ZAP Express (cDNA cloning vector with 0 to 12 kb cloning capacity). An exemplary method of constructing a greater than 95% pure full-length cDNA library is described by Carninci, et al., (1996) *Genomics* 37:327-336. Other methods for producing full-length libraries are known in the art. See, e.g., Edery, et al., (1995) *Mol. Cell. Biol.* 15(6):3363-3371 and PCT Application Publication Number WO 1996/34981.

A2. Normalized or Subtracted cDNA Libraries

A non-normalized cDNA library represents the mRNA population of the tissue it was made from. Since unique clones are out-numbered by clones derived from highly expressed genes their isolation can be laborious. Normalization of a cDNA library is the process of creating a library in which each clone is more equally represented. Construction of normalized libraries is described in Ko, (1990) *Nucl. Acids. Res.* 18(19):5705-5711; Patanjali, et al., (1991) *Proc. Natl. Acad. USA* 88:1943-1947; U.S. Pat. Nos. 5,482,685, 5,482,845 and 5,637,685. In an exemplary method described by Soares, et al., normalization resulted in reduction of the abundance of clones from a range of four orders of magnitude to a narrow range of only 1 order of magnitude. *Proc. Natl. Acad. Sci. USA* 91:9228-9232 (1994).

Subtracted cDNA libraries are another means to increase the proportion of less abundant cDNA species. In this procedure, cDNA prepared from one pool of mRNA is depleted of sequences present in a second pool of mRNA by hybridization. The cDNA: mRNA hybrids are removed and the remaining un-hybridized cDNA pool is enriched for sequences unique to that pool. See, Foote, et al. in, Plant Molecular Biology: A Laboratory Manual, Clark, Ed., Springer-Verlag, Berlin (1997); Kho and Zarbl, (1991) *Technique* 3(2):58-63; Sive and St. John, (1988) *Nucl. Acids Res.* 16(22):10937; Current Protocols in Molecular Biology, Ausubel, et al., Eds., Greene Publishing and Wiley-Interscience, New York (1995) and Swaroop, et al., (1991) *Nucl. Acids Res.* 19(8):1954. cDNA subtraction kits are commercially available. See, e.g., PCR-Select (Clontech, Palo Alto, Calif.).

To construct genomic libraries, large segments of genomic DNA are generated by fragmentation, e.g., using restriction endonucleases, and are ligated with vector DNA to form concatemers that can be packaged into the appropriate vector. Methodologies to accomplish these ends and sequencing methods to verify the sequence of nucleic acids are well known in the art. Examples of appropriate molecular biological techniques and instructions sufficient to direct persons of skill through many construction, cloning, and screening methodologies are found in Sambrook, et al., Molecular Cloning: A Laboratory Manual, 2nd Ed., Cold Spring Harbor Laboratory Vols. 1-3 (1989), Methods in Enzymology, Vol. 152: Guide to Molecular Cloning Techniques, Berger and Kimmel, Eds., San Diego: Academic Press, Inc. (1987), Current Protocols in Molecular Biology, Ausubel, et al., Eds., Greene Publishing and Wiley-Interscience, New York (1995); Plant Molecular Biology: A Laboratory Manual, Clark, Ed., Springer-Verlag, Berlin (1997). Kits for construction of genomic libraries are also commercially available.

The cDNA or genomic library can be screened using a probe based upon the sequence of a polynucleotide of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay and either the hybridization or the wash medium can be stringent.

The nucleic acids of interest can also be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. The T4 gene 32 protein (Boehringer Mannheim) can be used to improve yield of long PCR products.

PCR-based screening methods have been described. Wilfinger, et al., describe a PCR-based method in which the longest cDNA is identified in the first step so that incomplete clones can be eliminated from study. *Bio Techniques* 22(3): 481-486 (1997). Such methods are particularly effective in combination with a full-length cDNA construction methodology, above.

B. Synthetic Methods for Constructing Nucleic Acids

The isolated nucleic acids of the present invention can also be prepared by direct chemical synthesis by methods such as the phosphotriester method of Narang, et al., (1979) *Meth. Enzymol.* 68:90-99; the phosphodiester method of Brown, et al., (1979) *Meth. Enzymol.* 68:109-151; the diethylphosphoramidite method of Beaucage, et al., (1981) *Tetra. Lett.* 22:1859-1862; the solid phase phosphoramidite triester method described by Beaucage and Caruthers, (1981) *Tetra. Letts.* 22(20):1859-1862, e.g., using an automated synthesizer, e.g., as described in Needham-VanDevanter, et al., (1984) *Nucleic Acids Res.* 12:6159-6168 and the solid support method of U.S. Pat. No. 4,458,066. Chemical synthesis generally produces a single stranded oligonucleotide. This may be converted into double stranded DNA by hybridization with a complementary sequence or by polymerization with a DNA polymerase using the single strand as a template. One of skill will recognize that while chemical synthesis of DNA is best employed for sequences of about 100 bases or less, longer sequences may be obtained by the ligation of shorter sequences.

Recombinant Expression Cassettes

The present invention further provides recombinant expression cassettes comprising a nucleic acid of the present invention. A nucleic acid sequence coding for the desired polypeptide of the present invention, for example a cDNA or a genomic sequence encoding a full length polypeptide of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated or cell- or tissue-specific/selective expression), a transcription initiation start site, a ribosome binding site, an RNA processing signal, a transcription termination site and/or a polyadenylation signal.

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the cauliflower mosaic virus (CaMV) $^{35}$S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter and other transcription initiation regions from various plant genes known to those of skill. Constitutive promoters of particular interest for use in soybean include SCP1 and At-UBQ10.

Examples of promoters under developmental control include promoters that initiate transcription only, or preferentially, in certain tissues, such as leaves, roots, fruit, seeds, or flowers. Exemplary promoters include the anther specific promoter 5126 (U.S. Pat. Nos. 5,689,049 and 5,689,051), glob-1 promoter and gamma-zein promoter.

Promoters of interest in constructs designed to drive expression preferentially in female reproductive tissues include the maize Zag2.1 promoter (GenBank Number X80206; Schmidt, et al., (1993) *Plant Cell* 5(7):729-737); maize Zap promoter (U.S. Pat. No. 7,560,612); maize ckx1-2 promoter (US Patent Application Publication Number 2002/0152500 A1); ZM-ADF4 (US Patent Application Publication Number 2009/0094713); maize eep1 promoter (US Patent Application Publication Number 2004/0237147); maize end2 promoter, (U.S. Pat. Nos. 6,528,704 and 6,903,205); maize lec1 promoter (U.S. Pat. No. 7,122,658); maize F3.7 promoter (Baszczynski, et al., (1997) *Maydica* 42:189-201); maize tb1 promoter (Hubbarda, et al., (2002) *Genetics* 162:1927-1935); maize eep2 promoter (US Patent Application Publication Number 2004/0237147); maize thioredoxinH promoter, US Provisional Patent Application Ser. No. 60/514,123); maize Zm40 promoter (U.S. Pat. No. 6,403,862) maize mLIP15 promoter (U.S. Pat. No. 6,479,734); maize ESR promoter (U.S. Pat. No. 7,276,596); maize PCNA2 promoter (US Patent Application Publication Number 2005/0120404).

Root-preferred promoters include Zm-NAS2 (U.S. patent application Ser. No. 12/030,455, filed Feb. 13, 2008), Zm-Cyclo1 promoter (U.S. Pat. No. 7,268,226), Zm-Metallothionein promoters (U.S. Pat. Nos. 6,774,282; 7,214,854 and 7,214,855 (also known as RootMET2)), Zm-MSY promoter (SEQ ID NO: 64; U.S. Patent Application Ser. No. 60/971,310 filed Sep. 11, 2007) or MsZRP promoter (SEQ ID NO: 65; see, U.S. Pat. No. 5,633,363). Additional root-preferred promoters include the VfENOD-GRP3 gene promoter (Kuster, et al., (1995) *Plant Mol. Biol.* 29(4):759-772); rolB promoter (Capana, et al., (1994) *Plant Mol. Biol.* 25(4):681-691; and the CRWAQ81 root-preferred promoter with the ADH first intron (US Patent Application Publication Number 2005/0097633). See also, U.S. Pat. Nos. 5,837,876; 5,750,386; 5,633,363; 5,459,252; 5,401,836; 5,110,732 and 5,023,179.

Alternatively, the plant promoter may be under more precise environmental control. Such promoters are referred to here as "inducible" promoters. Environmental conditions that may effect transcription by inducible promoters include pathogen attack, anaerobic conditions, or the presence of light. Examples of inducible promoters are the Adh1 promoter which is inducible by hypoxia or cold stress, the Hsp70 promoter which is inducible by heat stress and the PPDK promoter which is inducible by light.

The operation of a promoter may also vary depending on its location in the genome. Thus, an inducible promoter may become fully or partially constitutive in certain locations.

Both heterologous and non-heterologous (i.e., endogenous) promoters can be employed to direct expression of the nucleic acids of the present invention. These promoters can also be used, for example, in recombinant expression cassettes to drive expression of antisense nucleic acids to reduce, increase, or alter concentration and/or composition of the proteins of the present invention in a desired tissue. Thus, in some embodiments, the nucleic acid construct will comprise a promoter functional in a plant cell, such as in *Zea mays*, operably linked to a polynucleotide of the present invention. Promoters useful in these embodiments include the endogenous promoters driving expression of a polypeptide of the present invention.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution (see, Kmiec, U.S. Pat. No. 5,565,350; Zarling, et al., PCT Patent Application Number PCT/US93/03868) or isolated promoters can be introduced into a plant cell in the proper orientation and distance from a gene of the present invention so as to control the expression of the gene. Gene expression can be modulated under conditions suitable for plant growth so as to alter the total concentration and/or alter the composition of the polypeptides of the present invention in plant cell.

Thus, the present invention provides compositions, and methods for making, heterologous promoters and/or enhancers operably linked to a native, endogenous (i.e., nonheterologous) form of a polynucleotide of the present invention.

Methods for identifying promoters with a particular expression pattern, in terms of, e.g., tissue type, cell type, stage of development and/or environmental conditions, are well known in the art. See, e.g., The Maize Handbook, Chapters 114-115, Freeling and Walbot, Eds., Springer, New York (1994); Corn and Corn Improvement, 3rd edition, Chapter 6, Sprague and Dudley, Eds., American Society of Agronomy, Madison, Wis. (1988).

A typical step in promoter isolation methods is identification of gene products that are expressed with some degree of specificity in the target tissue. Amongst the range of methodologies are: differential hybridization to cDNA libraries; subtractive hybridization; differential display; differential 2-D protein gel electrophoresis; DNA probe arrays and isolation of proteins known to be expressed with some specificity in the target tissue. Such methods are well known to those of skill in the art. Commercially available products for identifying promoters are known in the art such as Clontech's (Palo Alto, Calif.) Universal Genome Walker Kit.

For the protein-based methods, it is helpful to obtain the amino acid sequence for at least a portion of the identified protein, and then to use the protein sequence as the basis for preparing a nucleic acid that can be used as a probe to identify either genomic DNA directly, or preferably, to identify a cDNA clone from a library prepared from the target tissue. Once such a cDNA clone has been identified, that sequence can be used to identify the sequence at the 5' end of the transcript of the indicated gene. For differential hybridization, subtractive hybridization and differential display, the nucleic acid sequence identified as enriched in the target tissue is used to identify the sequence at the 5' end of the transcript of the indicated gene. Once such sequences are identified, starting either from protein sequences or nucleic acid sequences, any of these sequences identified as being from the gene transcript can be used to screen a genomic library prepared from the target organism. Methods for identifying and confirming the transcriptional start site are well known in the art.

In the process of isolating promoters expressed under particular environmental conditions or stresses, or in specific tissues, or at particular developmental stages, a number of genes are identified that are expressed under the desired circumstances, in the desired tissue, or at the desired stage. Further analysis will reveal expression of each particular gene in one or more other tissues of the plant. One can identify a promoter with activity in the desired tissue or condition but that does not have activity in any other common tissue.

To identify the promoter sequence, the 5' portions of the clones described here are analyzed for sequences characteristic of promoter sequences. For instance, promoter sequence elements include the TATA box consensus sequence (TATAAT), which is usually an AT-rich stretch of 5-10 bp located approximately 20 to 40 base pairs upstream of the transcription start site. Identification of the TATA box is well known in the art. For example, one way to predict the location of this element is to identify the transcription start site using standard RNA-mapping techniques such as primer extension, S 1 analysis, and/or RNase protection. To confirm the presence of the AT-rich sequence, a structure-function analysis can be performed involving mutagenesis of the putative region and quantification of the mutation's effect on expression of a linked downstream reporter gene. See, e.g., The Maize Handbook, Chapter 114, Freeling and Walbot, Eds., Springer, New York, (1994).

In plants, further upstream from the TATA box, at positions-80 to -100, there is typically a promoter element (i.e., the CAAT box) with a series of adenines surrounding the trinucleotide G (or T) N G. Messing, et al., in Genetic Engineering in Plants, Kosage, Meredith and Hollaender, Eds., pp. 221-227 1983. In maize, there is no well conserved CAAT box but there are several short, conserved protein-binding motifs upstream of the TATA box. These include motifs for the trans-acting transcription factors involved in light regulation, anaerobic induction, hormonal regulation or anthocyanin biosynthesis, as appropriate for each gene.

Once promoter and/or gene sequences are known, a region of suitable size is selected from the genomic DNA that is 5' to the transcriptional start, or the translational start site and such sequences are then linked to a coding sequence. If the transcriptional start site is used as the point of fusion, any of a number of possible 5' untranslated regions can be used in between the transcriptional start site and the partial coding sequence. If the translational start site at the 3' end of the specific promoter is used, then it is linked directly to the methionine start codon of a coding sequence.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes or alternatively from another plant gene or less preferably from any other eukaryotic gene.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, (1988) Mol. Cell Biol. 8:4395-4405; Callis, et al., (1987) Genes Dev. 1:1183-1200. Such intron enhancement of gene expression is typically greatest when placed near the 5' end of the transcription unit. Use of maize introns Adhl-S intron1, 2 and 6, the Bronze-1 intron are known in the art. See generally, The Maize Handbook, Chapter 116, Freeling and Walbot, Eds., Springer, New York (1994).

The vector comprising the sequences from a polynucleotide of the present invention will typically comprise a marker gene which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or genetic in resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene) or other such genes known in the art. The bar gene encodes resistance to the herbicide basta, the nptII gene encodes resistance to the antibiotic kanamycin, and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers, et al., (1987) *Meth. in Enzymol.* 153:253-277. These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl, et al., (1987) *Gene* 61:1-11 and Berger, et al., (1989) *Proc. Natl. Acad. Sci. USA* 86:8402-8406. Another useful vector herein is plasmid pBI101.2 that is available from Clontech Laboratories, Inc. (Palo Alto, Calif.).

A polynucleotide of the present invention can be expressed in either sense or antisense orientation as desired. It will be appreciated that control of gene expression in either sense or anti-sense orientation can have a direct impact on the observable plant characteristics. Antisense technology can be conveniently used to inhibit gene expression in plants. To accomplish this, a nucleic acid segment from the desired gene is cloned and operably linked to a promoter such that the antisense strand of RNA will be transcribed. The construct is then transformed into plants and the antisense strand of RNA is produced.

In plant cells, it has been shown that antisense RNA inhibits gene expression by preventing the accumulation of mRNA which encodes the enzyme of interest, see, e.g., Sheehy, et al., (1988) *Proc. Nat'l. Acad. Sci.* (*USA*) 85:8805-8809 and Hiatt, et al., U.S. Pat. No. 4,801,340.

Another method of suppression is sense suppression. Introduction of nucleic acid configured in the sense orientation has been shown to be an effective means by which to block the transcription of target genes. For an example of the use of this method to modulate expression of endogenous genes see, Napoli, et al., (1990) *The Plant Cell* 2:279-289 and U.S. Pat. No. 5,034,323.

Catalytic RNA molecules or ribozymes can also be used to inhibit expression of plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA cleaving activity upon them, thereby increasing the activity of the constructs. The design and use of target RNA-specific ribozymes is described in Haseloff, et al., (1988) *Nature* 334:585-591. A variety of cross-linking agents, alkylating agents and radical generating species as pendant groups on polynucleotides of the present invention can be used to bind, label, detect, and/or cleave nucleic acids. For example, Vlassov, et al., (1986) *Nucleic*

*Acids Res* 14:4065-4076, describe covalent bonding of a single-stranded DNA fragment with alkylating derivatives of nucleotides complementary to target sequences. A report of similar work by the same group is that by Knorre, et al., (1985) *Biochimie* 67:785 789. Iverson and Dervan.

The present invention further provides a protein comprising a polypeptide having a specified sequence identity with a polypeptide of the present invention. The percentage of sequence identity is an integer selected from the group consisting of from 60 to 99. Exemplary sequence identity values include 60%, 65%, 70%, 75%, 80%, 85%, 90%, 91%, 92%, 93%, 94%, 95%, 96%, 97%, 98% and 99% to a full-length sequence of the invention.

As those of skill will appreciate, the present invention includes catalytically active polypeptides of the present invention (i.e., enzymes). Catalytically active polypeptides have a specific activity of at least 20%, 30% or 40%, and preferably at least 50%, 60% or 70% and most preferably at least 80%, 90% or 95% that of the native (non-synthetic), endogenous polypeptide. Further, the substrate specificity (kcat/Km) is optionally substantially similar to the native (non-synthetic), endogenous polypeptide. Typically, the Km will be at least 30%, 40% or 50%, that of the native (non-synthetic), endogenous polypeptide and more preferably at least 60%, 70%, 80% or 90%. Methods of assaying and quantifying measures of enzymatic activity and substrate specificity (kcat/Km), are well known to those of skill in the art.

Generally, the proteins of the present invention will, when presented as an immunogen, elicit production of an antibody specifically reactive to a polypeptide of the present invention. Further, the proteins of the present invention will not bind to antisera raised against a polypeptide of the present invention which has been fully immunosorbed with the same polypeptide. Immunoassays for determining binding are well known to those of skill in the art. A preferred immunoassay is a competitive immunoassay as discussed, infra. Thus, the proteins of the present invention can be employed as immunogens for constructing antibodies immunoreactive to a protein of the present invention for such exemplary utilities as immunoassays or protein purification techniques.

Expression of Proteins in Host Cells

Using the nucleic acids of the present invention, one may express a protein of the present invention in a recombinantly engineered cell such as bacteria, yeast, insect, mammalian or preferably plant cells. The cells produce the protein in a non-natural condition (e.g., in quantity, composition, location and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or regulatable), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation and a transcription/translation terminator. One of skill would recognize that modifications can be made to a protein of the present invention without diminishing its biological activity. Some modifications may be made to facilitate the cloning, expression, or incorporation of the targeting molecule into a fusion protein.

Such modifications are well known to those of skill in the art and include, for example, a methionine added at the amino terminus to provide an initiation site, or additional amino acids (e.g., poly His) placed on either terminus to create conveniently located purification sequences. Restriction sites or termination codons can also be introduced.

A. Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang, et al., (1977) *Nature* 198:1056), the tryptophan (trp) promoter system (Goeddel, et al., (1980) *Nucleic Acids Res.* 8:4057) and the lambda derived P L promoter and N-gene ribosome binding site (Shimatake, et al., (1981) *Nature* 292:128). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva, et al., (1983) *Gene* 22:229-235; Mosbach, et al., (1983) *Nature* 302:543-545).

B. Expression in Eukaryotes

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, et al., Methods in Yeast Genetics, Cold Spring Harbor Laboratory (1982) is a well recognized work describing the various methods available to produce the protein in yeast. Two widely utilized yeast for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen).

Suitable vectors usually have expression control sequences, such as promoters, including 3-phosphoglycerate kinase or alcohol oxidase and an origin of replication, termination sequences and the like as desired.

A protein of the present invention, once expressed, can be isolated from yeast by lysing the cells and applying standard protein isolation techniques to the lysate. The monitoring of the purification process can be accomplished by using Western blot techniques or radioimmunoassay or other standard immunoassay techniques.

The sequences encoding proteins of the present invention can also be ligated to various expression vectors for use in transfecting cell cultures of, for instance, mammalian, insect or plant origin. Illustrative of cell cultures useful for the production of the peptides are mammalian cells. Mammalian cell systems often will be in the form of monolayers of cells although mammalian cell suspensions may also be used. A number of suitable host cell lines capable of expressing intact proteins have been developed in the art, and include the HEK293, BHK21 and CHO cell lines. Expression vectors for these cells can include expression control sequences, such as an origin of replication, a promoter (e.g., the CMV promoter, a HSVtk promoter or pgk (phosphoglycerate kinase) promoter), an enhancer (Queen, et al., (1986) $Immunol.$ $Rev.$ 89:49) and necessary processing information sites, such as ribosome binding sites, RNA splice sites, polyadenylation sites (e.g., an SV40 large T Ag poly A addition site) and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, army worm, moth and $Drosophila$ cell lines such as a Schneider cell line (see, Schneider, (1987) $Embryol.$ $Exp.$ $Morphol.$ 27:353-365.

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague, et al., (1983) $J.$ $Virol.$ 45:773-781). Additionally, gene sequences to control replication in the host cell may be incorporated into the vector such as those found in bovine papilloma virus type-vectors. Saveria-Campo, Bovine Papilloma Virus DNA a Eukaryotic Cloning Vector in DNA Cloning Vol. II a Practical Approach, Glover, Ed., IRL Press, Arlington, Va. pp. 213-238 (1985).

Increasing the Activity and/or Level of an ETO1 Polypeptide

Methods are provided to increase the activity and/or level of the ETO1 polypeptide of the invention. An increase in the level and/or activity of the ETO1 polypeptide of the invention can be achieved by providing to the plant an ETO1 polypeptide. The ETO1 polypeptide can be provided by introducing the amino acid sequence encoding the ETO1 polypeptide into the plant, introducing into the plant a nucleotide sequence encoding an ETO1 polypeptide or alternatively by modifying a genomic locus encoding the ETO1 polypeptide of the invention.

As discussed elsewhere herein, many methods are known in the art for providing a polypeptide to a plant including, but not limited to, direct introduction of the polypeptide into the plant, introducing into the plant (transiently or stably) a polynucleotide construct encoding a polypeptide having enhanced activity. It is also recognized that the methods of the invention may employ a polynucleotide that is not capable of directing, in the transformed plant, the expression of a protein or an RNA. Thus, the level and/or activity of an ETO1 polypeptide may be increased by altering the gene encoding the ETO1 polypeptide or its promoter. See, e.g., Kmiec, U.S. Pat. No. 5,565,350; Zarling, et al., PCT Application Serial Number PCT/US93/03868. Therefore mutagenized plants that carry mutations in ETO1 genes, where the mutations increase expression of the ETO1 or increase the activity of the encoded ETO1 polypeptide, are provided.

Reducing the Activity and/or Level of an ETO1 Polypeptide

In certain embodiments, methods are provided to reduce or eliminate the activity of an ETO1 polypeptide of the invention by transforming a plant cell with an expression cassette that expresses a polynucleotide that inhibits the expression of the ETO1 polypeptide. The polynucleotide may inhibit the expression of the ETO1 polypeptide directly, by preventing transcription or translation of the ETO1 associated messenger RNA or indirectly, by encoding a polypeptide that inhibits the transcription or translation of an ETO1 gene encoding ETO1 polypeptide. Methods for inhibiting or eliminating the expression of a gene in a plant are well known in the art and any such method may be used in the present invention to inhibit the expression of ETO1 polypeptide.

In accordance with the present invention, the expression of an ETO1 polypeptide is inhibited if the protein level of the ETO1 polypeptide is less than 70% of the protein level of the same ETO1 polypeptide in a plant that has not been genetically modified or mutagenized to inhibit the expression of that ETO1 polypeptide. In particular embodiments of the invention, the protein level of the ETO1 polypeptide in a modified plant according to the invention is less than 60%, less than 50%, less than 40%, less than 30%, less than 20%, less than 10%, less than 5% or less than 2% of the protein level of the same ETO1 polypeptide in a plant that is not a mutant or that has not been genetically modified to inhibit the expression of that ETO1 polypeptide. The expression level of the ETO1 polypeptide may be measured directly, for example, by assaying for the level of ETO1 polypeptide expressed in the plant cell or plant, or indirectly, for example, by measuring the ethylene response in the plant cell or plant, or by measuring the phenotypic changes in the plant. Methods for performing such assays are described elsewhere herein.

In other embodiments of the invention, the activity of the ETO1 polypeptide is reduced or eliminated by transforming a plant cell with an expression cassette comprising a polynucleotide encoding a polypeptide that inhibits the activity of an ETO1 polypeptide. The activity of an ETO1 polypeptide is inhibited according to the present invention if the activity of the ETO1 polypeptide is less than 70% of the activity of the same ETO1 polypeptide in a plant that has not been modified to inhibit the activity of that polypeptide. In particular embodiments of the invention, the activity of the ETO1 polypeptide in a modified plant according to the invention is less than 60%, less than 50%, less than 40%, less than 30%, less than 20%, less than 10% or less than 5% of the activity of the same polypeptide in a plant that that has not been modified to inhibit the expression of that ETO1 polypeptide. The activity of an ETO1 polypeptide is "eliminated" according to the invention when it is not detectable by the assay methods described elsewhere herein. Methods of determining the alteration of activity of an ETO1 polypeptide are described elsewhere herein.

In other embodiments, the activity of an ETO1 polypeptide may be reduced or eliminated by disrupting the gene encoding the ETO1 polypeptide. The invention encompasses mutagenized plants that carry mutations in ETO1 genes, where the mutations reduce expression of the associated gene or inhibit the activity of the encoded ETO1 polypeptide.

Thus, many methods may be used to reduce or eliminate the activity of an ETO1 polypeptide. In addition, more than one method may be used to reduce the activity of a single ETO1 polypeptide.

1. Polynucleotide-Based Methods:

In some embodiments of the present invention, a plant is transformed with an expression cassette that is capable of expressing a polynucleotide that inhibits the expression of an ETO1 polypeptide of the invention. The term "expression" as used herein refers to the biosynthesis of a gene product, including the transcription and/or translation of said gene product. For example, for the purposes of the present invention, an expression cassette capable of expressing a polynucleotide that inhibits the expression of at least one ETO1 polypeptide is an expression cassette capable of producing an RNA molecule that inhibits the transcription and/or translation of at least one ETO1 polypeptide of the invention. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides and methodology that inhibit the expression of an ETO1 polypeptide include, sense suppression, cosuppression, antisense suppression, double stranded RNA interference, hairpin RNA Interference, intron-containing hairpin RNA interference, amplicon-mediated interference, ribozymes, small interfering RNA or micro RNA. Other methods of inhibition can include polypeptide-based inhibition of gene expression, or of protein activity as well as gene disruption.

2. Mutant Plants with Reduced Activity:

Additional methods for decreasing or eliminating the expression of endogenous genes in plants are also known in the art and can be similarly applied to the instant invention. These methods include other forms of mutagenesis, such as ethyl methanesulfonate-induced mutagenesis, deletion mutagenesis, and fast neutron deletion mutagenesis used in a reverse genetics sense (with PCR) to identify plant lines in which the endogenous gene has been deleted. For examples of these methods see, Ohshima, et al., (1998) *Virology* 243: 472-481; Okubara, et al., (1994) *Genetics* 137:867-874 and Quesada, et al., (2000) *Genetics* 154:421-436; each of which is herein incorporated by reference. In addition, a fast and automatable method for screening for chemically induced mutations, TILLING (Targeting Induced Local Lesions In Genomes), using denaturing HPLC or selective endonuclease digestion of selected PCR products is also applicable to the instant invention. See, McCallum, et al., (2000) *Nat. Biotechnol.* 18:455-457, herein incorporated by reference.

Mutations that impact gene expression or that interfere with the function (enhanced activity) of the encoded protein are well known in the art. Insertional mutations in gene exons usually result in null-mutants. Mutations in conserved residues are particularly effective in inhibiting the activity of the encoded protein. Conserved residues of plant ETO1 polypeptides suitable for mutagenesis with the goal to eliminate activity have been described. Such mutants can be isolated according to well-known procedures, and mutations in different ETO1 associated loci can be stacked by genetic crossing. See, for example, Gruis, et al., (2002) *Plant Cell* 14:2863-2882.

The invention encompasses additional methods for reducing or eliminating the activity of one or more ETO1 polypeptide. Examples of other methods for altering or mutating a genomic nucleotide sequence in a plant are known in the art and include, but are not limited to, the use of RNA:DNA vectors, RNA:DNA mutational vectors, RNA:DNA repair vectors, mixed-duplex oligonucleotides, self-complementary RNA:DNA oligonucleotides and recombinogenic oligonucleobases. Such vectors and methods of use are known in the art. See, for example, U.S. Pat. Nos. 5,565,350; 5,731,181; 5,756,325; 5,760,012; 5,795,972 and 5,871,984; each of which are herein incorporated by reference. See also, WO 1998/49350, WO 1999/07865, WO 1999/25821 and Beetham, et al., (1999) *Proc. Natl. Acad. Sci. USA* 96:8774-8778, each of which is herein incorporated by reference.

Transfection/Transformation of Cells

The method of transformation/transfection is not critical to the instant invention; various methods of transformation or transfection are currently available. As newer methods are available to transform crops or other host cells they may be directly applied.

Accordingly, a wide variety of methods have been developed to insert a DNA sequence into the genome of a host cell to obtain the transcription and/or translation of the sequence to effect phenotypic changes in the organism. Thus, any method which provides for effective transformation/transfection may be employed.

A. Plant Transformation

A DNA sequence coding for the desired polypeptide of the present invention, for example a cDNA or a genomic sequence encoding a full length protein, will be used to construct a recombinant expression cassette which can be introduced into the desired plant.

Isolated nucleic acid acids of the present invention can be introduced into plants according to techniques known in the art. Generally, recombinant expression cassettes as described above and suitable for transformation of plant cells are prepared. Techniques for transforming a wide variety of higher plant species are well known and described in the technical, scientific and patent literature. See, for example, Weising et al., (1988) *Ann. Rev. Genet.* 22:421-477. For example, the DNA construct may be introduced directly into the genomic DNA of the plant cell using techniques such as electroporation, polyethylene glycol (PEG), poration, particle bombardment, silicon fiber delivery or microinjection of plant cell protoplasts or embryogenic callus. See, e.g., Tomes, et al., Direct DNA Transfer into Intact Plant Cells Via Microprojectile Bombardment. pp. 197213 in Plant Cell, Tissue and Organ Culture, Fundamental Methods. eds. Gamborg and Phillips. Springer-Verlag Berlin Heidelberg New York, 1995. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616.

The introduction of DNA constructs using PEG precipitation is described in Paszkowski, et al., (1984) *Embo J.* 3:2717-2722. Electroporation techniques are described in Fromm, et al., (1985) *Proc. Natl. Acad. Sci. (USA)* 82:5824. Ballistic transformation techniques are described in Klein et al., (1987) *Nature* 327:70-73.

*Agrobacterium tumefaciens*-mediated transformation techniques are well described in the scientific literature. See, for example Horsch, et al., (1984) *Science* 233:496-498 and Fraley et al., (1983) *Proc. Natl. Acad. Sci. (USA)* 80:4803. Although *Agrobacterium* is useful primarily in dicots, certain monocots can be transformed by *Agrobacterium*. For instance, *Agrobacterium* transformation of maize is described in U.S. Pat. No. 5,550,318.

Other methods of transfection or transformation include (1) *Agrobacterium rhizogenes*-mediated transformation (see, e.g., Lichtenstein and Fuller In: Genetic Engineering, vol. 6, P W J Rigby, Ed., London, Academic Press, 1987; and Lichtenstein and Draper, In: DNA Cloning, Vol. II, D. M. Glover, Ed., Oxford, IRI Press, 1985), PCT Application Number PCT/US87/02512 (WO 1988/02405 published Apr. 7, 1988) describes the use of *A. rhizogenes* strain A4 and its Ri plasmid along with *A. tumefaciens* vectors pARC8 orpARC16 (2) liposome-mediated DNA uptake (see, e.g., Freeman, et al., (1984) *Plant Cell Physiol.* 25:1353), (3) the vortexing method (see, e.g., Kindle, (1990) *Proc. Natl. Acad. Sci., (USA)* 87:1228).

DNA can also be introduced into plants by direct DNA transfer into pollen as described by Zhou, et al., (1983) *Methods in Enzymology* 101:433; Hess, (1987) *Intern Rev. Cytol.* 107:367; Luo, et al., (1988) *Plant Mol. Biol. Reporter* 6:165. Expression of polypeptide coding genes can be obtained by injection of the DNA into reproductive organs of a plant as described by Pena, et al., (1987) *Nature* 325:274.

DNA can also be injected directly into the cells of immature embryos and the rehydration of desiccated embryos as described by Neuhaus, et al., (1987) *Theor. Appl. Genet.* 75:30 and Benbrook, et al., in Proceedings Bio Expo 1986, Butterworth, Stoneham, Mass., pp. 27-54 (1986). A variety of plant viruses that can be employed as vectors are known in the art and include cauliflower mosaic virus (CaMV), geminivirus, brome mosaic virus, and tobacco mosaic virus.

B. Transfection of Prokaryotes, Lower Eukaryotes, and Animal Cells

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics and micro-injection of the DNA directly into the cells. The transfected cells are cultured by means well known in the art. Kuchler, Biochemical Methods in Cell Culture and Virology, Dowden, Hutchinson and Ross, Inc. (1977).

Synthesis of Proteins

The proteins of the present invention can be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3-284 in The Peptides: Analysis, Synthesis, Biology, Vol. 2: Special Methods in Peptide Synthesis, Part A.; Merrifield, et al., (1963) *J. Am. Chem. Soc.* 85:2149-2156 and Stewart, et al., Solid Phase Peptide Synthesis, 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide) are known to those of skill.

Purification of Proteins

The proteins of the present invention may be purified by standard techniques well known to those of skill in the art. Recombinantly produced proteins of the present invention can be directly expressed or expressed as a fusion protein. The recombinant protein is purified by a combination of cell lysis (e.g., sonication, French press) and affinity chromatography. For fusion products, subsequent digestion of the fusion protein with an appropriate proteolytic enzyme releases the desired recombinant protein.

The proteins of this invention, recombinant or synthetic, may be purified to substantial purity by standard techniques well known in the art, including detergent solubilization, selective precipitation with such substances as ammonium sulfate, column chromatography, immunopurification methods and others. See, for instance, Scopes, Protein Purification: Principles and Practice, Springer-Verlag: New York (1982); Deutscher, Guide to Protein Purification, Academic Press (1990). For example, antibodies may be raised to the proteins as described herein. Purification from *E. coli* can be achieved following procedures described in U.S. Pat. No. 4,511,503. The protein may then be isolated from cells expressing the protein and further purified by standard protein chemistry techniques as described herein. Detection of the expressed protein is achieved by methods known in the art and include, for example, radioimmunoassays, Western blotting techniques or immunoprecipitation.

Transgenic Plant Regeneration

Transformed plant cells which are derived by any of the above transformation techniques can be cultured to regenerate a whole plant which possesses the transformed genotype. Such regeneration techniques often rely on manipulation of certain phytohormones in a tissue culture growth medium. For transformation and regeneration of maize see, Gordon-Kamm, et al., (1990) *The Plant Cell* 2:603-618.

Plants cells transformed with a plant expression vector can be regenerated, e.g., from single cells, callus tissue or leaf discs according to standard plant tissue culture techniques. It is well known in the art that various cells, tissues and organs from almost any plant can be successfully cultured to regenerate an entire plant. Plant regeneration from cultured protoplasts is described in Evans, et al., Protoplasts Isolation and Culture, Handbook of Plant Cell Culture, Macmillan Publishing Company, New York, pp. 124-176 (1983) and Binding, Regeneration of Plants, Plant Protoplasts, CRC Press, Boca Raton, pp. 21-73 (1985).

The regeneration of plants containing the foreign gene introduced by *Agrobacterium* from leaf explants can be achieved as described by Horsch, et al., (1985) *Science* 227: 1229-1231. In this procedure, transformants are grown in the presence of a selection agent and in a medium that induces the regeneration of shoots in the plant species being transformed as described by Fraley, et al., (1983) *Proc. Natl. Acad. Sci. USA* 80:4803. This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Kleen, et al., (1987) *Ann. Rev. of Plant Phys.* 38:467-486. The regeneration of plants from either single plant protoplasts or various explants is well known in the art. See, for example, Methods for Plant Molecular Biology, A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil. For maize cell culture and regeneration see generally, The Maize Handbook, Freeling and Walbot, Eds., Springer, New York (1994); Corn and Corn Improvement, 3rd edition, Sprague and Dudley Eds., American Society of Agronomy, Madison, Wis. (1988).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed. In vegetatively propagated crops, mature transgenic plants can be propagated by the taking of cuttings or by tissue culture techniques to produce multiple identical plants.

Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences. Transgenic plants expressing the selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, nontransgenic). Back-crossing to a parental plant and out-crossing with a non-transgenic plant are also contemplated.

Modulation of Polypeptide Levels and/or Composition

The present invention further provides a method for modulating (i.e., increasing or decreasing) the concentration or ratio of the polypeptides of the present invention in a plant or part thereof. Modulation can be effected by increasing or decreasing the concentration and/or the ratio of the polypeptides of the present invention in a plant.

The method comprises introducing into a plant cell a recombinant expression cassette comprising a polynucleotide of the present invention as described above to obtain a transformed plant cell, culturing the transformed plant cell under plant cell growing conditions and inducing or repressing expression of a polynucleotide of the present invention in the plant for a time sufficient to modulate concentration and/or the ratios of the polypeptides in the plant or plant part.

In some embodiments, the concentration and/or ratios of polypeptides of the present invention in a plant may be modulated by altering, in vivo or in vitro, the promoter of a gene to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling, et al., PCT Patent Application Number PCT/US93/03868. And in some embodiments, an isolated nucleic acid (e.g., a vector) comprising a promoter sequence is transfected into a plant cell.

Subsequently, a plant cell comprising the promoter operably linked to a polynucleotide of the present invention is selected for by means known to those of skill in the art, such as, but not limited to, Southern blot, DNA sequencing or PCR analysis using primers specific to the promoter and to the gene and detecting amplicons produced therefrom. A plant or plant part altered or modified by the foregoing embodiments is grown under plant forming conditions for a time sufficient to modulate the concentration and/or ratios of polypeptides of the present invention in the plant. Plant forming conditions are well known in the art and discussed briefly, supra.

In general, concentration or the ratios of the polypeptides is increased or decreased by at least 5%, 10%, 20%, 30%, 40%, 50%, 60%, 70%, 80% or 90% relative to a native control plant, plant part, or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds which activate expression from these promoters are well known in the art. In preferred embodiments, the polypeptides of the present invention are modulated in monocots, particularly maize.

Molecular Markers

The present invention provides a method of genotyping a plant comprising a polynucleotide of the present invention. Optionally, the plant is a monocot, such as maize or sorghum. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning and the study of quantitative inheritance. See, e.g., Clark, Ed., Plant Molecular Biology: A Laboratory Manual. Berlin, Springer Verlag, 1997, Chapter 7. For molecular marker methods, see generally, "The DNA Revolution" in: Paterson, Genome Mapping in Plants (Austin, Tex., Academic Press/R. G. Landis Company, 1996) pp. 7-21.

The particular method of genotyping in the present invention may employ any number of molecular marker analytic techniques such as, but not limited to, restriction fragment length polymorphisms (RFLPs). RFLPs are the product of allelic differences between DNA restriction fragments resulting from nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed.

Differences in fragment size among alleles represent an RFLP. Thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2 or 1 cM of a gene of the present invention.

In the present invention, the nucleic acid probes employed for molecular marker mapping of plant nuclear genomes selectively hybridize, under selective hybridization conditions, to a gene encoding a polynucleotide of the present invention. In preferred embodiments, the probes are selected from polynucleotides of the present invention.

Typically, these probes are cDNA probes or restriction-enzyme treated (e.g., Pst I) genomic clones. The length of the probes is discussed in greater detail, supra, but are typically at least 15 bases in length, more preferably at least 20, 25, 30, 35, 40 or 50 bases in length. Generally, however, the probes are less than about 1 kilobase in length. Preferably, the probes are single copy probes that hybridize to a unique locus in a haploid chromosome complement. Some exemplary restriction enzymes employed in RFLP mapping are EcoRI, EcoRv and SstI. As used herein the term "restriction enzyme" includes reference to a composition that recognizes and alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present of said genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single stranded conformation analysis (SSCA); 2) denaturing gradient gel electrophoresis (DGGE); 3) RNase protection assays; 4) allele-specific oligonucleotides (ASOs); 5) the use of proteins which recognize nucleotide mismatches, such as the E. coli mutS protein and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Thus, the present invention further provides a method of genotyping comprising the steps of contacting, under stringent hybridization conditions, a sample suspected of comprising a polynucleotide of the present invention with a nucleic acid probe. Generally, the sample is a plant sample; preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, (1987) Nucleic Acids Res. 15:8125) and the 7-methylguanosine cap structure (Drummond, et al., (1985) Nucleic Acids Res. 13:7375). Negative elements include stable intramolecular 5' UTR stem-loop structures (Muesing, et al., (1987) Cell 48:691) and AUG sequences or short open reading frames preceded by an appropriate AUG in the 5' UTR (Kozak, supra, Rao, et al., (1988) Mol. and Cell. Biol. 8:284). Accordingly, the present invention provides 5' and/or 3' untranslated regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host such as to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see, Devereaux, et al., (1984) Nucleic Acids Res. 12:387-395) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be full-length sequences. An exemplary number of sequences for statistical analysis can be at least 1, 5, 10, 20, 50 or 100.

Sequence Shuffling

The present invention provides methods for sequence shuffling using polynucleotides of the present invention, and compositions resulting therefrom. Sequence shuffling is described in PCT Application Publication Number WO 1997/20078. See also, Zhang, et al., (1997) Proc. Natl. Acad. Sci. USA 94:4504-4509. Generally, sequence shuffling provides a means for generating libraries of polynucleotides having a desired characteristic which can be selected or screened for. Libraries of recombinant polynucleotides are generated from a population of related sequence polynucleotides which comprise sequence regions which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation or other expression property of a gene or transgene, a replicative element, a protein-binding element, or the like, such as any feature which confers a selectable or detectable property. In some embodiments, the selected characteristic will be a decreased Km and/or increased KCat over the wild-type protein as provided herein. In other embodiments, a protein or polynucleotide generated from sequence shuffling will have a ligand binding affinity greater than the non-shuffled wild-type polynucleotide. The increase in such properties can be at least 110%, 120%, 130%, 140% or at least 150% of the wild-type value.

Generic and Consensus Sequences

Polynucleotides and polypeptides of the present invention further include those having: (a) a generic sequence of at least two homologous polynucleotides or polypeptides, respectively, of the present invention and (b) a consensus sequence of at least three homologous polynucleotides or polypeptides, respectively, of the present invention. The generic sequence of the present invention comprises each species of polypeptide or polynucleotide embraced by the generic polypeptide or polynucleotide sequence, respectively. The individual species encompassed by a polynucleotide having an amino acid or nucleic acid consensus sequence can be used to generate antibodies or produce nucleic acid probes or primers to screen for homologs in other species, genera, families, orders, classes, phyla, or kingdoms. For example, a polynucleotide having a consensus sequence from a gene family of Zea mays can be used to generate antibody or nucleic acid probes or primers to other Gramineae species such as wheat, rice, or sorghum.

Alternatively, a polynucleotide having a consensus sequence generated from orthologous genes can be used to identify or isolate orthologs of other taxa. Typically, a polynucleotide having a consensus sequence will be at least 25, 30, or 40 amino acids in length, or 20, 30, 40, 50, 100 or 150 nucleotides in length. As those of skill in the art are aware, a conservative amino acid substitution can be used for amino acids which differ amongst aligned sequence but are from the same conservative substitution group as discussed above. Optionally, no more than 1 or 2 conservative amino acids are substituted for each 10 amino acid length of consensus sequence.

Similar sequences used for generation of a consensus or generic sequence include any number and combination of allelic variants of the same gene, orthologous or paralogous sequences as provided herein. Optionally, similar sequences used in generating a consensus or generic sequence are identified using the BLAST algorithm's smallest sum probability (P(N)). Various suppliers of sequence-analysis software are listed in chapter 7 of Current Protocols in Molecular Biology, Ausubel, et al., Eds., Current Protocols, a joint venture between Greene Publishing Associates, Inc. and John Wiley & Sons, Inc. (Supplement 30).

A polynucleotide sequence is considered similar to a reference sequence if the smallest sum probability in a comparison of the test nucleic acid to the reference nucleic acid is less than about 0.1, more preferably less than about 0.01, or 0.001 and most preferably less than about 0.0001 or 0.00001. Similar polynucleotides can be aligned and a consensus or generic sequence generated using multiple sequence alignment software available from a number of commercial suppliers, such as the Genetics Computer Group's (Madison, Wis.) PILEUP software, Vector NTI's (North Bethesda, Md.) ALIGNX or Genecode's (Ann Arbor, Mich.) SEQUENCHER. Conveniently, default parameters of such software can be used to generate consensus or generic sequences.

Machine Applications

The present invention provides machines, articles of manufacture, and processes for identifying, modeling or analyzing the polynucleotides and polypeptides of the present invention. Identification methods permit identification of homologues of the polynucleotides or polypeptides of the present invention while modeling and analysis methods permit recognition of structural or functional features of interest.

A. Machines: Data Processing Systems

In one embodiment, the present invention provides a machine having: 1) a memory comprising data representing at least one genetic sequence, 2) a genetic identification, analysis, or modeling program with access to the data, 3) a data processor which executes instructions according to the program using the genetic sequence or a subsequence thereof and 4) an output for storing or displaying the results of the data processing.

The machine of the present invention is a data processing system, typically a digital computer. The term "computer" includes one or several desktop or portable computers, computer workstations, servers (including intranet or internet servers), mainframes and any integrated system comprising any of the above irrespective of whether the processing, memory, input or output of the computer is remote or local, as well as any networking interconnecting the modules of the computer. Data processing can thus be remote or distributed amongst several processors at one or multiple sites. The data processing system comprises a data processor, such as a central processing unit (CPU), which executes instructions according to an application program. As used herein, machines, articles of manufacture and processes are exclusive of the machines, manufactures, and processes employed by the United States Patent and Trademark Office or the European Patent Office when data representing the sequence of a polypeptide or polynucleotide of the present invention is used for patentability searches.

The machine of the present invention includes a memory comprising data representing at least one genetic sequence. As used herein, "genetic sequence" refers to the primary sequence (i.e., amino acid or nucleotide sequence) of a polynucleotide or polypeptide of the present invention. The genetic sequence can represent a partial sequence from a full-length protein, genomic DNA or full-length cDNA/mRNA. Nucleic acids or proteins comprising a genetic sequence that is identified, analyzed or modeled according to the present invention can be cloned or synthesized.

As those of skill in the art will be aware, the form of memory of a machine of the present invention, or the particular embodiment of the computer readable medium, are not critical elements of the invention and can take a variety of forms. The memory of such a machine includes, but is not limited to, ROM or RAM or computer readable media such as, but not limited to, magnetic media such as computer disks or hard drives or media such as CD-ROMs, DVDs, and the like. The memory comprising the data representing the genetic sequence includes main memory, a register and a cache. In some embodiments the data processing system stores the data representing the genetic sequence in memory while processing the data and wherein successive portions of the data are copied sequentially into at least one register of the data processor for processing. Thus, the genetic sequence stored in memory can be a genetic sequence created during computer runtime or stored beforehand. The machine of the present invention includes a genetic identification, analysis or modeling program (discussed below) with access to the data representing the genetic sequence. The program can be implemented in software or hardware.

The present invention further contemplates that the machine of the present invention will reference, directly or indirectly, a utility or function for the polynucleotide or polypeptide of the present invention. For example, the utility/function can be directly referenced as a data element in the machine and accessible by the program. Alternatively, the utility/function of the genetic can be indirectly referenced to an electronic or written record. The function or utility of the genetic sequence can be a function or utility for the genetic sequence, or the data representing the sequence (i.e., the genetic sequence data).

Exemplary function or utilities for the genetic sequence include: 1) its name (per International Union of Biochemistry and Molecular Biology rules of nomenclature) or the function of the enzyme or protein represented by the genetic sequence, 2) the metabolic pathway that the protein represented by the genetic sequence participates in, 3) the substrate or product or structural role of the protein represented by the genetic sequence or 4) the phenotype (e.g., an agronomic or pharmacological trait) affected by modulating expression or activity of the protein represented by the genetic sequence.

The machine of the present invention also includes an output for displaying, printing or recording the results of the identification, analysis or modeling performed using a genetic sequence of the present invention. Exemplary outputs include monitors, printers or various electronic storage mechanisms (e.g., floppy disks, hard drives, main memory) which can be used to display the results or employed as a means to input the stored data into a subsequent application or device.

In some embodiments, data representing a genetic sequence of the present invention is a data element within a data structure. The data structure may be defined by the computer programs that define the processes of identification, modeling or analysis (see below) or it may be defined by the programming of separate data storage and retrieval programs subroutines or systems. Thus, the present invention provides a memory for storing a data structure that can be accessed by a computer programmed to implement a process for identification, analysis or modeling of a genetic sequence. The data structure, stored within memory, is associated with the data representing the genetic sequence and reflects the underlying organization and structure of the genetic sequence to facilitate program access to data elements corresponding to logical sub-components of the genetic sequence. The data structure enables the genetic sequence to be identified, analyzed or modeled. The underlying order and structure of a genetic sequence is data representing the higher order organization of the primary sequence. Such higher order structures affect transcription, translation, enzyme kinetics or reflects structural domains or motifs.

Exemplary logical sub-components which constitute the higher order organization of the genetic sequence include but are not limited to: restriction enzyme sites, endopeptidase sites, major grooves, minor grooves, beta-sheets, alpha helices, open reading frames (ORFS), 5' untranslated regions (UTRs), 3' UTRs, ribosome binding sites, glycosylation sites, signal peptide domains, intron-exon junctions, poly-A tails, transcription initiation sites, translation start sites, translation termination sites, methylation sites, zinc finger domains, modified amino acid sites, preproprotein-proprotein junctions, proprotein-protein junctions, transit peptide domains, single nucleotide polymorphisms (SNPs), simple sequence repeats (SSRs), restriction fragment length polymorphisms (RFLPs), insertion elements, transmembrane spanning regions and stem-loop structures.

In another embodiment, the present invention provides a data processing system comprising at least one data structure in memory where the data structure supports the accession of data representing a genetic sequence of the present invention. The system also comprises at least one genetic identification, analysis or modeling program which directs the execution of instructions by the system using the genetic sequence data to identify, analyze or model at least one data element which is a logical sub-component of the genetic sequence. An output for the processing results is also provided.

B. Articles of Manufacture: Computer Readable Media

In one embodiment, the present invention provides a data structure in a computer readable medium that contains data representing a genetic sequence of the present invention. The data structure is organized to reflect the logical structuring of the genetic sequence, so that the sequence can be analyzed by software programs capable of accessing the data structure. In particular, the data structures of the present invention organize the genetic sequences of the present invention in a manner which allows software tools to perform an identification, analysis or modeling using logical elements of each genetic sequence.

In a further embodiment, the present invention provides a machine-readable media containing a computer program and genetic sequence data. The program provides instructions sufficient to implement a process for effecting the identification, analysis or modeling of the genetic sequence data. The media also includes a data structure reflecting the underlying organization and structure of the data to facilitate program access to data elements corresponding to logical sub-components of the genetic sequence, the data structure being inherent in the program and in the way in which the program organizes and accesses the data.

An example of a data structure resembles a layered hash table, where in one dimension the base content of the sequence is represented by a string of elements A, T, C, G and N. The direction from the 5' end to the 3' end is reflected by the order from the position 0 to the position of the length of the string minus one. Such a string, corresponding to a nucleotide sequence of interest, has a certain number of substrings, each of which is delimited by the string position of its 5' end and the string position of its 3' end within the parent string. In a second dimension, each substring is associated with or pointed to one or multiple attribute fields. Such attribute fields contain annotations to the region on the nucleotide sequence represented by the substring.

For example, a sequence under investigation is 520 bases long and represented by a string named SeqTarget. There is a minor groove in the 5' upstream non-coding region from position 12 to 38, which is identified as a binding site for an enhancer protein HM-A, which in turn will increase the transcription of the gene represented by SeqTarget. Here, the substring is represented as (12, 38) and has the following attributes: [upstream uncoded], [minor groove], [HM-A binding] and [increase transcription upon binding by HM-A]. Similarly, other types of information can be stored and structured in this manner, such as information related to the whole sequence, e.g., whether the sequence is a full length viral gene, a mammalian house keeping gene or an EST from clone X, information related to the 3' down stream non-coding region, e.g., hair pin structure and information related to various domains of the coding region, e.g., Zinc finger.

This data structure is an open structure and is robust enough to accommodate newly generated data and acquired knowledge. Such a structure is also a flexible structure. It can be trimmed down to a 1-D string to facilitate data mining and analysis steps, such as clustering, repeat-masking and HMM analysis. Meanwhile, such a data structure also can extend the associated attributes into multiple dimensions. Pointers can be established among the dimensioned attributes when needed to facilitate data management and processing in a comprehensive genomics knowledge base. Furthermore, such a data structure is object-oriented. Polymorphism can be represented by a family or class of sequence objects, each of which has an internal structure as discussed above. The common traits are abstracted and assigned to the parent object, whereas each child object represents a specific variant of the family or class. Such a data structure allows data to be efficiently retrieved, updated and integrated by the software applications associated with the sequence database and/or knowledge base.

C. Processes: Identification, Analysis, or Modeling

The present invention also provides a process of identifying, analyzing, or modeling data representing a genetic sequence of the present invention. The process comprises: 1) providing a machine having a hardware or software implemented genetic sequence identification, modeling, or analysis program with data representing a genetic sequence, 2) executing the program while granting it access to the genetic sequence data and 3) displaying or outputting the results of the identification, analysis, or modeling. Data structures made by the processes of the present invention and embodied within a computer readable medium are also provided herein.

A further process of the present invention comprises providing a memory embodied with data representing a genetic sequence and developing within the memory a data structure associated with the data and reflecting the underlying organization and structure of the data to facilitate program access to data elements corresponding to logical subcomponents of the sequence. A computer is programmed with a program containing instructions sufficient to implement the process for effecting the identification, analysis or modeling of the genetic sequence and the program is executed on the computer while granting the program access to the data and to the data structure within the memory. The program results are outputted.

Identification, analysis, and modeling programs are well known in the art and available commercially. The program typically has at least one application to: 1) identify the structural role or enzymatic function of the gene which the genetic sequence encodes or is translated from, 2) analyzes and identifies higher order structures within the genetic sequence or 3) model the physico-chemical properties of a genetic sequence of the present invention in a particular environment.

Included amongst the modeling/analysis tools are methods to: 1) recognize overlapping sequences (e.g., from a sequencing project) with a polynucleotide of the present invention and create an alignment called a "contig"; 2) identify restriction enzyme sites of a polynucleotide of the present invention; 3) identify the products of a TI ribonuclease digestion of a polynucleotide of the present invention; 4) identify PCR primers with minimal self-complementarity; 5) compute pairwise distances between sequences in an alignment, reconstruct phylogentic trees using distance methods, and calculate the degree of divergence of two protein coding regions; 6) identify patterns such as coding regions, terminators, repeats, and other consensus patterns in polynucleotides of the present invention; 7) identify RNA secondary structure; 8) identify sequence motifs, isoelectric point, secondary structure, hydrophobicity and antigenicity in polypeptides of the present invention; 9) translate polynucleotides of the present invention and backtranslate polypeptides of the present invention and 10) compare two protein or nucleic acid sequences and identifying points of similarity or dissimilarity between them.

Identification of the function/utility of a genetic sequence is typically achieved by comparative analysis to a gene/protein database and establishing the genetic sequence as a candidate homologue (i.e., ortholog or paralog) of a gene/protein of known function/utility.

A candidate homologue has statistically significant probability of having the same biological function (e.g., catalyzes the same reaction, binds to homologous proteins/nucleic acids, has a similar structural role) as the reference sequence to which it is compared. Sequence identity/similarity is frequently employed as a criterion to identify candidate homologues. In the same vein, genetic sequences of the present invention have utility in identifying homologs in animals or other plant species, particularly those in the family Gramineae such as, but not limited to, sorghum, wheat or rice. Function is frequently established on the basis of sequence identity/similarity. Exemplary sequence comparison systems are provided for in sequence analysis software such as those provided by the Genetics Computer Group (Madison, Wis.) or InforMax</RTI The present invention further provides methods for detecting a polynucleotide of the present invention in a nucleic acid sample suspected of containing a polynucleotide of the present invention, such as a plant cell lysate, particularly a lysate of maize. In some embodiments, a gene of the present invention or portion thereof can be amplified prior to the step of contacting the nucleic acid sample with a polynucleotide of the present invention. The nucleic acid sample is contacted with the polynucleotide to form a hybridization complex. The polynucleotide hybridizes under stringent conditions to a gene encoding a polypeptide of the present invention. Formation of the hybridization complex is used to detect a gene encoding a polypeptide of the present invention in the nucleic acid sample. Those of skill will appreciate that an isolated nucleic acid comprising a polynucleotide of the present invention should lack cross-hybridizing sequences in common with non-target genes that would yield a false positive result.

Detection of the hybridization complex can be achieved using any number of well known methods. For example, the nucleic acid sample, or a portion thereof, may be assayed by hybridization formats including but not limited to, solution phase, solid phase, mixed phase, or in situ hybridization assays. Briefly, in solution (or liquid) phase hybridizations, both the target nucleic acid and the probe or primer are free to interact in the reaction mixture. In solid phase hybridization assays, probes or primers are typically linked to a solid support where they are available for hybridization with target nucleic in solution. In mixed phase, nucleic acid intermediates in solution hybridize to target nucleic acids in solution as well as to a nucleic acid linked to a solid support. In in situ hybridization, the target nucleic acid is liberated from its cellular surroundings in such as to be available for hybridization within the cell while preserving the cellular morphology for subsequent interpretation and analysis. The following articles provide an overview of the various hybridization assay formats: Singer, et al., (1986) *Biotechniques* 4(3):230-250; Haase, et al., Methods in Virology, Vol. VII, pp. 189-226 (1984); Wilkinson, The theory and practice of in situ hybridization in: In situ Hybridization, Wilkinson, Ed., IRL Press, Oxford University Press, Oxford; and Nucleic Acid Hybridization: A Practical Approach, Hames and Higgins, Eds., IRL Press (1987).

Nucleic Acid Labels and Detection Methods

The means by which nucleic acids of the present invention are labeled is not a critical aspect of the present invention and can be accomplished by any number of methods currently known or later developed. Detectable labels suitable for use in the present invention include any composition detectable by spectroscopic, radioisotopic, photochemical, biochemical, immunochemical, electrical, optical or chemical means.

Useful labels in the present invention include biotin for staining with labeled streptavidin conjugate, magnetic beads, fluorescent dyes (e.g., fluorescein, Texas red, rhodamine, green fluorescent protein and the like), radiolabels (e.g., 3H, 125I, 35S, I4C or 32P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads.

Nucleic acids of the present invention can be labeled by any one of several methods typically used to detect the presence of hybridized nucleic acids. One common method of detection is the use of autoradiography using probes labeled with 3H, 125I, 35S, I4C or 32P, or the like. The choice of radioactive isotope depends on research preferences due to ease of synthesis, stability, and half lives of the selected isotopes. Other labels include ligands which bind to antibodies labeled with fluorophores, chemiluminescent agents and enzymes. Alternatively, probes can be conjugated directly with labels such as fluorophores, chemiluminescent agents or enzymes. The choice of label depends on sensitivity required, ease of conjugation with the probe, stability requirements and available instrumentation. Labeling the nucleic acids of the present invention is readily achieved such as by the use of labeled PCR primers.

In some embodiments, the label is simultaneously incorporated during the amplification step in the preparation of the nucleic acids. Thus, for example, polymerase chain reaction (PCR) with labeled primers or labeled nucleotides will provide a labeled amplification product. In another embodiment, transcription amplification using a labeled nucleotide (e.g., fluorescein-labeled UTP and/or CTP) incorporates a label into the transcribed nucleic acids.

Non-radioactive probes are often labeled by indirect means. For example, a ligand molecule is covalently bound to the probe. The ligand then binds to an anti-ligand molecule which is either inherently detectable or covalently bound to a detectable signal system, such as an enzyme, a fluorophore or a chemiluminescent compound. Enzymes of interest as labels will primarily be hydrolases, such as phosphatases, esterases and glycosidases or oxidoreductases, particularly peroxidases. Fluorescent compounds include fluorescein and its derivatives, rhodamine and its derivatives, dansyl, umbelliferone, etc. Chemiluminescers include luciferin and 2,3-dihydrophthalazinediones, e.g., luminol.

Ligands and anti-ligands may be varied widely. Where a ligand has a natural anti-ligand, namely ligands such as biotin, thyroxine and cortisol, it can be used in conjunction with its labeled, naturally occurring anti-ligands. Alternatively, any haptenic or antigenic compound can be used in combination with an antibody. Probes can also be labeled by direct conjugation with a label. For example, cloned DNA probes have been coupled directly to horseradish peroxidase or alkaline phosphatase.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate and colorimetric labels are detected by simply visualizing the colored label.

Antibodies to Proteins

Antibodies can be raised to a protein of the present invention, including individual, allelic, strain, or species variants, and fragments thereof, both in their naturally occurring (full-length) forms and in recombinant forms. Additionally, antibodies are raised to these proteins in either their native configurations or in non-native configurations. Many methods of making antibodies are known to persons of skill. A variety of analytic methods are available to generate a hydrophilicity profile of a protein of the present invention. Such methods can be used to guide the artisan in the selection of peptides of the present invention for use in the generation or selection of antibodies which are specifically reactive, under immunogenic conditions, to a protein of the present invention. See, e.g., Janin, (1979) *Nature* 277:491-492; Wolfenden, et al., (1981) *Biochemistry* 20:849-855; Kyte and Doolite, (1982) *J. Mol. Biol.* 157:105-132; Rose, et al., (1985) *Science* 229: 834838. The following discussion is presented as a general overview of the techniques available; however, one of skill will recognize that many variations upon the following methods are known.

A number of immunogens are used to produce antibodies specifically reactive with a protein of the present invention. An isolated recombinant, synthetic or native polynucleotide of the present invention are the preferred antigens for the production of monoclonal or polyclonal antibodies. Polypeptides of the present invention are optionally denatured, and optionally reduced, prior to formation of antibodies for screening expression libraries or other assays in which a putative protein of the present invention is expressed or denatured in a non-native secondary, tertiary, or quarternary structure.

The protein of the present invention is then injected into an animal capable of producing antibodies. Either monoclonal or polyclonal antibodies can be generated for subsequent use in immunoassays to measure the presence and quantity of the protein of the present invention. Methods of producing polyclonal antibodies are known to those of skill in the art. In brief, an antigen, preferably a purified protein, a protein coupled to an appropriate carrier (e.g., GST, keyhole limpet hemanocyanin, etc.), or a protein incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the protein of interest. When appropriately high titers of antibody to the immunogen are obtained, blood is collected from the animal and antisera are prepared. Further fractionation of the antisera to enrich for antibodies reactive to the protein is performed where desired (See, e.g., Coligan, Current Protocols in Immunology, Wiley/Greene, NY (1991) and Harlow and Lane, Antibodies: A Laboratory Manual, Cold Spring Harbor Press, NY (1989)).

Antibodies, including binding fragments and single chain recombinant versions thereof, against predetermined fragments of a protein of the present invention are raised by immunizing animals, e.g., with conjugates of the fragments with carrier proteins as described above. Typically, the immunogen of interest is a protein of at least about 5 amino acids, more typically the protein is 10 amino acids in length, preferably, 15 amino acids in length and more preferably the protein is 20 amino acids in length or greater. The peptides are typically coupled to a carrier protein (e.g., as a fusion protein) or are recombinantly expressed in an immunization vector. Antigenic determinants on peptides to which antibodies bind are typically 3 to 10 amino acids in length.

Monoclonal antibodies are prepared from hybrid cells secreting the desired antibody. Monoclonals antibodies are screened for binding to a protein from which the antigen was derived. Specific monoclonal and polyclonal antibodies will usually have an antibody binding site with an affinity constant for its cognate monovalent antigen at least between 106-107, usually at least 108, preferably at least 109, more preferably at least 101 and most preferably at least 101 liters/mole.

In some instances, it is desirable to prepare monoclonal antibodies from various mammalian hosts, such as mice, rodents, primates, humans, etc. Description of techniques for preparing such monoclonal antibodies are found in, e.g., Basic and Clinical Immunology, 4th ed., Stites et al., Eds., Lange Medical Publications, Los Altos, Calif., and references cited therein; Harlow and Lane, Supra; Goding, Monoclonal Antibodies: Principles and Practice, 2nd ed., Academic Press, New York, N.Y. (1986); and Kohler and Milstein, (1975) *Nature* 256:495-497. Summarized briefly, this method proceeds by injecting an animal with an antigen comprising a protein of the present invention. The animal is then sacrificed and cells taken from its spleen, which are fused with myeloma cells. The result is a hybrid cell or "hybridoma" that is capable of reproducing in vitro.

The population of hybridomas is then screened to isolate individual clones, each of which secrete a single antibody species to the antigen. In this manner, the individual antibody species obtained are the products of immortalized and cloned single B cells from the immune animal generated in response to a specific site recognized on the antigenic substance.

Other suitable techniques involve selection of libraries of recombinant antibodies in phage or similar vectors (see, e.g., Huse, et al., (1989) *Science* 246:1275-1281 and Ward, et al., (1989) *Nature* 341:544-546 and Vaughan, et al., (1996) *Nature Biotechnology* 14:309-314). Alternatively, high avidity human monoclonal antibodies can be obtained from transgenic mice comprising fragments of the unrearranged human heavy and light chain Ig loci (i.e., mini locus transgenic mice). Fishwild, et al., (1996) *Nature Bio Tech.* 14:845-851. Also, recombinant immunoglobulins may be produced. See, Cabilly, U.S. Pat. No. 4,816,567 and Queen et al., (1989) *Proc. Nat'l Acad. Sci.* 86:10029-10033.

The antibodies of this invention are also used for affinity chromatography in isolating proteins of the present invention. Columns are prepared, e.g., with the antibodies linked to a solid support, e.g., particles, such as agarose, SEPHADEX, or the like, where a cell lysate is passed through the column, washed and treated with increasing concentrations of a mild denaturant, whereby purified protein are released.

The antibodies can be used to screen expression libraries for particular expression products such as normal or abnormal protein. Usually the antibodies in such a procedure are labeled with a moiety allowing easy detection of presence of antigen by antibody binding. Antibodies raised against a protein of the present invention can also be used to raise anti-idiotypic antibodies. These are useful for detecting or diagnosing various pathological conditions related to the presence of the respective antigens.

Frequently, the proteins and antibodies of the present invention will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like.

Plants exhibiting an altered ethylene-dependent phenotype as compared with wild-type plants can be selected among other methods, by visual observation. For example, an altered ethylene-dependent phenotype may be detected by utilization of the "triple response." The "triple response" consists of three distinct morphological changes in dark-grown seedlings upon exposure to ethylene: inhibition of hypocotyl and root elongation, radial swelling of the stem and exaggeration of the apical hook. Thus, a triple response displayed in the presence of ethylene inhibitors would indicate one type of altered ethylene-dependent phenotype. Ethylene affects a vast array of agriculturally important plant processes, including fruit ripening, flower and leaf senescence and leaf abscission. The ability to control the sensitivity of plants to ethylene could thus significantly improve the quality and longevity of many crops. The invention includes plants produced by the method of the invention, as well as plant tissue and seeds.

"Stacking" of Constructs and Traits

In certain embodiments, the nucleic acid sequences of the present invention can be used in combination ("stacked") with other polynucleotide sequences of interest in order to create plants with a desired phenotype. The polynucleotides of the present invention may be stacked with any gene or combination of genes, and the combinations generated can include multiple copies of any one or more of the polynucleotides of interest. The desired combination may affect one or more traits; that is, certain combinations may be created for modulation of gene expression affecting ACC synthase activity and/or ethylene production. Other combinations may be designed to produce plants with a variety of desired traits, including but not limited to traits desirable for animal feed such as high oil genes (e.g., U.S. Pat. No. 6,232,529); balanced amino acids (e.g., hordothionins (U.S. Pat. Nos. 5,990,389; 5,885,801; 5,885,802 and 5,703,409); barley high lysine (Williamson, et al., (1987) *Eur. J. Biochem.* 165:99-106 and WO 1998/20122) and high methionine proteins (Pedersen, et al., (1986) *J. Biol. Chem.* 261:6279; Kirihara, et al., (1988) *Gene* 71:359 and Musumura, et al., (1989) *Plant Mol. Biol.* 12:123)); increased digestibility (e.g., modified storage proteins (U.S. patent application Ser. No. 10/053,410, filed Nov. 7, 2001) and thioredoxins (U.S. patent application Ser. No. 10/005,429, filed Dec. 3, 2001)), the disclosures of which are herein incorporated by reference. The polynucleotides of the present invention can also be stacked with traits desirable for insect, disease or herbicide resistance (e.g., *Bacillus thuringiensis* toxic proteins (U.S. Pat. Nos. 5,366,892; 5,747,450; 5,737,514; 5,723,756; 5,593,881; Geiser, et al., (1986) *Gene* 48:109); lectins (Van Damme, et al., (1994) *Plant Mol. Biol.* 24:825); fumonisin detoxification genes (U.S. Pat. No. 5,792,931); avirulence and disease resistance genes (Jones, et al., (1994) *Science* 266:789; Martin, et al., (1993) *Science* 262:1432; Mindrinos, et al., (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene) and glyphosate resistance (EPSPS gene)) and traits desirable for processing or process products such as high oil (e.g., U.S. Pat. No. 6,232,529); modified oils (e.g., fatty acid desaturase genes (U.S. Pat. No. 5,952,544; WO 1994/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert, et al., (1988) *J. Bacteriol.* 170:5837-5847) facilitate expression of polyhydroxyalkanoates (PHAs)), the disclosures of which are herein incorporated by reference. One could also combine the polynucleotides of the present invention with polynucleotides affecting agronomic traits such as male sterility (e.g., see, U.S. Pat. No. 5,583,210), stalk strength, flowering time, or transformation technology traits such as cell cycle regulation or gene targeting (e.g., WO 1999/61619; WO 2000/17364; WO 1999/25821), the disclosures of which are herein incorporated by reference.

These stacked combinations can be created by any method, including but not limited to cross breeding plants by any conventional or TopCross methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences of interest can be driven by the same promoter or by different promoters. In certain cases, it may be desirable to introduce a transformation cassette that will suppress the expression of a polynucleotide of interest. This may be accompanied by any combination of other suppression cassettes or over-expression cassettes to generate the desired combination of traits in the plant.

Use in Breeding Methods

The transformed plants of the invention may be used in a plant breeding program. The goal of plant breeding is to combine, in a single variety or hybrid, various desirable traits. For field crops, these traits may include, for example, resistance to diseases and insects, tolerance to heat and drought, reduced time to crop maturity, greater yield and better agronomic quality. With mechanical harvesting of many crops, uniformity of plant characteristics such as germination and stand establishment, growth rate, maturity and plant and ear height is desirable. Traditional plant breeding is an important tool in developing new and improved commercial crops. This invention encompasses methods for producing a maize plant by crossing a first parent maize plant with a second parent maize plant wherein one or both of the parent maize plants is a transformed plant displaying a staygreen phenotype, a sterility phenotype, a crowding resistance phenotype, or the like, as described herein.

Plant breeding techniques known in the art and used in a maize plant breeding program include, but are not limited to, recurrent selection, bulk selection, mass selection, backcrossing, pedigree breeding, open pollination breeding, restriction fragment length polymorphism enhanced selection, genetic marker enhanced selection, doubled haploids and transformation. Often combinations of these techniques are used.

The development of maize hybrids in a maize plant breeding program requires, in general, the development of homozygous inbred lines, the crossing of these lines and the evaluation of the crosses. There are many analytical methods available to evaluate the result of a cross. The oldest and most traditional method of analysis is the observation of phenotypic traits. Alternatively, the genotype of a plant can be examined.

A genetic trait which has been engineered into a particular maize plant using transformation techniques can be moved into another line using traditional breeding techniques that are well known in the plant breeding arts. For example, a backcrossing approach is commonly used to move a transgene from a transformed maize plant to an elite inbred line, and the resulting progeny would then comprise the transgene(s). Also, if an inbred line was used for the transformation, then the transgenic plants could be crossed to a different inbred in order to produce a transgenic hybrid maize plant. As used herein, "crossing" can refer to a simple X by Y cross, or the process of backcrossing, depending on the context.

The development of a maize hybrid in a maize plant breeding program involves three steps: (1) the selection of plants from various germplasm pools for initial breeding crosses; (2) the selfing of the selected plants from the breeding crosses for several generations to produce a series of inbred lines, which, while different from each other, breed true and are highly uniform and (3) crossing the selected inbred lines with different inbred lines to produce the hybrids. During the inbreeding process in maize, the vigor of the lines decreases. Vigor is restored when two different inbred lines are crossed to produce the hybrid. An important consequence of the homozygosity and homogeneity of the inbred lines is that the hybrid created by crossing a defined pair of inbreds will always be the same. Once the inbreds that give a superior hybrid have been identified, the hybrid seed can be reproduced indefinitely as long as the homogeneity of the inbred parents is maintained.

Transgenic plants of the present invention may be used to produce, e.g., a single cross hybrid, a three-way hybrid or a double cross hybrid. A single cross hybrid is produced when two inbred lines are crossed to produce the F1 progeny. A double cross hybrid is produced from four inbred lines crossed in pairs (A×B and C×D) and then the two F1 hybrids are crossed again (A×B)×(C×D). A three-way cross hybrid is produced from three inbred lines where two of the inbred lines are crossed (A×B) and then the resulting F1 hybrid is crossed with the third inbred (A×B)×C. Much of the hybrid vigor and uniformity exhibited by F1 hybrids is lost in the next generation (F2). Consequently, seed produced by hybrids is consumed rather than planted.

Antibodies

The polypeptides of the invention can be used to produce antibodies specific for the polypeptides of SEQ ID NO: 2, 4, 6, 8 or 10 and conservative variants thereof. Antibodies specific for, e.g., SEQ ID NO: 2, 4, 6, 8 or 10 and related variant polypeptides are useful, e.g., for screening and identification purposes, e.g., related to the activity, distribution and expression of ACC synthase.

Antibodies specific for the polypeptides of the invention can be generated by methods well known in the art. Such antibodies can include, but are not limited to, polyclonal, monoclonal, chimeric, humanized, single chain, Fab fragments and fragments produced by a Fab expression library.

Polypeptides do not require biological activity for antibody production. The full length polypeptide, subsequences, fragments or oligopeptides can be antigenic. Peptides used to induce specific antibodies typically have an amino acid sequence of at least about 10 amino acids and often at least 15 or 20 amino acids. Short stretches of a polypeptide, e.g., selected from among SEQ ID NO: 2, 4, 6, 8 or 10, can be fused with another protein, such as keyhole limpet hemocyanin and antibody produced against the chimeric molecule.

Numerous methods for producing polyclonal and monoclonal antibodies are known to those of skill in the art and can be adapted to produce antibodies specific for the polypeptides of the invention, e.g., corresponding to SEQ ID NO: 2, 4, 6, 8 or 10. See, e.g., Coligan (1991) Current Protocols in Immunology Wiley/Greene, NY; and Harlow and Lane (1989) Antibodies: A Laboratory Manual Cold Spring Harbor Press, NY; Stites et al. (eds.) Basic and Clinical Immunology (4th ed.) Lange Medical Publications, Los Altos, Calif., and references cited therein; Goding (1986) Monoclonal Antibodies: Principles and Practice (2d ed.) Academic Press, New York, N.Y.; Fundamental Immunology, e.g., 4th Edition (or later), W. E.

Paul (ed.), Raven Press, N.Y. (1998) and Kohler and Milstein, (1975) *Nature* 256:495-497. Other suitable techniques for antibody preparation include selection of libraries of recombinant antibodies in phage or similar vectors. See, Huse, et al., (1989) *Science* 246:1275-1281 and Ward, et al., (1989) *Nature* 341:544-546. Specific monoclonal and polyclonal antibodies and antisera will usually bind with a $K_D$ of at least about 0.1 µM, preferably at least about 0.01 µM or better and most typically and preferably, 0.001 µM or better.

Kits for Modulating Plant Stress Response

Certain embodiments of the invention can optionally be provided to a user as a kit. For example, a kit of the invention can contain one or more nucleic acid, polypeptide, antibody, diagnostic nucleic acid or polypeptide, e.g., antibody, probe set, e.g., as a cDNA microarray, one or more vector and/or cell line described herein. Most often, the kit is packaged in a suitable container. The kit typically further comprises one or more additional reagents, e.g., substrates, labels, primers, or the like for labeling expression products, tubes and/or other accessories, reagents for collecting samples, buffers, hybridization chambers, cover slips, etc. The kit optionally further comprises an instruction set or user manual detailing preferred methods of using the kit components for discovery or application of gene sets. When used according to the instructions, the kit can be used, e.g., for evaluating expression or polymorphisms in a plant sample, e.g., for evaluating ACC synthase, ethylene production, stress response potential, crowding resistance potential, sterility, etc. Alternatively, the kit can be used according to instructions for using at least one ACC synthase polynucleotide sequence to control ethylene production in a plant.

Other Nucleic Acid and Protein Assays

In the context of the invention, nucleic acids and/or proteins are manipulated according to well known molecular biology methods. Detailed protocols for numerous such procedures are described in, e.g., in Ausubel, et al., Current Protocols in Molecular Biology (supplemented through 2004) John Wiley & Sons, New York ("Ausubel"); Sambrook, et al., Molecular Cloning-A Laboratory Manual (2nd Ed.), Vol. 1 3, Cold Spring Harbor Laboratory, Cold Spring Harbor, N.Y., 1989 ("Sambrook") and Berger and Kimmel, Guide to Molecular Cloning Techniques, Methods in Enzymology volume 152 Academic Press, Inc., San Diego, Calif. ("Berger").

In addition to the above references, protocols for in vitro amplification techniques, such as the polymerase chain reaction (PCR), the ligase chain reaction (LCR), Qβ-replicase amplification and other RNA polymerase mediated techniques (e.g., NASBA), useful, e.g., for amplifying polynucleotides of the invention, are found in Mullis, et al., (1987) U.S. Pat. No. 4,683,202; PCR Protocols A Guide to Methods and Applications (Innis et al. eds) Academic Press Inc. San Diego, Calif. (1990) ("Innis"); Arnheim and Levinson, (1990) C&EN 36; The Journal Of NIH Research (1991) 3:81; Kwoh, et al., (1989) *Proc Natl Acad Sci USA* 86:1173; Guatelli, et al., (1990) *Proc Natl Acad Sci USA* 87:1874; Lomell, et al., (1989) *J. Clin. Chem.* 35:1826; Landegren, et al., (1988) *Science* 241:1077; Van Brunt, (1990) *Biotechnology* 8:291; Wu and Wallace, (1989) *Gene* 4:560; Barringer, et al., (1990) *Gene* 89:117 and Sooknanan and Malek, (1995) *Biotechnology* 13:563. Additional methods, useful for cloning nucleic acids in the context of the invention, include Wallace, et al., U.S. Pat. No. 5,426,039. Improved methods of amplifying large nucleic acids by PCR are summarized in Cheng, et al., (1994) *Nature* 369:684 and the references therein.

Certain polynucleotides of the invention can be synthesized utilizing various solid-phase strategies involving mononucleotide- and/or trinucleotide-based phosphoramidite coupling chemistry. For example, nucleic acid sequences can be synthesized by the sequential addition of activated monomers and/or trimers to an elongating polynucleotide chain. See, e.g., Caruthers, et al., (1992) *Meth Enzymol* 211:3. In lieu of synthesizing the desired sequences, essentially any nucleic acid can be custom ordered from any of a variety of commercial sources, such as The Midland Certified Reagent Company (mcrc@oligos.com) (Midland, Tex.), The Great American Gene Company (available on the World Wide Web at genco.com) (Ramona, Calif.), ExpressGen, Inc. (available on the World Wide Web at expressgen.com) (Chicago Ill.), Operon Technologies, Inc. (available on the World Wide Web at operon.com) (Alameda Calif.), and many others.

Although the present invention has been described in some detail by way of illustration and example for purposes of clarity of understanding, it will be obvious that certain changes and modifications may be practiced within the scope of the appended claims.

TABLE 1

Sequences in Sequence Listing

| SEQ ID NO | PP/NT | DESCRIPTION |
| --- | --- | --- |
| 1 | nucleotide | ZM-ETO1-1 cfp3n.pk009.o19.f.FIS |
| 2 | polypeptide | ZM-ETO1-1 cfp3n.pk009.o19.f.FIS |
| 3 | nucleotide | ZM-ETO1-2 cfp6n.pk073.o21.FIS |
| 4 | polypeptide | ZM-ETO1-2cfp6n.pk073.o21.FIS |
| 5 | nucleotide | ZM-ETO1-3 cta1.pk0036.f.FIS |
| 6 | polypeptide | ZM-ETO1-3 cta1.pk0036.f + cfp1n.pk047.e9a.FIS |
| 7 | nucleotide | ZM-ETO1-4 cfp7n.pk074.p17.FIS |
| 8 | polypeptide | ZM-ETO1-4 cfp7n.pk074.p17.FIS |
| 9 | nucleotide | GM-ETO1-1 PSO415110 genomic |
| 10 | polypeptide | GM-ETO1-1 PSO415110 |
| 11 | polypeptide | N-Terminal Domain of ETO1 (Consensus) |
| 12 | polypeptide | C-Terminal Domain of ETO1 (Consensus) |
| 13 | nucleotide | ASal-A20 oligonucleotide |

EXAMPLES

Example 1

Construction of cDNA Libraries

Total RNA Isolation

Total RNA for SEQ ID NO: 1, 3, 5 and 7 was obtained from maize genotype Hill (Armstrong and Phillips, (1988) *Crop Sci.* 28:363-369) and from night harvested leaf tissue at the V8-V10 stage of maize genotype B75. Total RNA for SEQ ID NO: 9 was obtained from soybean. The total RNA was isolated from the maize and soybean tissues with TRIzol Reagent (Life Technology Inc. Gaithersburg, Md.) using a modification of the guanidine isothiocyanate/acid-phenol procedure described by Chomczynski and Sacchi (Chomczynski and Sacchi, (1987) Anal. Biochem. 162:156). In brief, plant tissue samples were pulverized in liquid nitrogen before the addition of the TRIzol Reagent and then were further homogenized with a mortar and pestle. Addition of chloroform followed by centrifugation was conducted for separation of an aqueous phase and an organic phase. The total RNA was recovered by precipitation with isopropyl alcohol from the aqueous phase.

Poly (A)+RNA Isolation

The selection of poly (A)+RNA from total RNA was performed using PolyATact system (Promega Corporation, Madison, Wis.). In brief, biotinylated oligo(dT) primers were used to hybridize to the 3' poly (A) tails on mRNA. The hybrids were captured using streptavidin coupled to paramagnetic particles and a magnetic separation stand. The mRNA was washed at high stringency conditions and eluted by RNase-free deionized water. cDNA Library Construction cDNA synthesis was performed and unidirectional cDNA libraries were constructed using the SuperScript Plasmid System (Life Technology Inc. Gaithersburg, Md.). The first strand of cDNA was synthesized by priming an oligo(dT) primer containing a Not I site.

The reaction was catalyzed by SuperScript Reverse Transcriptase II at 45° C. The second strand of cDNA was labeled with alpha-32P-dCTP and a portion of the reaction was analyzed by agarose gel electrophoresis to determine cDNA sizes. cDNA molecules smaller than 500 base pairs and unligated adapters were removed by Sephacryl-5400 chromatography. The selected cDNA molecules were ligated into pSPORTI vector in between of Not I and Sal I sites.

TABLE 2 cDNAs, Corresponding Sequence Identifiers, and Source

| | | |
|---|---|---|
| cfp3n.pk009.o19.f | SEQ ID 1 & 2 | Maize Ear, pooled V10-V14-v16-VT, Full-length enriched normalized |
| cfp6n.pk073.o21.f | SEQ ID 3 & 4 | Maize Leaf and Seed pooled, Full-length enriched normalized |
| cfp6n.pk003.j6 | SEQ ID 5 & 6 | Maize Leaf and Seed pooled, Full-length enriched normalized |
| cfp7n.pk074.p17 | SEQ ID 7 & 8 | Maize Root, Pooled stages, Full-length enriched, normalized |
| sfl1.pk0066.b1 | SEQ ID 9 & 10 | Soybean (*Glycine max* L.) immature flower |

Based on the sequence comparison of the soybean and maize sequences two domains that are highly conserved across all of the sequences were identified: one N-terminal and one C-terminal.

N-TERMINAL DOMAIN
(SEQ ID NO: 11)
F-X8-C-X-R-X3-A-X-L-S-X-P-X4-L-X-G-X-F-X-E-X17-M-

X6-S-X16-L-X2-A-X2-F-C-C-X2-L-K-X2-C-X3-L-X8-A-X8-

E-X5-L-X3-CLQ

C-TERMINAL DOMAIN
(SEQ ID NO: 12)
W-S-X-V-D-D-X2-S-L-X-V-X3-M-L-X8-L-X-F-R-Q-S-L-L-

L-L-R-L-N-C-X3-A-M-R-X-L-X2-A-X8-E-R-L-V-Y-E-G-W-

X-L-Y-D-X-G-X3-E-X-L-X-K-A-X3-I-X3-R-S-F-E-A-X-F-

L-X-A-Y-X-L-X5-D-X6-V-X3-L-X2-A-X2-C-X2-D-X-L-R-K-

G-Q-A-X-N-N-X-G-X2-Y-X5-L-D-X-A-X3-Y-X2-A-X4-H-X-

R-A-X-Q-G-L-A-R-V-X2-L-X-N-X4-A-X2-E-M-T-X-L-X-E-

X5-A-X-A-Y-E-K-R-S-E-Y-X2-R-X5-D-L-X5-L-D-P-X-R-X-

Y-P-Y-R-Y-R-A-A-V-L-M-D

Example 2 cDNA Sequencing and Library Subtraction

Sequencing Template Preparation

Individual colonies were picked and DNA was prepared either by PCR with M13 forward primers and M13 reverse primers, or by plasmid isolation. All the cDNA clones were sequenced using M13 reverse primers.

Q-bot Subtraction Procedure cDNA libraries subjected to the subtraction procedure were plated out on 22×22 cm² agar plate at density of about 3,000 colonies per plate. The plates were incubated in a 37° C. incubator for 12-24 hours. Colonies were picked into 384-well plates by a robot colony picker, Q-bot (GENETIX Limited). These plates were incubated overnight at 37° C.

Once sufficient colonies were picked, they were pinned onto 22×22 cm² nylon membranes using Q-bot. Each membrane contained 9,216 colonies or 36,864 colonies. These membranes were placed onto agar plate with appropriate antibiotic. The plates were incubated at 37° C. for overnight.

After colonies were recovered on the second day, these filters were placed on filter paper pre-wetted with denaturing solution for four minutes, then were incubated on top of a boiling water bath for additional four minutes. The filters were then placed on filter paper pre-wetted with neutralizing solution for four minutes. After excess solution was removed by placing the filters on dry filter papers for one minute, the colony side of the filters were place into Proteinase K solution, incubated at 37° C. for 40-50 minutes. The filters were placed on dry filter papers to dry overnight. DNA was then cross-linked to nylon membrane by UV light treatment.

Colony hybridization was conducted as described by Sambrook, et al., (in Molecular Cloning: A laboratory Manual, 2nd Edition). The following probes were used in colony hybridization:

1. First strand cDNA from the same tissue as the library was made from to remove the most redundant clones.
2. 48-192 most redundant cDNA clones from the same library based on previous sequencing data.
3. 192 most redundant cDNA clones in the entire maize sequence database.
4. ASal-A20 oligonucleotide: TCG ACC CAC GCG TCC GAA AAA AAA AAA AAA AAA AAA (SEQ ID NO: 13), removes clones containing a poly A tail but no cDNA.
5. cDNA clones derived from rRNA.

The image of the autoradiography was scanned into computer and the signal intensity and cold colony addresses of each colony was analyzed. Re-arraying of cold colonies from 384 well plates to 96 well plates was conducted using Q-bot.

Example 3

Homology Search

This example describes identification of the gene from a computer homology search. Gene identities were determined by conducting BLAST (Basic Local Alignment Search Tool; Altschul, et al., (1993) *J. Mol. Biol.* 215:403-410) searches under default parameters for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL and DDBJ databases). The cDNA sequences were analyzed for similarity to all publicly available DNA sequences contained in the "nr" database using the BLASTN algorithm.

The DNA sequences were translated in all reading frames and compared for similarity to all publicly available protein sequences contained in the "nr" database using the BLASTX algorithm (Gish and States, (1993) *Nature Genetics* 3:266-272) provided by the NCBI. In some cases, the sequencing data from two or more clones containing overlapping segments of DNA were used to construct contiguous DNA sequences.

Example 4

Transformation and Regeneration of Transgenic Plants

Immature maize embryos from greenhouse donor plants are bombarded with a plasmid containing the ETO1 sequence operably linked to the a promoter such as a drought-inducible promoter RAB17 promoter (Vilardell, et al., (1990) *Plant Mol Biol* 14:423-432), a constitutive promoter, a female preferred promoter, such as ZM-ADF4 (US Patent Application Publication Number 2009/0094713) or EEP1 (US Patent Application Publication Number 2004/0237147) or a root specific promoter and the selectable marker gene MO-PAT, which confers resistance to the herbicide Bialaphos or the BAR selectable marker. Alternatively, the selectable marker gene is provided on a separate plasmid. Transformation is performed as follows. Media recipes follow below.

Preparation of Target Tissue

The ears are husked and surface sterilized in 30% Clorox® bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the ETO1 sequence operably linked to an ubiquitin promoter is made. This plasmid DNA plus plasmid DNA containing a PAT selectable marker is precipitated onto 1.1 µm (average diameter) tungsten pellets using a $CaCl_2$ precipitation procedure as follows:

100 µl prepared tungsten particles in water
10 µl (1 µg) DNA in Tris EDTA buffer (1 µg total DNA)
100 µl 2.5 M $CaCl_2$
10 µl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol and centrifuged for 30 seconds. Again the liquid is removed and 105 µl 100% ethanol is added to the final tungsten particle pellet. For particle gun bombardment, the tungsten/DNA particles are briefly sonicated and 10 µl spotted onto the center of each macrocarrier and allowed to dry about 2 minutes before bombardment.

Particle Gun Treatment

The sample plates are bombarded at level #4 in a particle gun. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for increased drought tolerance. Assays to measure improved drought tolerance are routine in the art and include, for example, increased kernel set under drought conditions when compared to control maize plants under identical environmental conditions. Alternatively, the transformed plants can be monitored for a modulation in meristem development (e.g., a decrease in spikelet formation on the ear). See, for example, Bruce, et al., (2002) *Journal of Experimental Botany* 53:13-25.

Bombardment and Culture Media

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D and 2.88 g/l L-proline (brought to volume with D-I $H_2O$ following adjustment to pH 5.8 with KOH); 2.0 g/l Gelrite (added after bringing to volume with D-I $H_2O$) and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose and 2.0 mg/l 2,4-D (brought to volume with D-I $H_2O$ following adjustment to pH 5.8 with KOH); 3.0 g/l Gelrite (added after bringing to volume with D-I $H_2O$) and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL and 0.40 g/l glycine brought to volume with polished D-I $H_2O$) (Murashige and Skoog, (1962) *Physiol. Plant.* 15:473), 100 mg/l myo-inositol, 0.5 mg/l zeatin, 60 g/l sucrose and 1.0 ml/l of 0.1 mM abscisic acid (brought to volume with polished D-I $H_2O$ after adjusting to pH 5.6); 3.0 g/l Gelrite (added after bringing to volume with D-I $H_2O$) and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL and 0.40 g/l glycine brought to volume with polished D-I $H_2O$), 0.1 g/l myo-inositol and 40.0 g/l sucrose (brought to volume with polished D-I $H_2O$ after adjusting pH to 5.6) and 6 g/l bacto-agar (added after bringing to volume with polished D-I $H_2O$), sterilized and cooled to 60° C.

Example 5

*Agrobacterium*-Mediated Transformation

For *Agrobacterium*-mediated transformation of maize with an expression construct with the ETO1 sequence of the present invention, preferably the method of Zhao is employed (U.S. Pat. No. 5,981,840 and PCT Patent Application Publication WO 1998/32326; the contents of which are hereby incorporated by reference). Briefly, immature embryos are isolated from maize and the embryos contacted with a suspension of *Agrobacterium*, where the bacteria are capable of transferring the ETO1 sequences to at least one cell of at least one of the immature embryos (step 1: the infection step). In this step the immature embryos are preferably immersed in an

*Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step) and preferably calli grown on selective medium are cultured on solid medium to regenerate the plants. Plants are monitored and scored for a modulation in meristem development: for instance, alterations of size and appearance of the shoot and floral meristems and/or increased yields of leaves, flowers and/or fruits.

Example 6

Soybean Embryo Transformation

Soybean embryos are bombarded with a plasmid containing an ETO1 sequence operably linked to an ubiquitin or other constitutive promoter as follows. To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein, et al., (1987) *Nature* (*London*) 327:70-73, U.S. Pat. No. 4,945,050). A DuPont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell, et al., (1985) *Nature* 313:810-812), the hygromycin phosphotransferase gene from plasmid pJR225 (from *E. coli*; Gritz, et al., (1983) *Gene* 25:179-188) and the 3' region of the nopaline synthase gene from the T-DNA of the Ti plasmid of *Agrobacterium tumefaciens*. The expression cassette comprising an ETO1 encoding sequence operably linked to the ubiquitin promoter can be isolated as a restriction fragment. This fragment can then be inserted into a unique restriction site of the vector carrying the marker gene.

To 50 μl of a 60 mg/ml 1 μm gold particle suspension is added (in order): 5 μl DNA (1 μg/μl), 20 μl spermidine (0.1 M), and 50 μl CaCl$_2$ (2.5 M). The particle preparation is then agitated for three minutes, spun in a microfuge for 10 seconds and the supernatant removed. The DNA-coated particles are then washed once in 400 μl 70% ethanol and resuspended in 40 μl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Sunflower Meristem Tissue Transformation

Sunflower meristem tissues are transformed with an expression cassette containing an ETO1 sequence operably linked to a ubiquitin promoter as follows (see also, European Patent Number EP 0 486233, herein incorporated by reference and Malone-Schoneberg, et al., (1994) *Plant Science* 103:199-207). Mature sunflower seed (*Helianthus annuus* L.) are dehulled using a single wheat-head thresher. Seeds are surface sterilized for 30 minutes in a 20% Clorox® bleach solution with the addition of two drops of Tween® 20 per 50 ml of solution. The seeds are rinsed twice with sterile distilled water.

Split embryonic axis explants are prepared by a modification of procedures described by Schrammeijer, et al. (Schrammeijer, et al., (1990) *Plant Cell Rep.* 9:55-60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige, et al., (1962) *Physiol. Plant.*, 15:473-497), Shepard's vitamin additions (Shepard, (1980) in *Emergent Techniques for the Genetic Improvement of Crops* (University of Minnesota Press, St. Paul, Minn.) 0, 40 mg/l adenine sulfate, 30 WI sucrose, 0.5 mg/l 6-benzyl-aminopurine (BAP), 0.25 mg/l indole-3-acetic acid (IAA), 0.1 mg/l gibberellic acid (GA3), pH 5.6 and 8 WI Phytagar.

The explants are subjected to microprojectile bombardment prior to *Agrobacterium* treatment (Bidney, et al., (1992) *Plant Mol. Biol.* 18:301-313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the ETO1 gene operably linked to the ubiquitin promoter is introduced into *Agrobacterium* strain EHA105 via freeze-thawing as described by Holsters, et al., (1978) *Mol. Gen. Genet.* 163:181-187. This plasmid further comprises a kanamycin selectable marker gene (i.e., nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The *Agrobacterium* cells are pelleted and resuspended at a final $OD_{600}$ of 0.5 in an inoculation medium comprised of 12.5 mM MES pH 5.7, 1 gm/l $NH_4Cl$, and 0.3 gm/l $MgSO_4$.

Freshly bombarded explants are placed in an *Agrobacterium* suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for a modulation in meristem development (i.e., an alteration of size and appearance of shoot and floral meristems).

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by ETO1 activity analysis of leaf extracts while transgenic seeds harvested from NPTII-positive $T_0$ plants are identified by ETO1 analysis of small portions of dry seed cotyledon.

An alternative sunflower transformation protocol allows the recovery of transgenic progeny without the use of chemical selection pressure. Seeds are dehulled and surface-sterilized for 20 minutes in a 20% Clorox bleach solution with the addition of two to three drops of Tween 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA and 0.8% Phytagar at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar) and then cultured on the medium for 24 hours in the dark.

Approximately 18.8 mg of 1.8 μm tungsten particles are resuspended in 150 μl absolute ethanol. After sonication, 8 μl of it is dropped on the center of the surface of macrocarrier. Each plate is bombarded twice with 650 psi rupture discs in the first shelf at 26 mm of Hg helium gun vacuum.

The plasmid of interest is introduced into *Agrobacterium tumefaciens* strain EHA105 via freeze thawing as described previously. The pellet of overnight-grown bacteria at 28° C. in a liquid YEP medium (10 g/l yeast extract, 10 g/l Bactopeptone, and 5 g/l NaCl, pH 7.0) in the presence of 50 μg/l kanamycin is resuspended in an inoculation medium (12.5 mM 2-mM 2-(N-morpholino) ethanesulfonic acid, MES, 1 g/l $NH_4Cl$ and 0.3 g/l $MgSO_4$ at pH 5.7) to reach a final concentration of 4.0 at $OD_{600}$. Particle-bombarded explants are transferred to GBA medium (374E), and a droplet of bacteria suspension is placed directly onto the top of the meristem. The explants are co-cultivated on the medium for 4 days, after which the explants are transferred to 374C medium (GBA with 1% sucrose and no BAP, IAA, GA3 and supplemented with 250 μg/ml cefotaxime). The plantlets are cultured on the medium for about two weeks under 16-hour day and 26° C. incubation conditions.

Explants (around 2 cm long) from two weeks of culture in 374C medium are screened for a modulation in meristem development (i.e., an alteration of size and appearance of shoot and floral meristems). After positive explants are identified, those shoots that fail to exhibit modified ETO1 activity are discarded, and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for modified ETO1 expression are grafted to Pioneer hybrid 6440 in vitro-grown sunflower seedling rootstock. The rootstocks are prepared in the following manner. Seeds are dehulled and surface-sterilized for 20 minutes in a 20% Clorox® bleach solution with the addition of two to three drops of Tween 20 per 100 ml of solution, and are rinsed three times with distilled water. The sterilized seeds are germinated on the filter moistened with water for three days, then they are transferred into 48 medium (half-strength MS salt, 0.5% sucrose, 0.3% gelrite pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with parafilm. After one week of culture on the medium, grafted plants are transferred to soil. In the first two weeks, they are maintained under high humidity conditions to acclimatize to a greenhouse environment.

Example 8

Rice Tissue Transformation

One method for transforming DNA into cells of higher plants that is available to those skilled in the art is high-velocity ballistic bombardment using metal particles coated with the nucleic acid constructs of interest (see, Klein, et al., (1987) *Nature (London)* 327:70-73 and see, U.S. Pat. No. 4,945,050). A Biolistic PDS-1000/He (BioRAD Laboratories, Hercules, Calif.) is used for these complementation experiments. The particle bombardment technique is used to transform the ETO1 mutants and wild type rice with DNA fragments The bacterial hygromycin B phosphotransferase (Hpt II) gene from *Streptomyces hygroscopicus* that confers resistance to the antibiotic is used as the selectable marker for rice transformation. In the vector, pML18, the Hpt II gene was engineered with the 35S promoter from Cauliflower Mosaic Virus and the termination and polyadenylation signals from the octopine synthase gene of *Agrobacterium tumefaciens*. pML18 was described in WO 1997/47731, which was published on Dec. 18, 1997, the disclosure of which is hereby incorporated by reference.

Embryogenic callus cultures derived from the scutellum of germinating rice seeds serve as source material for transformation experiments. This material is generated by germinating sterile rice seeds on a callus initiation media (MS salts, Nitsch and Nitsch vitamins, 1.0 mg/l 2,4-D and 10 µM AgNO$_3$) in the dark at 27-28° C. Embryogenic callus proliferating from the scutellum of the embryos is the transferred to CM media (N6 salts, Nitsch and Nitsch vitamins, 1 mg/l 2,4-D, Chu, et al., (1985) *Sci. Sinica* 18:659-668). Callus cultures are maintained on CM by routine sub-culture at two week intervals and used for transformation within 10 weeks of initiation.

Callus is prepared for transformation by subculturing 0.5-1.0 mm pieces approximately 1 mm apart, arranged in a circular area of about 4 cm in diameter, in the center of a circle of Whatman #541 paper placed on CM media. The plates with callus are incubated in the dark at 27-28° C. for 3-5 days. Prior to bombardment, the filters with callus are transferred to CM supplemented with 0.25 M mannitol and 0.25 M sorbitol for 3 hr in the dark. The petri dish lids are then left ajar for 20-45 minutes in a sterile hood to allow moisture on tissue to dissipate.

Each genomic DNA fragment is co-precipitated with pML18 containing the selectable marker for rice transformation onto the surface of gold particles. To accomplish this, a total of 10 µg of DNA at a 2:1 ratio of trait:selectable marker DNAs are added to 50 µl aliquot of gold particles that have been resuspended at a concentration of 60 mg ml$^{-1}$. Calcium chloride (50 µl of a 2.5 M solution) and spermidine (20 µl of a 0.1 M solution) are then added to the gold-DNA suspension as the tube is vortexing for 3 min. The gold particles are centrifuged in a microfuge for 1 sec and the supernatant removed. The gold particles are then washed twice with 1 ml of absolute ethanol and then resuspended in 50 µl of absolute ethanol and sonicated (bath sonicator) for one second to disperse the gold particles. The gold suspension is incubated at −70° C. for five minutes and sonicated (bath sonicator) if needed to disperse the particles. Six µl of the DNA-coated gold particles are then loaded onto mylar macrocarrier disks and the ethanol is allowed to evaporate.

At the end of the drying period, a petri dish containing the tissue is placed in the chamber of the PDS-1000/He. The air in the chamber is then evacuated to a vacuum of 28-29 inches Hg. The macrocarrier is accelerated with a helium shock wave using a rupture membrane that bursts when the He pressure in the shock tube reaches 1080-1100 psi. The tissue is placed approximately 8 cm from the stopping screen and the callus is bombarded two times. Two to four plates of tissue are bombarded in this way with the DNA-coated gold particles. Following bombardment, the callus tissue is transferred to CM media without supplemental sorbitol or mannitol.

Within 3-5 days after bombardment the callus tissue is transferred to SM media (CM medium containing 50 mg/l hygromycin). To accomplish this, callus tissue is transferred from plates to sterile 50 ml conical tubes and weighed. Molten top-agar at 40° C. is added using 2.5 ml of top agar/100 mg of callus. Callus clumps are broken into fragments of less than 2 mm diameter by repeated dispensing through a 10 ml pipet. Three ml aliquots of the callus suspension are plated onto fresh SM media and the plates are incubated in the dark for 4 weeks at 27-28° C. After 4 weeks, transgenic callus events are identified, transferred to fresh SM plates and grown for an additional 2 weeks in the dark at 27-28° C.

Growing callus is transferred to RM1 media (MS salts, Nitsch and Nitsch vitamins, 2% sucrose, 3% sorbitol, 0.4% gelrite+50 ppm hyg B) for 2 weeks in the dark at 25° C. After 2 weeks the callus is transferred to RM2 media (MS salts, Nitsch and Nitsch vitamins, 3% sucrose, 0.4% gelrite+50 ppm hyg B) and placed under cool white light (~40 µEm$^{-2}$s$^{-1}$) with a 12 hr photo period at 25° C. and 30-40% humidity. After 2-4 weeks in the light, callus begin to organize, and form shoots. Shoots are removed from surrounding callus/media and gently transferred to RM3 media (½×MS salts, Nitsch and Nitsch vitamins, 1% sucrose+50 ppm hygromycin B) in phytatrays (Sigma Chemical Co., St. Louis, Mo.) and incubation is continued using the same conditions as described in the previous step.

Plants are transferred from RM3 to 4" pots containing Metro mix 350 after 2-3 weeks, when sufficient root and shoot growth have occurred. The seed obtained from the transgenic plants is examined for genetic complementation of the ETO1 mutation with the wild-type genomic DNA containing the ETO1 gene.

Example 9

Variants of ETO1 Sequences

A. Variant Nucleotide Sequences of ETO1 Proteins that do not Alter the Encoded Amino Acid Sequence The ETO1 sequences having the nucleotide sequence of the open reading frame with about 70%, 75%, 80%, 85%, 90% and 95% nucleotide sequence identity when compared to the starting unaltered ORF nucleotide sequence of the corresponding SEQ ID NO: 1, 3, 5, 7 or 9. These functional variants are generated using a standard codon table. While the nucleotide sequence of the variants are altered, the amino acid sequence encoded by the open reading frames do not change.

B. Variant Amino Acid Sequences of ETO 1 Polypeptides

Variant amino acid sequences of the ETO1 polypeptides are generated. In this example, one amino acid is altered. Specifically, the open reading frames are reviewed to determine the appropriate amino acid alteration. The selection of the amino acid to change is made by consulting the protein alignment (with the other orthologs and other gene family members from various species). An amino acid is selected that is deemed not to be under high selection pressure (not highly conserved) and which is rather easily substituted by an amino acid with similar chemical characteristics (i.e., similar functional side-chain). Using the protein alignment, an appropriate amino acid can be changed. Once the targeted amino acid is identified, the procedure outlined in the following section C is followed. Variants having about 70%, 75%, 80%, 85%, 90% and 95% nucleic acid sequence identity are generated using this method.

C. Additional Variant Amino Acid Sequences of ETO1 Polypeptides

In this example, artificial protein sequences are created having 80%, 85%, 90% and 95% identity relative to the reference protein sequence. This latter effort requires identifying conserved and variable regions from the alignment and then the judicious application of an amino acid substitutions table. These parts will be discussed in more detail below.

Largely, the determination of which amino acid sequences are altered is made based on the conserved regions among ETO1 protein or among the other ETO1 polypeptides. Based on the sequence alignment, the various regions of the ETO1 polypeptide that can likely be altered are represented in lower case letters, while the conserved regions are represented by capital letters. It is recognized that conservative substitutions can be made in the conserved regions below without altering function. In addition, one of skill will understand that functional variants of the ETO1 sequence of the invention can have minor non-conserved amino acid alterations in the conserved domain.

Artificial protein sequences are then created that are different from the original in the intervals of 80-85%, 85-90%, 90-95% and 95-100% identity. Midpoints of these intervals are targeted, with liberal latitude of plus or minus 1%, for example. The amino acids substitutions will be effected by a custom Perl script. The substitution table is provided below in Table 3.

TABLE 3

Substitution Table

| Amino Acid | Strongly Similar and Optimal Substitution | Rank of Order to Change | Comment |
|---|---|---|---|
| I | L, V | 1 | 50:50 substitution |
| L | I, V | 2 | 50:50 substitution |
| V | I, L | 3 | 50:50 substitution |
| A | G | 4 | |
| G | A | 5 | |
| D | E | 6 | |
| E | D | 7 | |
| W | Y | 8 | |
| Y | W | 9 | |
| S | T | 10 | |
| T | S | 11 | |
| K | R | 12 | |
| R | K | 13 | |
| N | Q | 14 | |
| Q | N | 15 | |
| F | Y | 16 | |
| M | L | 17 | First methionine cannot change |
| H | | Na | No good substitutes |
| C | | Na | No good substitutes |
| P | | Na | No good substitutes |

First, any conserved amino acids in the protein that should not be changed is identified and "marked off" for insulation from the substitution. The start methionine will of course be added to this list automatically. Next, the changes are made.

H, C and P are not changed in any circumstance. The changes will occur with isoleucine first, sweeping N-terminal to C-terminal. Then leucine, and so on down the list until the desired target it reached. Interim number substitutions can be made so as not to cause reversal of changes. The list is ordered 1-17, so start with as many isoleucine changes as needed before leucine, and so on down to methionine. Clearly many amino acids will in this manner not need to be changed. L, I and V will involve a 50:50 substitution of the two alternate optimal substitutions.

The variant amino acid sequences are written as output. Perl script is used to calculate the percent identities. Using this procedure, variants of the ETO1 polypeptides are generating having about 80%, 85%, 90% and 95% amino acid identity to the starting unaltered ORF nucleotide sequence of SEQ ID NO: 1, 3, 5, 7 or 9.

Example 10

Transgenic Maize Plants $T_0$ transgenic maize plants containing the ETO1 construct under the control of a promoter are generated. These plants are grown in greenhouse conditions, under the FASTCORN system, as detailed in US Patent Application Publication Number 2003/0221212, U.S. patent application Ser. No. 10/367,417.

Each of the plants is then analyzed for measurable alteration in one or more of the following characteristics in the following manner:

$T_1$ progeny derived from self fertilization of each $T_0$ plant containing a single copy of each construct that were found to segregate 1:1 for the transgenic event were analyzed for improved growth rate in low $KNO_3$. Growth is monitored up to anthesis when cumulative plant growth, growth rate and ear weight were determined for transgene positive, transgene null, and non-transformed controls events. The distribution of the phenotype of individual plants was compared to the distribution of a control set and to the distribution of all the remaining treatments. Variances for each set were calculated and compared using an F test, comparing the event variance to a non-transgenic control set variance and to the pooled variance of the remaining events in the experiment. The greater the response to $KNO_3$, the greater the variance within an event set and the greater the F value. Positive results will be compared to the distribution of the transgene within the event to make sure the response segregates with the transgene.

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for reducing ethylene biosynthesis in a plant, comprising:
   (a) introducing into a plant cell a recombinant expression cassette comprising a first polynucleotide operably linked to a heterologous promoter, wherein said expression cassette directs expression of said first polynucleotide, wherein the first polynucleotide is selected from the group consisting of:
      i. a polynucleotide comprising the full length nucleotide sequence of SEQ ID NO: 9;
      ii. a polynucleotide having at least 95% sequence identity to the full length of the sequence set forth in SEQ ID NO: 9, wherein the polynucleotide encodes a polypeptide having ethylene over-producer 1 (ETO1) activity and wherein the polypeptide comprises the N-terminal domain provided as SEQ ID NO: 11 and the C-terminal domain provided as SEQ ID NO: 12; and
      iii. a polynucleotide encoding a polypeptide comprising the full length amino acid sequence set forth in SEQ ID NO: 10;
   (b) culturing the plant cell under plant cell growing conditions and regenerating a plant therefrom;
   wherein the level of ethylene biosynthesis in said plant is reduced, relative to a control.

2. The method of claim 1, wherein the heterologous promoter is a tissue-preferred promoter.

3. The method of claim 1, wherein the plant cell is from a plant selected from the group consisting of maize, soybean, sunflower, sorghum, canola, wheat, alfalfa, cotton, rice, barley and millet.

4. The method of claim 3, wherein the plant is maize.

5. The method of claim 1, wherein the heterologous promoter is a stress-inducible promoter.

6. A transgenic plant produced by the method of claim 1.

7. The transgenic plant of claim 6, wherein the plant has decreased ethylene production when compared to a control plant.

* * * * *

SEQUENCE LISTING

<160> NUMBER OF SEQ ID NOS: 13

<210> SEQ ID NO 1
<211> LENGTH: 3395
<212> TYPE: DNA
<213> ORGANISM: Zea mays

<400> SEQUENCE: 1

| | | | | | | |
|---|---|---|---|---|---|---|
| cggctctctc | tctagctgca | gattggtgcc | tcaccctag | cggtcggtgg | ttggggccgg | 60 |
| gttccgacgg | ctgctcggga | gctcgactgg | ggcttggaag | tccaaagccg | ccgcctcctc | 120 |
| gtggcgcgcc | gctccggaat | tcttgccttc | ttgggctccg | aatctcgccg | cccggtgttt | 180 |
| gatttgcggc | gttcctagcg | aattcggggc | tgatttgccc | ccctatggcg | aggatttgag | 240 |
| tggactcgag | aggaacaagt | agaggggagt | cctgatttgg | gcccctgccg | tggtatgtgc | 300 |
| catgaggaag | ctcttcttct | ccgagtcggc | ctgcaaggag | accaagctcc | actgcgcgcc | 360 |
| ccactcatgg | ctgcccctcg | agaggggaa | gctctccaag | ttctccggcc | atgccgccgc | 420 |
| cggctcctcc | atagaggcat | tgatgaagat | gccggagccg | gcagtgcttc | cgtacttcaa | 480 |
| gcccgcgaac | tatgtcgaca | tactggctca | gatacacgag | gagctggagt | cctgccctcc | 540 |
| tgacgagaag | tcctgcctgt | acctgctcca | gttccaggtc | ttccgcggcc | ttggggaggc | 600 |
| caagctgtca | cggaggagcc | tccagtctgc | gtggagaag | gcgagcacca | tacacgagaa | 660 |
| gctcatcttt | ggggcgtggc | tcaagtacga | aagaaaggg | gaggaggcaa | tctccgacct | 720 |
| gctcagctcg | tgctgcaagt | gctcacagga | gttcaggctg | ctggattttg | tgtcgcaagt | 780 |
| ctccactggg | tcacacatga | tgaactatga | tgatgatgat | gatgagtctg | atgagtttcg | 840 |
| gggttctgcg | gtggttcatt | tccggataag | agatgatatg | attgcatgcg | atcgacggaa | 900 |
| acttgcagct | ctgtcaactc | cactgtatgc | aatgcttaac | ggtggattta | gggaatccta | 960 |
| tctggaggtc | attgacatgt | ctagaaatgg | tatctcccct | attggcatga | gggcaatcag | 1020 |
| taaattcagc | ctatcaggaa | gactaccttta | tttgtcagca | gatgctatct | ggagatgct | 1080 |
| tgattttgcc | aataagtttt | gctgcaaggg | cctcaaggat | gcctgtgagc | gaaagcttgc | 1140 |
| ttcttttcatc | tcttcaaggc | aagatgctat | agatttcatg | gagtgtgctc | ttgagctggg | 1200 |
| ctgttccatt | cttgctgctt | catgcttaca | agtgctcttg | aatgagcttc | cagagtgctt | 1260 |
| gaatgatgaa | caagtggtta | ggatattctc | ctctgcaaat | aaggcacaga | gattgacaat | 1320 |
| ggttggcaat | gcatctttct | ccctatattg | ccttctcagt | gaagtctccg | tgagtaccaa | 1380 |
| cccaacatcg | gatgtcactg | tgagtttctt | ggaaaaactg | gtagagtcgg | catcagattc | 1440 |
| taggcagaag | cagctggcct | tacatcagct | ggcatgcacc | agatttttaa | ggaaagatta | 1500 |
| ccctgaatct | gagtgcttgt | tcaatgctgc | cttttctgct | ggccatcttt | attcgttagt | 1560 |
| gggtttggct | agattggcct | ctctgagggg | taataagcat | tttgctctca | agttgctaga | 1620 |
| ctctgtgatg | tcatctcggt | ggcctcttgg | atggatgtat | caagagagag | cactctattt | 1680 |
| ggatggtgat | aacaagttag | aaaatcttaa | caaggctact | gagttggacc | ctacccttac | 1740 |
| atatccctat | atgtttcgag | ctgcatcttt | gatgaaaagg | caaagtgttg | aagctgcatt | 1800 |
| gatggagata | aaccggatcc | ttggatttaa | actggtgctg | gagtgcttag | aactaaggtt | 1860 |
| ctgttgctac | cttgcccttg | aggattatag | ggctgcctta | tgtgacgtgc | aggcaatcct | 1920 |
| cactcttgcc | ccagattatc | gtatgattgg | tggccgggtt | gctgccaagc | agctgcgaat | 1980 |
| gctagtgcta | gagaatgtag | agcagtggac | acctgctgac | tgttggatgc | aactttatga | 2040 |
| tcgctggtcg | tctgtggatg | atataggggtc | cctctctgtt | atatatcaaa | tgctggagtc | 2100 |

```
agagactgcc aaaggagttt tgtactttag acaatctttg cttcttctca gattaaactg    2160
tcctgaggcg gcaatgagga gtttgcagct tgctcgtgag catgctgcaa gtgatcatga    2220
aaggcttgtc tatgaaggat ggatattgta tgatactggc cactgcgagg aaggactgca    2280
gaaagcggaa gcatcaattg caatacaacg gtcatttgag cattttttc tgaaagctta     2340 tgctttggct gattcgagtc ttgatccttc gaccacagca acagttgtat cacttctaga    2400
agatgcattg cggtgtccct cagatagact tcggaagggt caagctctaa acaaccttgg    2460
aagtgtttat gtggattgtg ggaagcttga cctggcagct gaatgctaca ttaacgccct    2520
aaagatcggc cacaccagag cgcaccaagg ccttgcgagg gttcatttcc ttcggaacaa    2580
cagagtcggt gcgtatgatg aaatgaccaa gctgatagag aaggccagga caacgcgtc    2640 ggcatacgag aagagatctg agtactgcga gcgggagctg acgaaaacgg acttgcagat    2700
ggtcaccaaa ctcgaccctc tgcgagtcta cccctacaga taccgtgctg ctgtgctgat    2760
ggacaaccac aaggagaaag aggccgtcgc ggagctgacc agggcgatcg ccttcaaggc    2820
ggacctgaac ctgctccacc tgcgcgcggc cttccacgag cacatcggcg acatctcgag    2880
cgccctccgg gactgccgcg cggccctcct ggtggacccc aaccaccagg agatgctgga    2940
gctgcaccac cgggtgaaca gccaggaacc atgagcggag cgccgccatg gtgtacatac    3000
aggacgtgat aggaagcccc tcatagccaa ccccccgcca taccagtgta tgttttgtac    3060
catacacagc atgtcaatgt aaggatagta gaaaagccac tttaggtccc tccctggctc    3120 cctcccttg caaaccaaac acctacattc cttgtgtgcc tagttagata tgttgtttgc     3180
catatagcct ttcccttagt aaattattgt tgtcgactgt gattaagcct cctaattgta    3240
cccgccacgt ggcccgtgct gccagaatca agaagttttg actgtacctt ctgtatgtaa    3300
atgcaatggg ggaaaaatga tgaatggaag cttttgtcaa gcctgcaggc aacttgctgg    3360
ccaaaaaaaa aaaaaaaaaa aaaaaaaaaa aaaaa                               3395
```

<210> SEQ ID NO 2
<211> LENGTH: 890
<212> TYPE: PRT
<213> ORGANISM: Zea mays

<400> SEQUENCE: 2

```
Met Arg Lys Leu Phe Phe Ser Glu Ser Ala Cys Lys Glu Thr Lys Leu
1               5                   10                  15

His Cys Ala Pro His Ser Trp Leu Pro Leu Glu Arg Gly Lys Leu Ser
            20                  25                  30

Lys Phe Ser Gly His Ala Ala Ala Gly Ser Ser Ile Glu Ala Leu Met
        35                  40                  45

Lys Met Pro Glu Pro Ala Val Leu Pro Tyr Phe Lys Pro Ala Asn Tyr
    50                  55                  60

Val Asp Ile Leu Ala Gln Ile His Glu Glu Leu Glu Ser Cys Pro Pro
65                  70                  75                  80

Asp Glu Lys Ser Cys Leu Tyr Leu Leu Gln Phe Gln Val Phe Arg Gly
                85                  90                  95

Leu Gly Glu Ala Lys Leu Ser Arg Arg Ser Leu Gln Ser Ala Trp Glu
            100                 105                 110

Lys Ala Ser Thr Ile His Glu Lys Leu Ile Phe Gly Ala Trp Leu Lys
        115                 120                 125

Tyr Glu Lys Lys Gly Glu Glu Ala Ile Ser Asp Leu Leu Ser Ser Cys
    130                 135                 140
```

```
Cys Lys Cys Ser Gln Glu Phe Arg Leu Leu Asp Phe Val Ser Gln Val
145                 150                 155                 160

Ser Thr Gly Ser His Met Met Asn Tyr Asp Asp Asp Asp Glu Ser
                165                 170                 175

Asp Glu Phe Arg Gly Ser Ala Val Val His Phe Arg Ile Arg Asp Asp
            180                 185                 190

Met Ile Ala Cys Asp Arg Arg Lys Leu Ala Ala Leu Ser Thr Pro Leu
        195                 200                 205

Tyr Ala Met Leu Asn Gly Gly Phe Arg Glu Ser Tyr Leu Glu Val Ile
    210                 215                 220

Asp Met Ser Arg Asn Gly Ile Ser Pro Ile Gly Met Arg Ala Ile Ser
225                 230                 235                 240

Lys Phe Ser Leu Ser Gly Arg Leu Pro Tyr Leu Ser Ala Asp Ala Ile
                245                 250                 255

Leu Glu Met Leu Asp Phe Ala Asn Lys Phe Cys Cys Lys Gly Leu Lys
            260                 265                 270

Asp Ala Cys Glu Arg Lys Leu Ala Ser Phe Ile Ser Ser Arg Gln Asp
        275                 280                 285

Ala Ile Asp Phe Met Glu Cys Ala Leu Glu Leu Gly Cys Ser Ile Leu
    290                 295                 300

Ala Ala Ser Cys Leu Gln Val Leu Leu Asn Glu Leu Pro Glu Cys Leu
305                 310                 315                 320

Asn Asp Glu Gln Val Val Arg Ile Phe Ser Ser Ala Asn Lys Ala Gln
                325                 330                 335

Arg Leu Thr Met Val Gly Asn Ala Ser Phe Ser Leu Tyr Cys Leu Leu
            340                 345                 350

Ser Glu Val Ser Val Ser Thr Asn Pro Thr Ser Asp Val Thr Val Ser
    355                 360                 365

Phe Leu Glu Lys Leu Val Glu Ser Ala Ser Asp Ser Arg Gln Lys Gln
370                 375                 380

Leu Ala Leu His Gln Leu Ala Cys Thr Arg Phe Leu Arg Lys Asp Tyr
385                 390                 395                 400

Pro Glu Ser Glu Cys Leu Phe Asn Ala Ala Phe Ser Ala Gly His Leu
            405                 410                 415

Tyr Ser Leu Val Gly Leu Ala Arg Leu Ala Ser Leu Arg Gly Asn Lys
    420                 425                 430

His Phe Ala Leu Lys Leu Leu Asp Ser Val Met Ser Ser Arg Trp Pro
435                 440                 445

Leu Gly Trp Met Tyr Gln Glu Arg Ala Leu Tyr Leu Asp Gly Asp Asn
    450                 455                 460

Lys Leu Glu Asn Leu Asn Lys Ala Thr Glu Leu Asp Pro Thr Leu Thr
465                 470                 475                 480

Tyr Pro Tyr Met Phe Arg Ala Ala Ser Leu Met Lys Arg Gln Ser Val
                485                 490                 495

Glu Ala Ala Leu Met Glu Ile Asn Arg Ile Leu Gly Phe Lys Leu Val
            500                 505                 510

Leu Glu Cys Leu Glu Leu Arg Phe Cys Cys Tyr Leu Ala Leu Glu Asp
    515                 520                 525

Tyr Arg Ala Ala Leu Cys Asp Val Gln Ala Ile Leu Thr Leu Ala Pro
    530                 535                 540

Asp Tyr Arg Met Ile Gly Gly Arg Val Ala Ala Lys Gln Leu Arg Met
545                 550                 555                 560
```

```
Leu Val Leu Glu Asn Val Glu Gln Trp Thr Pro Ala Asp Cys Trp Met
                565                 570                 575

Gln Leu Tyr Asp Arg Trp Ser Ser Val Asp Asp Ile Gly Ser Leu Ser
            580                 585                 590

Val Ile Tyr Gln Met Leu Glu Ser Glu Thr Ala Lys Gly Val Leu Tyr
        595                 600                 605

Phe Arg Gln Ser Leu Leu Leu Arg Leu Asn Cys Pro Glu Ala Ala
    610                 615                 620

Met Arg Ser Leu Gln Leu Ala Arg Glu His Ala Ser Asp His Glu
625                 630                 635                 640

Arg Leu Val Tyr Glu Gly Trp Ile Leu Tyr Asp Thr Gly His Cys Glu
                645                 650                 655

Glu Gly Leu Gln Lys Ala Glu Ala Ser Ile Ala Ile Gln Arg Ser Phe
            660                 665                 670

Glu Ala Phe Phe Leu Lys Ala Tyr Ala Leu Ala Asp Ser Ser Leu Asp
        675                 680                 685

Pro Ser Thr Thr Ala Thr Val Val Ser Leu Leu Glu Asp Ala Leu Arg
    690                 695                 700

Cys Pro Ser Asp Arg Leu Arg Lys Gly Gln Ala Leu Asn Asn Leu Gly
705                 710                 715                 720

Ser Val Tyr Val Asp Cys Gly Lys Leu Asp Leu Ala Ala Glu Cys Tyr
                725                 730                 735

Ile Asn Ala Leu Lys Ile Gly His Thr Arg Ala His Gln Gly Leu Ala
            740                 745                 750

Arg Val His Phe Leu Arg Asn Asn Arg Val Gly Ala Tyr Asp Glu Met
        755                 760                 765

Thr Lys Leu Ile Glu Lys Ala Arg Asn Asn Ala Ser Ala Tyr Glu Lys
    770                 775                 780

Arg Ser Glu Tyr Cys Glu Arg Glu Leu Thr Lys Thr Asp Leu Gln Met
785                 790                 795                 800

Val Thr Lys Leu Asp Pro Leu Arg Val Tyr Pro Tyr Arg Tyr Arg Ala
                805                 810                 815

Ala Val Leu Met Asp Asn His Lys Glu Lys Glu Ala Val Ala Glu Leu
            820                 825                 830

Thr Arg Ala Ile Ala Phe Lys Ala Asp Leu Asn Leu Leu His Leu Arg
        835                 840                 845

Ala Ala Phe His Glu His Ile Gly Asp Ile Ser Ser Ala Leu Arg Asp
    850                 855                 860

Cys Arg Ala Ala Leu Leu Val Asp Pro Asn His Gln Glu Met Leu Glu
865                 870                 875                 880

Leu His His Arg Val Asn Ser Gln Glu Pro
            885                 890

<210> SEQ ID NO 3
<211> LENGTH: 3486
<212> TYPE: DNA
<213> ORGANISM: Zea mays

<400> SEQUENCE: 3 ccgccccca ccgcgctctc gccctccctc tccctctcta gcggtagatt ggtgctgttc      60
ccccctaatc ggtcggcggt tgggggccgg gttccgacgt ctgcccggga gctcgaccgg     120
gcctccgatc cgggctccca agccgccgcc tccggggcg cccctccgga attcttgctt     180
tctcgggctc cgaatctcgc cgcctgtcgt cgccagcggc tggcgcgggg gcttggttcc     240
```

```
cggcgtttca ttgcgaattc gggggcgatc tggggcccct ggtctggatg gcgaggattt      300
gagtggattc gagacgaaca agtggaggtg gagccctgat ctgggtggcg ccccgccgt       360 ggtatgtgcc atgaggaagc tcttcttctc cgagtcggcc tgcaaagaga ccaagcttca      420
ctccgcgccc cactcatggc tgccctcga gaggggaag ctctccaagt tctccggcca        480
tgccgccgcc ggctcctcca tagagtcctt gatgaagatg ccagagccgg ctgtgcttcc      540
gcacttcaag cccgcggact atgtcgacgt actggctcag atacacgagg agctggagtc      600 ctgccccct gacgacaagt cctccctgta cctcctccag tatcaggtct ccgtggcct       660 cggcgaggcc aagctgtctc ggaggagcct ccagtctgcg tgggagaagg ggagcaccat      720
acacgagaag ctcatcttcg gggcatggct caagtacgag aagaaagggg aggaggccat     780
ctccgacctg ctcagctcgt gcagcaagta cttgcaggag ttcaggctgc tggatttcgt     840
gttgcaggtc tccactgggt cacatgtgat aaactacgat ggtgatgatg atgagtttcg    900
gggttctgcg gtggttcatt tccggataag agatgatatg gttgcgtgcg atcgtcggaa    960
gctcgcggcg ctgtcaactc cactgtatgc aatgcttaac ggtggattta gggaatcata   1020
tctagaggtc attgacatgt ctagaaatgg tatctccct attggcatga gggcaatcag      1080
taaattcagc ctatcaggaa gactaccgta tttgtcagct gatgctatct ggagattct      1140 tgattttgcc aataagtttt gctgcaaggg cctcaaggat gcctgtgagc gaaagcttgc    1200
ttctttcgtc tcttcaaggc aagatgctat agacttcatg gagtgcgctc ttgagctggg   1260
ctgttccatc cttgctgctt catgcttgca agtgctcttg aatgagcttc cagagtgctt    1320
gaatgatgaa caagtggtta ggatattctc ttctgcaaat aaggcacaga gattgacaat    1380
ggttggcaat gcatctttct ccctatattg tcttcttagt gaagtctcca tgagtaccaa    1440
cccaacatcg gatgtcactg taagtttctt ggaaaagctg gtagagtcgg catcagattc    1500
taggcaaaat cagctggcct acatcagct ggcatgcacc aaatttctaa ggaaagatta     1560
ccctgaatct gagcgcctgt tcaatgctgc attttctgcc ggccatctct attcgatagt    1620
gggtttagct agattggcct ctctgagggg taataagcat tttgctctca gttgctaga    1680 ctctgtcatg tcatctcggt ggcctcttgg gtggatgtat caagagagag ctctatattt    1740
ggatggtgat aacaagttag aaaatcttaa caaggctact gagttggacc ctactcttac    1800
atatccctat atgttccgag ctgcatcttt gatgaaaagg caaagtgttg aagctgcatt    1860
gatggagatc aaccggatac ttggattcaa gctggtgctg gagtgcttag aactaaggtt    1920
ctgttgctac cttgcccttg aggattatag ggctgcctta tgtgacgtgc aggcaatact    1980
cactcttgcc ccagattatc gtatgattgg tggccgggtt gctgccaagc agctgagaat    2040
gctagtgcta gagaatgtag agcagtggac agctgctgac tgttggatgc agctttatga    2100
tcgctggtca tctgtggatg atataggggtc cctctctgtt atatatcaaa tgttggagtc   2160
agataccgcc aaaggagttt tgtactttag gcaatctttg cttcttctca gattaaactg    2220
tcctgaggcg gcaatgagga gtttgcagct tgctcgtgag catgctgcga gtgatcatga    2280
aaggcttgtc tatgaaggat ggatattgta tgatactggc cactgcgagg aaggattgca    2340
gaaggcagaa gcatccattg caatacaaag gtcatttgag gcattttttc tgaaagctta    2400
tgctttggct gattcgagtc ttgatccttc tacctcagca acagttgtat cacttctaga    2460
agatgcattg cggtgtccct cagatagact tcggaagggt caggctctaa acaacctcgg    2520
aagtgtttat gtggattgtg ggaagctaga acctggcagct gaatgctaca ttaatgcact   2580
aaagatcggt cacaccagag cgcatcaagg ccttgcaagg gttcatttcc tacggaacaa    2640
```

-continued

```
cagagctggt gcatacgacg aaatgaccaa gctgatagag aaggccagga acaacgcttc    2700
ggcatatgag aagagatccg agtactgtga ccggggagctg acgaaaacgg acctgcagat    2760
ggtcaccaaa ctcgaccctc tgcgagttta tccttacaga taccgtgctg ctgtgctgat    2820
ggacaaccac aaggagaaag aggcgatcgc ggagctgacc aaggccatcg ccttcaaggc    2880
ggacctgaac ctgctccacc tgcgcgcggc cttccacgag cacgtgggcg acgtctcgag    2940
cgccctccag gactgccgcg cggccctctc ggtggacccc aaccaccagg agatgctgga    3000
gcttcaccac cgggtgaaca gccaggaacc ctgagcgcgc tcccacggtg tacatacagg    3060
acaggaagcc cctcatcata gccaaccggc cataccggtg tatgttttgt accatacaca    3120
gcagatcaga tcaatgtaag gacacagtag aaagccacat tagatccctc cccttgaaaa    3180
ccaaacaccc cattccttgt gtccctaatt attagatata tatatgtgtt gtttgctata    3240
gcctcccctt agtaagttgt tgctgccgat tgtgattaag cctcctaatt gtacccgcca    3300
tgtgccccag cggcccgtgc ttccagaatc aagaagtttt gactgtacca tgtgtatgta    3360
agtgaaatgg gggaacaaag gatggtggaa gcttttgtcc gcgccaaact gtcaagcatg    3420
caggcacctg ttcttgccga gcacttgatt gattgcaaaa aaaaaaaaaa aaaaaaaaa     3480 aaaaaa                                                                3486
```

<210> SEQ ID NO 4
<211> LENGTH: 887
<212> TYPE: PRT
<213> ORGANISM: Zea mays

<400> SEQUENCE: 4

```
Met Arg Lys Leu Phe Phe Ser Glu Ser Ala Cys Lys Glu Thr Lys Leu
1               5                   10                  15

His Ser Ala Pro His Ser Trp Leu Pro Leu Glu Arg Gly Lys Leu Ser
            20                  25                  30

Lys Phe Ser Gly His Ala Ala Gly Ser Ser Ile Glu Ser Leu Met
        35                  40                  45

Lys Met Pro Glu Pro Ala Val Leu Pro His Phe Lys Pro Ala Asp Tyr
    50                  55                  60

Val Asp Val Leu Ala Gln Ile His Glu Glu Leu Glu Ser Cys Pro Pro
65                  70                  75                  80

Asp Asp Lys Ser Ser Leu Tyr Leu Leu Gln Tyr Gln Val Phe Arg Gly
                85                  90                  95

Leu Gly Glu Ala Lys Leu Ser Arg Arg Ser Leu Gln Ser Ala Trp Glu
            100                 105                 110

Lys Gly Ser Thr Ile His Glu Lys Leu Ile Phe Gly Ala Trp Leu Lys
        115                 120                 125

Tyr Glu Lys Lys Gly Glu Glu Ala Ile Ser Asp Leu Leu Ser Ser Cys
    130                 135                 140

Ser Lys Cys Leu Gln Glu Phe Arg Leu Leu Asp Phe Val Leu Gln Val
145                 150                 155                 160

Ser Thr Gly Ser His Val Ile Asn Tyr Asp Gly Asp Asp Glu Phe
                165                 170                 175

Arg Gly Ser Ala Val Val His Phe Arg Ile Arg Asp Asp Met Val Ala
            180                 185                 190

Cys Asp Arg Arg Lys Leu Ala Ala Leu Ser Thr Pro Leu Tyr Ala Met
        195                 200                 205

Leu Asn Gly Gly Phe Arg Glu Ser Tyr Leu Glu Val Ile Asp Met Ser
```

-continued

```
                210                 215                 220
Arg Asn Gly Ile Ser Pro Ile Gly Met Arg Ala Ile Ser Lys Phe Ser
225                 230                 235                 240

Leu Ser Gly Arg Leu Pro Tyr Leu Ser Ala Asp Ala Ile Leu Glu Ile
                245                 250                 255

Leu Asp Phe Ala Asn Lys Phe Cys Cys Lys Gly Leu Lys Asp Ala Cys
                260                 265                 270

Glu Arg Lys Leu Ala Ser Phe Val Ser Arg Gln Asp Ala Ile Asp
                275                 280                 285

Phe Met Glu Cys Ala Leu Glu Leu Gly Cys Ser Ile Leu Ala Ala Ser
        290                 295                 300

Cys Leu Gln Val Leu Leu Asn Glu Leu Pro Glu Cys Leu Asn Asp Glu
305                 310                 315                 320

Gln Val Val Arg Ile Phe Ser Ser Ala Asn Lys Ala Gln Arg Leu Thr
                325                 330                 335

Met Val Gly Asn Ala Ser Phe Ser Leu Tyr Cys Leu Leu Ser Glu Val
                340                 345                 350

Ser Met Ser Thr Asn Pro Thr Ser Asp Val Thr Val Ser Phe Leu Glu
        355                 360                 365

Lys Leu Val Glu Ser Ala Ser Asp Ser Arg Gln Asn Gln Leu Ala Leu
        370                 375                 380

His Gln Leu Ala Cys Thr Lys Phe Leu Arg Lys Asp Tyr Pro Glu Ser
385                 390                 395                 400

Glu Arg Leu Phe Asn Ala Ala Phe Ser Ala Gly His Leu Tyr Ser Ile
                405                 410                 415

Val Gly Leu Ala Arg Leu Ala Ser Leu Arg Gly Asn Lys His Phe Ala
                420                 425                 430

Leu Lys Leu Leu Asp Ser Val Met Ser Ser Arg Trp Pro Leu Gly Trp
        435                 440                 445

Met Tyr Gln Glu Arg Ala Leu Tyr Leu Asp Gly Asp Asn Lys Leu Glu
450                 455                 460

Asn Leu Asn Lys Ala Thr Glu Leu Asp Pro Thr Leu Thr Tyr Pro Tyr
465                 470                 475                 480

Met Phe Arg Ala Ala Ser Leu Met Lys Arg Gln Ser Val Glu Ala Ala
                485                 490                 495

Leu Met Glu Ile Asn Arg Ile Leu Gly Phe Lys Leu Val Leu Glu Cys
        500                 505                 510

Leu Glu Leu Arg Phe Cys Cys Tyr Leu Ala Leu Glu Asp Tyr Arg Ala
        515                 520                 525

Ala Leu Cys Asp Val Gln Ala Ile Leu Thr Leu Ala Pro Asp Tyr Arg
530                 535                 540

Met Ile Gly Gly Arg Val Ala Ala Lys Gln Leu Arg Met Leu Val Leu
545                 550                 555                 560

Glu Asn Val Glu Gln Trp Thr Ala Ala Asp Cys Trp Met Gln Leu Tyr
                565                 570                 575

Asp Arg Trp Ser Ser Val Asp Asp Ile Gly Ser Leu Ser Val Ile Tyr
        580                 585                 590

Gln Met Leu Glu Ser Asp Thr Ala Lys Gly Val Leu Tyr Phe Arg Gln
        595                 600                 605

Ser Leu Leu Leu Arg Leu Asn Cys Pro Glu Ala Ala Met Arg Ser
610                 615                 620

Leu Gln Leu Ala Arg Glu His Ala Ala Ser Asp His Glu Arg Leu Val
625                 630                 635                 640
```

```
Tyr Glu Gly Trp Ile Leu Tyr Asp Thr Gly His Cys Glu Glu Gly Leu
                645                 650                 655

Gln Lys Ala Glu Ala Ser Ile Ala Ile Gln Arg Ser Phe Glu Ala Phe
            660                 665                 670

Phe Leu Lys Ala Tyr Ala Leu Ala Asp Ser Ser Leu Asp Pro Ser Thr
        675                 680                 685

Ser Ala Thr Val Val Ser Leu Leu Glu Asp Ala Leu Arg Cys Pro Ser
690                 695                 700

Asp Arg Leu Arg Lys Gly Gln Ala Leu Asn Asn Leu Gly Ser Val Tyr
705                 710                 715                 720

Val Asp Cys Gly Lys Leu Asp Leu Ala Ala Glu Cys Tyr Ile Asn Ala
                725                 730                 735

Leu Lys Ile Gly His Thr Arg Ala His Gln Gly Leu Ala Arg Val His
            740                 745                 750

Phe Leu Arg Asn Asn Arg Ala Gly Ala Tyr Asp Glu Met Thr Lys Leu
        755                 760                 765

Ile Glu Lys Ala Arg Asn Asn Ala Ser Ala Tyr Glu Lys Arg Ser Glu
770                 775                 780

Tyr Cys Asp Arg Glu Leu Thr Lys Thr Asp Leu Gln Met Val Thr Lys
785                 790                 795                 800

Leu Asp Pro Leu Arg Val Tyr Pro Tyr Arg Tyr Arg Ala Ala Val Leu
                805                 810                 815

Met Asp Asn His Lys Glu Lys Glu Ala Ile Ala Glu Leu Thr Lys Ala
            820                 825                 830

Ile Ala Phe Lys Ala Asp Leu Asn Leu Leu His Leu Arg Ala Ala Phe
        835                 840                 845

His Glu His Val Gly Asp Val Ser Ser Ala Leu Gln Asp Cys Arg Ala
850                 855                 860

Ala Leu Ser Val Asp Pro Asn His Gln Glu Met Leu Glu Leu His His
865                 870                 875                 880

Arg Val Asn Ser Gln Glu Pro
                885

<210> SEQ ID NO 5
<211> LENGTH: 3763
<212> TYPE: DNA
<213> ORGANISM: Zea mays

<400> SEQUENCE: 5
ggcgggaggg cggggcgac  gcgcgcgcac cagccgttcc gccggagaac tcccgctctg      60
gcacgatcgt cgccgtgcga caggctgctg gccaaacgcg cgcgcgatag ccgaggggag     120
gaggacgtag aggagggta  agccggctgc ggaattcacc atgaccaata acttcctcac     180
gacgataaag agcctgaagc tgatcgaggg ttgcaaagcc gcacaattat acgccttaag     240
ctccgttggg gcagcctcca cgtccggctc ggggatgcc  ggaggagca  gcaacggcaa     300 gccccagcct cctccgccgc caaagaccat ctcgatgcgg tccggatcgc tgtactaccc     360
gcacgcggcg ccgtccacgt cgggcgcctt cgtgcccgag ccgcacctgc cgtgcggcct     420
cccggtggcc gacgccctcg agccggccct ggacgcgtgc ctgcgccccg tcgaccacgt     480
cggcgtgctc gccgcgtcgt accggcgggt ctcggccgcc acggcggggg cgacgacga      540 cctctgcgac gcgtacctgg agcagcacgc gctgttccag tcgatcggcg acgcgaggct     600
gatccggcgg gcgctgcggg ccgcgcgcgt ccacgcggac aacccgcacc ggcgcgccgt     660
```

```
gctcgccgcg tggctccggt acgagcgccg cgaggacgag ctcgacccgg cgccgccgcc    720
gctcgcgccc tgcaccgcga cgacgccgct gctcgagtgc ccccgcgccg ctgtcttcgc    780
cagcgtgtcc cactcccaca gcgtggaccc ggtctgcccg tgccgccgcc caccgcttcc    840
tccagtcacc cctccaccgc accgcctgag gcgcaacacg tcgggcgccg cctccgagat    900
gagcgaggag gaggagccgg agaccaatga cctgtggttc atcatcggcg aggaggaggt    960
agcgtgcgag cggtcgtgca tcgcggcgct ctcaaagccg ctcaacaccc tcctctacgg   1020
cgggttcgcc gaggcgcacc gcgaccggat cgacttctcc cgcgacggca tcacgccgcg   1080
cggcatgcgc gcggtctccg cctacagccg ccacggccgc gtggacgact cccgcccga    1140 cgtcatctcc cagctcctcg cattcgccaa caagttctgc tgcgagggcc tgaaggcagc   1200
ttgcgacaac cagctcgcgg ccatggtgcg gggtctcgac gacgcccggt ccctcatcga   1260
catcggcctc gaggaggcct cccacctcct cgtcgcctcc tgcctccagg cgttcctgcg   1320
ggagctcccc aagtcgctca cgtgcccgga catcgcgcgc tgctctgca gcccagaggg   1380 gcgagagcgc cttgacatct ccggtaacgc gtccttcgcg ctctaccact tcctctctta   1440
cgtcgccatg gagcaggaca tgaggtcgaa caccacggtg atgctgctgg agaggctgaa   1500
tgaattcgcg gagcagccat ggcagaagca gctggcactg caccagctcg ggtgcgtgat   1560
gctccagcgc ggcgagttcg aggaagcgca ggagtggttc gaggccgccg tcggcgaggg   1620
ccatgtgtac tcggtcgccg agaggcacg tgccaagtac aagcgcgggc acaagtacgc   1680
cgcgtacaag ctaatgaaca gtattctcgg cgagtacgac gaacccgccg ggtggatgta   1740
ccaagagcgc tccctgtact gtgtcggcaa ggagaagttg gctgatctgc aggcggcgac   1800
ggagctggac cctacgatga cattcccgta caaatatcgt gcgtgcgcgc tgctggagga   1860
ggacaatgct gcgtccgcga tcgcagagat cagcagggtc gtcggtttca agatggcgac   1920
cgattgcctt gagctccggg cgtggttcta ccttgcgctt gagcagtgcg agctggctgt   1980
gcaggacgtg agggcgatat tgacgttgga tccaacctac atgatgttcc acgggagaat   2040
gcacggggag cagctgattg agctcctccg aggacaggtg cagcagtggg atatggcgga   2100
ttgctggatg cagctgtacg gtcggtggtc ggcggtggat gacatcggct ctctggcggt   2160
tgtccagcag atgctctcca gggaacccgg aaacagcagc ttgcggtttc gacagtcact   2220
tctccttcta aggctaaact gtcagaaagc tgccatgcgc agtttgcgat atgctcggaa   2280
cagcacgctc catgagcatg agaggctcgt atacgaaggg tggattctgt atgacagtgg   2340
gcatcgcgac gaagcgttag ccaaggccga gcagtcgatc ggactccaga gatcattcga   2400
agccttcttc ctcaaggcgt acgccttagg agattctagc cttgacacgg aatcctcgct   2460
ctccgtggtc cagcttctgg aacatgccaa cagctgtgct tccgacaacc ttcgcaaggg   2520
gcaggcatac aacaacatgg ggagcatcta cgtggactgt gacatgctgg acgaggctgc   2580
cgagtgctac ggcatcgcgc tgaacataaa gcacacacgg cgcatcagg cctagctcg    2640 agtccactac ttgaaaaaca ggaaaaaggt tgcgtttgag gagatgacga agctcgtgga   2700
gattgccagc aactgcgcgt cggcgtatga aaagcggtcg gaatacggtg agcgcgaagc   2760
tgcgaggagc gacctgaaca tggcgacgct tcttgatcct accaggactt atccttacag   2820
atacagagca gctgtactga tggacgaggg caaggaggag gaggcgatcg cggagctgtc   2880
aggagccata gctttcaagc cggacctcca gctgctgcac ctccgcgcgg cgttcttcga   2940
ctccatgggc gagcgcgaga gcgccctgcg ggactgcgag gccgcgctct gcctggaccc   3000
gacccacggc gacacattgg agctgtacag caaagcctcc accaccaagg ccgaaccccca  3060
```

```
gagctaggca gccagccggc cggccggccg gcaggccgcc gctctcctcg tcgtcgattc   3120
agctgcggtt tttgcgaggc aggatgatga gacgatctct tctctactct catgggtgg    3180 aagctgcaga tcagtgaggc aggagcaccg gaacatgcac atatctcttc taagagtata   3240
tacaagagcc ttagttctgt tactgttaga gttggacatg ggaggcagc accgcaggag    3300 attgagtgcg tgttgcctta agggtagact gcgcaggtga ggtgacaaag agcatgcact   3360
gcactgcact gcaccacata tgtgcatcca aggttgaaga cgaccagcac ctccggtcag   3420
aagagaggaa ggagaggcgg ctggagaatg agagccaggt cagcagggtg tgcaaaccgc   3480
cggcggtacc aacgaatctt cctcttttc ttcttttgct tgaatttatg ccttgtgacg     3540
tgcatctgga ggcacgactg attacaaaag aatacgagtt ttttaaagt aacgcagcgc    3600 gaaagggaag attcttcctg ctgccgactg cacgctgtat tatgtatgag tcgtggctcc   3660
gtcgtgcctc cagctaacga ggccctgaca tgcatctgct gcattgctac acgttcgttc   3720
gtgttcacaa ctacgctttg ttctttcgtt ccaattccaa atc                     3763
```

```
<210> SEQ ID NO 6
<211> LENGTH: 968
<212> TYPE: PRT
<213> ORGANISM: Zea mays

<400> SEQUENCE: 6

Met Thr Asn Asn Phe Leu Thr Thr Ile Lys Ser Leu Lys Leu Ile Glu
1               5                   10                  15

Gly Cys Lys Ala Ala Gln Leu Tyr Ala Leu Ser Ser Val Gly Ala Ala
            20                  25                  30

Ser Thr Ser Gly Ser Gly Asp Ala Gly Gly Ser Ser Asn Gly Lys Pro
        35                  40                  45

Gln Pro Pro Pro Pro Lys Thr Ile Ser Met Arg Ser Gly Ser Leu
    50                  55                  60

Tyr Tyr Pro His Ala Ala Pro Ser Thr Ser Gly Ala Phe Val Pro Glu
65                  70                  75                  80

Pro His Leu Pro Cys Gly Leu Pro Val Ala Asp Ala Leu Glu Pro Ala
                85                  90                  95

Leu Asp Ala Cys Leu Arg Pro Val Asp His Val Gly Val Leu Ala Ala
            100                 105                 110

Ser Tyr Arg Arg Val Ser Ala Ala Thr Ala Gly Gly Asp Asp Leu
        115                 120                 125

Cys Asp Ala Tyr Leu Glu Gln His Ala Leu Phe Gln Ser Ile Gly Asp
    130                 135                 140

Ala Arg Leu Ile Arg Arg Ala Leu Arg Ala Arg Val His Ala Asp
145                 150                 155                 160

Asn Pro His Arg Arg Ala Val Leu Ala Ala Trp Leu Arg Tyr Glu Arg
                165                 170                 175

Arg Glu Asp Glu Leu Asp Pro Ala Pro Pro Leu Ala Pro Cys Thr
            180                 185                 190

Ala Thr Thr Pro Leu Leu Glu Cys Pro Arg Ala Ala Val Phe Ala Ser
        195                 200                 205

Val Ser His Ser His Ser Val Asp Pro Val Cys Pro Cys Arg Arg Pro
    210                 215                 220

Pro Leu Pro Pro Val Thr Pro Pro His Arg Leu Arg Arg Asn Thr
225                 230                 235                 240

Ser Gly Ala Ala Ser Glu Met Ser Glu Glu Glu Glu Pro Glu Thr Asn
```

```
                    245                 250                 255
Asp Leu Trp Phe Ile Ile Gly Glu Glu Val Ala Cys Glu Arg Ser
            260                 265                 270

Cys Ile Ala Ala Leu Ser Lys Pro Leu Asn Thr Leu Leu Tyr Gly Gly
            275                 280                 285

Phe Ala Glu Ala His Arg Asp Arg Ile Asp Phe Ser Arg Asp Gly Ile
290                 295                 300

Thr Pro Arg Gly Met Arg Ala Val Ser Ala Tyr Ser Arg His Gly Arg
305                 310                 315                 320

Val Asp Asp Phe Pro Pro Asp Val Ile Ser Gln Leu Leu Ala Phe Ala
                325                 330                 335

Asn Lys Phe Cys Cys Glu Gly Leu Lys Ala Ala Cys Asp Asn Gln Leu
            340                 345                 350

Ala Ala Met Val Arg Gly Leu Asp Asp Ala Arg Ser Leu Ile Asp Ile
            355                 360                 365

Gly Leu Glu Glu Ala Ser His Leu Leu Val Ala Ser Cys Leu Gln Ala
        370                 375                 380

Phe Leu Arg Glu Leu Pro Lys Ser Leu Thr Cys Pro Asp Ile Ala Arg
385                 390                 395                 400

Leu Leu Cys Ser Pro Glu Gly Arg Glu Arg Leu Asp Ile Ser Gly Asn
                405                 410                 415

Ala Ser Phe Ala Leu Tyr His Phe Leu Ser Tyr Val Ala Met Glu Gln
            420                 425                 430

Asp Met Arg Ser Asn Thr Thr Val Met Leu Leu Glu Arg Leu Asn Glu
            435                 440                 445

Phe Ala Glu Gln Pro Trp Gln Lys Gln Leu Ala Leu His Gln Leu Gly
        450                 455                 460

Cys Val Met Leu Gln Arg Gly Glu Phe Glu Ala Gln Glu Trp Phe
465                 470                 475                 480

Glu Ala Ala Val Gly Glu Gly His Val Tyr Ser Val Ala Gly Glu Ala
                485                 490                 495

Arg Ala Lys Tyr Lys Arg Gly His Lys Tyr Ala Ala Tyr Lys Leu Met
            500                 505                 510

Asn Ser Ile Leu Gly Glu Tyr Asp Glu Pro Ala Gly Trp Met Tyr Gln
        515                 520                 525

Glu Arg Ser Leu Tyr Cys Val Gly Lys Glu Lys Leu Ala Asp Leu Gln
            530                 535                 540

Ala Ala Thr Glu Leu Asp Pro Thr Met Thr Phe Pro Tyr Lys Tyr Arg
545                 550                 555                 560

Ala Cys Ala Leu Leu Glu Glu Asp Asn Ala Ala Ser Ala Ile Ala Glu
                565                 570                 575

Ile Ser Arg Val Val Gly Phe Lys Met Ala Thr Asp Cys Leu Glu Leu
            580                 585                 590

Arg Ala Trp Phe Tyr Leu Ala Leu Glu Gln Cys Glu Leu Ala Val Gln
        595                 600                 605

Asp Val Arg Ala Ile Leu Thr Leu Asp Pro Thr Tyr Met Met Phe His
        610                 615                 620

Gly Arg Met His Gly Glu Gln Leu Ile Glu Leu Leu Arg Gly Gln Val
625                 630                 635                 640

Gln Gln Trp Asp Met Ala Asp Cys Trp Met Gln Leu Tyr Gly Arg Trp
                645                 650                 655

Ser Ala Val Asp Asp Ile Gly Ser Leu Ala Val Val Gln Gln Met Leu
            660                 665                 670
```

```
Ser Arg Glu Pro Gly Asn Ser Ser Leu Arg Phe Arg Gln Ser Leu Leu
            675                 680                 685

Leu Leu Arg Leu Asn Cys Gln Lys Ala Ala Met Arg Ser Leu Arg Tyr
690                 695                 700

Ala Arg Asn Ser Thr Leu His Glu His Glu Arg Leu Val Tyr Glu Gly
705                 710                 715                 720

Trp Ile Leu Tyr Asp Ser Gly His Arg Asp Glu Ala Leu Ala Lys Ala
                725                 730                 735

Glu Gln Ser Ile Gly Leu Gln Arg Ser Phe Glu Ala Phe Phe Leu Lys
            740                 745                 750

Ala Tyr Ala Leu Gly Asp Ser Ser Leu Asp Thr Glu Ser Ser Leu Ser
            755                 760                 765

Val Val Gln Leu Leu Glu His Ala Asn Ser Cys Ala Ser Asp Asn Leu
770                 775                 780

Arg Lys Gly Gln Ala Tyr Asn Asn Met Gly Ser Ile Tyr Val Asp Cys
785                 790                 795                 800

Asp Met Leu Asp Glu Ala Ala Glu Cys Tyr Gly Ile Ala Leu Asn Ile
                805                 810                 815

Lys His Thr Arg Ala His Gln Gly Leu Ala Arg Val His Tyr Leu Lys
            820                 825                 830

Asn Arg Lys Lys Val Ala Phe Glu Glu Met Thr Lys Leu Val Glu Ile
            835                 840                 845

Ala Ser Asn Cys Ala Ser Ala Tyr Glu Lys Arg Ser Glu Tyr Gly Glu
850                 855                 860

Arg Glu Ala Ala Arg Ser Asp Leu Asn Met Ala Thr Leu Leu Asp Pro
865                 870                 875                 880

Thr Arg Thr Tyr Pro Tyr Arg Tyr Arg Ala Ala Val Leu Met Asp Glu
                885                 890                 895

Gly Lys Glu Glu Glu Ala Ile Ala Glu Leu Ser Gly Ala Ile Ala Phe
            900                 905                 910

Lys Pro Asp Leu Gln Leu Leu His Leu Arg Ala Ala Phe Phe Asp Ser
            915                 920                 925

Met Gly Glu Arg Glu Ser Ala Leu Arg Asp Cys Glu Ala Ala Leu Cys
930                 935                 940

Leu Asp Pro Thr His Gly Asp Thr Leu Glu Leu Tyr Ser Lys Ala Ser
945                 950                 955                 960

Thr Thr Lys Ala Glu Pro Gln Ser
                965

<210> SEQ ID NO 7
<211> LENGTH: 3477
<212> TYPE: DNA
<213> ORGANISM: Zea mays

<400> SEQUENCE: 7
cttcctgctc tcgctgagcc tgcaggatct gaatccgagc tcgctcgcat ccactatctg      60
caggccccac gcgccctgtt ccttcctccc gctaacaatc gccctgttcc cggtttgatc     120
cgttgaattc tgcccggcgc gcgggggctt gcgggtgcgc accggaggct gcatcttttc     180
ccggccaaga ttcggtccgg tggggccgtt cttggcacga tttcacgggc cgtttggcct     240
tccctcgccg gatttgttcc ggctccaggc accaaattcc aatcttttcc tgctgctgct     300
gcctctgcga cactttattc ttctccccca attagcggcg gttagtgtgg attctgattt     360
gtaggttcat ttcctggttt cctccgtgag cttctgcggt tggcgtggtt acgccagtcc     420
```

```
ctcgcgattt acatctgtga ttcgtttgaa aatctgggag tgtggagatt tgggaggtct    480
tctcgctcct gtgctctatg aggagcagct tcctgtcgga gtcgccgtgc gacgagcagc    540
gcatccatgg atatggtttc aacccgcagt catggctgca ggtggagcga gggaagctgc    600
ccaagtcgtc ctactcgcct tcctccattg agtcacttat caagattgct gagccacatg    660
tagtgccatt gtataagcct ttggattatg ttgaggtgct gtcaaggatc cacgaggagc    720
ttgaacaatg taggccgagc gagctgccag gcctgtactt ggtccagtcc caggtgtttc    780
ggggccttgg agaagcaaaa ttgcgccaga ggagcctcca ctctgcctgg cgttgtgcaa    840
gcagcgtcca tgagaaagtc atatttgggg catggttgcg gtacgagaag caggggagg     900
agatcatatc tgacgtcctt gcatcatgtc agaaatgctg tcgagagttt ggtttacttg    960
atgttgcctc tgagatgcct gtgcggaatt ttgaggtaat tggttcatgg agacaggct   1020
cctcgtctca gtttcttcc atggtaacct tccaaataca ggatggtagg gtgacatgtg   1080
ataggtgcaa gattgcgtct ttgtcaatac cattttgctc catgcttaat ggaccgttca   1140
atgagtcaca gcttgagctt gttgatttgt cagagaatgg tatttcgttg gagggcatga   1200
gagctgtttc tgagtttagt tctacatgta gtttagggga tcttcctgtg gaaatcttat   1260
tggagatcct ggtgtttgca aacacatttt gttgtgacag gctaaaagat gcttgtgata   1320
ggaaactggc ttcatttgtt tcaacaaggc aggatgctgt tgagctcatg ccgttggcat   1380
ttgaagaaaa tgcgccagtt cttgctgctt cttgcttgca aatttttta caggaacttc   1440
ccaattgtct agctgatgat ctagtaatta gcctcttctt aggtgcaact gcacaacaac   1500
aacttatcat ggttggacat gcatccttt tgctgtactg cttgcttagt gaagtagcaa   1560
tgaacattga tccgaggaca gaaacaactg tattattgtt agagaagctt gtgcagctag   1620
cagttacccc tactcagaag caaatagctt ttcatcaact tgcatgcatt agactttga   1680
gaaaggaata tagtgaagct gaacaccaat ttgaggttgc cttctctgcc ggtcatgtgt   1740
attcaattgc tggtattgct agagtcgctg gcattcaagg ccaaaaggct ttggcttatg   1800
agaagctcag ttcagtgata acatcaaatt tgccactggg gtggatgtat ctggagaggt   1860
ctttgtattc tgaaggtgat agaaagctgg cagaccttga caaagcaagc gagctggatc   1920
ctactctcac ttaccttac atgtatcgag ctgcatcctt gatgagaaaa aaagatgcta   1980
aacatgcctt agaggaaatt aaccgactct tgggtttcaa gttagcattg gagtgcctgg   2040
agctacggat ctgtctatac ctggctcttg aagactataa gtctgctatc tgtgatatcc   2100
atgcgattct tactctttca cctgattatc ggatgttgga aggacgtgta gctgcttcca   2160
aaataggcac tcttcttggt gcacatgtcg agcagtggaa tacggctgag tgttggctac   2220
aactttatga gcgctggtca tcagttgatg atattggctc cctttcagtg atctatcgga   2280
tgcttgagtc agatgcagca aaaggtgtcc tctactttag gcaatctttg ctgctcctta   2340
ggttgaactg tcccgaggca gcgatgcgca gtttgcaatt ggcaaggcat catgcagcaa   2400
ctgagcatga acgactagta tatgagggt ggctcttata tgacacgggg cactatgggg    2460
aggccctaca aaagcggaa gaatctattt ccattcaaag atcatttgaa gctttctttc    2520
tgaaagccta tgttttggct gattcaggag ttgatccttc ttattctgcg acagttatct   2580
cacttcttga agatgcattg aaatgccctt cagaccggct tcggaagggt caggcattga   2640
ataaccttgg tggtgtctat gttgattgtg gaaagttaga ttcagcagct gattgctata   2700
caagtgcatt gaaaattcga cacactagag cccatcaagg tcttgctcgt gtacatttc    2760
```

-continued

```
tgaggaacaa cagggaagct gcatatgaag agatgacaaa gttgatagaa aaagctaaaa   2820
acaatgcttc ggcttatgag aaacgctcag aatattgtga acgagaacaa actatgacag   2880
atttgcaaac agtgacccaa ttggatcctt tgcgtgttta tccatacaga tatcgagcag   2940
cagtgctgat ggatagccac aaggagaatg atgcaatagc ggagctcagc cgtgcgatat   3000
ccttcaaagc ggacctgcat ttgctgcatc tccgtgcggc tttccacgag cacattggag   3060
atgtacccag cgctctccgt gattgtgag ccgccctctc cttggacccg aatcaccagg    3120
agatgttgga gcttcagaaa cgtgtgaaca gccaagagcc ctgacacatt gtggtgctgt   3180
attgtgtatt gtacaccacg actcatgcca ctttggtttg cctcgtgaca dacagccttg    3240
acctgattca ttttttttc gttttccgt taattaatta atcaatcact gtaatacgaa      3300
gttttcagga agaaagtaac agagagcaag agagagaact agttatatga aagcaggcat   3360
tgataaagcc ttttaactc gatgcctgtg gcctctgtag aagtattgtg ctaatccctg     3420
aactgtatct tgaaaagtg attcgtgcat aatgtatttt tcagttctgt tctcttt       3477
```

<210> SEQ ID NO 8
<211> LENGTH: 888
<212> TYPE: PRT
<213> ORGANISM: Zea mays

<400> SEQUENCE: 8

```
Met Arg Ser Ser Phe Leu Ser Glu Ser Pro Cys Asp Glu Gln Arg Ile
1               5                   10                  15

His Gly Tyr Gly Phe Asn Pro Gln Ser Trp Leu Gln Val Glu Arg Gly
            20                  25                  30

Lys Leu Pro Lys Ser Ser Tyr Ser Pro Ser Ser Ile Glu Ser Leu Ile
        35                  40                  45

Lys Ile Ala Glu Pro His Val Val Pro Leu Tyr Lys Pro Leu Asp Tyr
    50                  55                  60

Val Glu Val Leu Ser Arg Ile His Glu Leu Glu Gln Cys Arg Pro
65                  70                  75                  80

Ser Glu Leu Pro Gly Leu Tyr Leu Val Gln Ser Gln Val Phe Arg Gly
                85                  90                  95

Leu Gly Glu Ala Lys Leu Arg Gln Arg Ser Leu His Ser Ala Trp Arg
            100                 105                 110

Cys Ala Ser Ser Val His Glu Lys Val Ile Phe Gly Ala Trp Leu Arg
        115                 120                 125

Tyr Glu Lys Gln Gly Glu Glu Ile Ile Ser Asp Val Leu Ala Ser Cys
    130                 135                 140

Gln Lys Cys Cys Arg Glu Phe Gly Leu Leu Asp Val Ala Ser Glu Met
145                 150                 155                 160

Pro Val Arg Asn Phe Glu Val Ile Gly Ser Trp Glu Thr Gly Ser Ser
                165                 170                 175

Ser Gln Val Ser Ser Met Val Thr Phe Gln Ile Gln Asp Gly Arg Val
            180                 185                 190

Thr Cys Asp Arg Cys Lys Ile Ala Ser Leu Ser Ile Pro Phe Cys Ser
        195                 200                 205

Met Leu Asn Gly Pro Phe Asn Glu Ser Gln Leu Glu Leu Val Asp Leu
    210                 215                 220

Ser Glu Asn Gly Ile Ser Leu Glu Gly Met Arg Ala Val Ser Glu Phe
225                 230                 235                 240

Ser Ser Thr Cys Ser Leu Gly Asp Leu Pro Val Glu Ile Leu Leu Glu
                245                 250                 255
```

```
Ile Leu Val Phe Ala Asn Thr Phe Cys Cys Asp Arg Leu Lys Asp Ala
                260                 265                 270

Cys Asp Arg Lys Leu Ala Ser Phe Val Ser Thr Arg Gln Asp Ala Val
            275                 280                 285

Glu Leu Met Pro Leu Ala Phe Glu Glu Asn Ala Pro Val Leu Ala Ala
        290                 295                 300

Ser Cys Leu Gln Ile Phe Leu Gln Glu Leu Pro Asn Cys Leu Ala Asp
305                 310                 315                 320

Asp Leu Val Ile Ser Leu Phe Leu Gly Ala Thr Ala Gln Gln Gln Leu
                325                 330                 335

Ile Met Val Gly His Ala Ser Phe Leu Leu Tyr Cys Leu Leu Ser Glu
            340                 345                 350

Val Ala Met Asn Ile Asp Pro Arg Thr Glu Thr Thr Val Leu Leu Leu
        355                 360                 365

Glu Lys Leu Val Gln Leu Ala Val Thr Pro Thr Gln Lys Gln Ile Ala
    370                 375                 380

Phe His Gln Leu Ala Cys Ile Arg Leu Leu Arg Lys Glu Tyr Ser Glu
385                 390                 395                 400

Ala Glu His Gln Phe Glu Val Ala Phe Ser Ala Gly His Val Tyr Ser
                405                 410                 415

Ile Ala Gly Ile Ala Arg Val Ala Gly Ile Gln Gly Lys Ala Leu
            420                 425                 430

Ala Tyr Glu Lys Leu Ser Ser Val Ile Thr Ser Asn Leu Pro Leu Gly
        435                 440                 445

Trp Met Tyr Leu Glu Arg Ser Leu Tyr Ser Glu Gly Asp Arg Lys Leu
    450                 455                 460

Ala Asp Leu Asp Lys Ala Ser Glu Leu Asp Pro Thr Leu Thr Tyr Pro
465                 470                 475                 480

Tyr Met Tyr Arg Ala Ala Ser Leu Met Arg Lys Asp Ala Lys His
                485                 490                 495

Ala Leu Glu Glu Ile Asn Arg Leu Leu Gly Phe Lys Leu Ala Leu Glu
            500                 505                 510

Cys Leu Glu Leu Arg Ile Cys Leu Tyr Leu Ala Leu Glu Asp Tyr Lys
        515                 520                 525

Ser Ala Ile Cys Asp Ile His Ala Ile Leu Thr Leu Ser Pro Asp Tyr
530                 535                 540

Arg Met Leu Glu Gly Arg Val Ala Ala Ser Lys Ile Gly Thr Leu Leu
545                 550                 555                 560

Gly Ala His Val Glu Gln Trp Asn Thr Ala Glu Cys Trp Leu Gln Leu
                565                 570                 575

Tyr Glu Arg Trp Ser Ser Val Asp Asp Ile Gly Ser Leu Ser Val Ile
            580                 585                 590

Tyr Arg Met Leu Glu Ser Asp Ala Ala Lys Gly Val Leu Tyr Phe Arg
        595                 600                 605

Gln Ser Leu Leu Leu Leu Arg Leu Asn Cys Pro Glu Ala Ala Met Arg
    610                 615                 620

Ser Leu Gln Leu Ala Arg His His Ala Ala Thr Glu His Glu Arg Leu
625                 630                 635                 640

Val Tyr Glu Gly Trp Leu Leu Tyr Asp Thr Gly His Tyr Gly Glu Ala
                645                 650                 655

Leu Gln Lys Ala Glu Glu Ser Ile Ser Ile Gln Arg Ser Phe Glu Ala
            660                 665                 670
```

```
Phe Phe Leu Lys Ala Tyr Val Leu Ala Asp Ser Gly Val Asp Pro Ser
            675                 680                 685

Tyr Ser Ala Thr Val Ile Ser Leu Leu Glu Asp Ala Leu Lys Cys Pro
        690                 695                 700

Ser Asp Arg Leu Arg Lys Gly Gln Ala Leu Asn Asn Leu Gly Val
705                 710                 715                 720

Tyr Val Asp Cys Gly Lys Leu Asp Ser Ala Ala Asp Cys Tyr Thr Ser
                725                 730                 735

Ala Leu Lys Ile Arg His Thr Arg Ala His Gln Gly Leu Ala Arg Val
            740                 745                 750

His Phe Leu Arg Asn Asn Arg Glu Ala Ala Tyr Glu Glu Met Thr Lys
        755                 760                 765

Leu Ile Glu Lys Ala Lys Asn Asn Ala Ser Ala Tyr Glu Lys Arg Ser
    770                 775                 780

Glu Tyr Cys Glu Arg Glu Gln Thr Met Thr Asp Leu Gln Thr Val Thr
785                 790                 795                 800

Gln Leu Asp Pro Leu Arg Val Tyr Pro Tyr Arg Tyr Arg Ala Ala Val
                805                 810                 815

Leu Met Asp Ser His Lys Glu Asn Asp Ala Ile Ala Glu Leu Ser Arg
            820                 825                 830

Ala Ile Ser Phe Lys Ala Asp Leu His Leu Leu His Leu Arg Ala Ala
        835                 840                 845

Phe His Glu His Ile Gly Asp Val Pro Ser Ala Leu Arg Asp Cys Arg
    850                 855                 860

Ala Ala Leu Ser Leu Asp Pro Asn His Gln Glu Met Leu Glu Leu Gln
865                 870                 875                 880

Lys Arg Val Asn Ser Gln Glu Pro
                885

<210> SEQ ID NO 9
<211> LENGTH: 4548
<212> TYPE: DNA
<213> ORGANISM: Glycine max

<400> SEQUENCE: 9
atgcaacaca gcatcttcgc ctcaatgcgt agcttgaaga tcatggacgg ttgcaagggc      60
actcaggtct acgccatcaa cccctccagc gccaccggcg gtggaattgg cgagaagctt     120
ctccaacagc ttcacgacca catcaaaagc cacacccta gaaccaaatc ggttcggaac      180
ttacaacctc cgaacatgac gacgccgtcg gaggttttcg tctccgacgg gtcgctcctt     240
ccttacggcc tccccatgac ggacctccta gagcccaaaa ttgaaccctc cttggtgtcg     300
gtggattttg tcgaaacccct cgccggagtc taccgccgca ccgaggaccg ccaccagttc     360
gaccgctccg aggtgtacct cgagcaatgc gcggtattcc aggggctggc cgacccgaag     420
ctcttccgcc gcagcctccg cgccgcccgg cagcacgcca tcaacgtgca cgcgaaggtc     480
gtgctttccg catggcttcg ctacgagcgc cgcgaggatg agctcatcgg ctcgtccttg     540
atggactgca gcggaggaa cctcgagtgc ccccgcacca cgctggttcc aggctacgac     600
ccggagttgg tgtttgattc ctgcgcgtgc acgggtgcac gcgcaggtaa tggtgataac     660
gataatgatg atgcaatggc aatagtggtt gatgagcaat gctccacctc ggaagaggag     720
gaggaggatg gtgacatgtc tttttgtgtt ggtgatgatg agattaagtg taataggttc     780
aatatagcct cactttcaag gccctttaag ataatgttgt atggtggatt cattgagtca     840
acgagagaga agataaattt ttcgcggaat tgttttctg ttgaggcatt gagggctgct     900
```

-continued

```
gaggtgttca gtaggagaaa gaggttgagt catttggagc ccaaggttat tttggagttg     960
ctatctttgg caaaccggtt ttgttgcgag gagatgaaga atgcttgtga cgcgcatttg    1020
gcatcgcttg tttgtgacat agacgatgcc ttgttgcttg ttgagtatgg actggaggag    1080
accgcatacc tgctggtggc tgcctgcttg caggtgtttc tccgggagct ccctggttcg    1140
atgcaaagtt tgagtgttgt gaagatattt tgtagtccgg agggtaggga taggcttgct    1200
ctggcggggc acgcgtcgtt tgtgttgtat tattttttga gtcagattgc gatggaggaa    1260
gagatgaggt cgaacaccac tgtgatgctg ttggagaggt tagtggagtg cgcaaaggat    1320
ggttgggaga agcaagttgc gtttcatcta ttgggtgttg ttatgcttga gagaaaagaa    1380
tacaaagatg cacaatattg gtttcaggca gcggttgatg cagggcatgc ttattctttg    1440
gtgggagttg caagggcaaa atataagcgt ggtcacacat attcagcata taagttgatg    1500
aactcactta tttctgatca taaaccggtt gggtggatgt atcaggaaag gtctttgtat    1560
tgtgttggga aggagaaatt gatggacttg atgtctgcaa ctgagttaga tccaactctt    1620 tccttttccat ataaattccg ggctgtttct ttcctggagg aaaacaagat tggacctgcc    1680
attgcagaaa tcaataaaat aattggcttc aaggtttctc ctgattgcct tgaattgaga    1740
gcttggttct tgattgccat ggaagattat gaaggagccc tcagggatgt ccgggcaatt    1800
ttgacattgg atccaaatta tatgatgttc tatgggcata tgcacggtga tcagttggta    1860
gaacttctcc aacctttttgt tcagcagtgg agtcaggctg attgctggat tcagttgtat    1920
gaccgatggt cctctgttga tgatattggt tcttttggctg ttgtacacca gatgttagca    1980
aaagacccgg ggaaaagtct tttatgctttt cggcaatctc tccttcttct acggtgagtg    2040
taatccctac attaattcag ttatatctta tttcattagt gagttctgat atagattcta    2100
gtttgactta ataattttct ccatgcatga attctctgcg aatgaattgc ctactgtggg    2160
ctgttttata cttttcctat tatcagtgac gagtaatatc aaagtctggc tagaaatatt    2220
ttgttgatcc ttttccttttt taactggcca tatacctgca tgggattcat gtttctattt    2280
gctgcaaaac aaactagttt atagtcacat tttattatat caaaattaga gaaaattgtc    2340
acatgttcca cccatcaaag caaactatgg taaactaatg aaactgcaga tcatttttat    2400
tgtgtactgg ccaggatcta cattgaggta tttattatgt aatttgccaa aagctaccca    2460 catttttatgt atagtttcat aaatattagt ccaggaggtg actttcagtt attgtatctt    2520
ctctgctttc agaatgaatg gaaactgata agtactttga aaaactagtt ggctgtgttt    2580
taatacttat tctatctttt ttagttatgt acttttttgct agttttttcct tttagaaagt    2640 gttgatactt gattgttatt aacttagata gctaatttgt cttagtcctg gttcattttta    2700 atgccagagc ttgactatta tgggtgttga ttttcctgaa tcttgtaggt tgaattgtcc    2760
aaagtctgcc atgcgtagtt tgcggctggc tagaaatcat tctacttctg atcatgaaag    2820
gcttgtgtat gaaggatgga tactgtatga cactggttat cgtgaagaag cattagcaaa    2880
ggctgaggaa tctatttcta ttcgaagatc atttgaagct tactttctca aagcttatgc    2940
gttagctgac tcaaatcttg attcagagtc ttcaaagtat gtgatctgtc tcttggagga    3000
agctcttaga tgccctttag atggtcttcg gaaaggacaa gtgagtgcta agttttggat    3060
taaacatttt atgctgatat cagtgctgaa gtaatgtatt tatatttgtt attcttttaa    3120
attgtaggca ctgaataatc tagggagtgt ctatgtagac tgtgataaac tggaccttgc    3180
tgctgactgc tacatgaatg cactcaacat caagcataca cgagcacatc aggggttggc    3240
```

```
acgtgtatat catcttaaaa atctccggaa agcagcatat gatgagatga caaagctaat    3300
agaaaaggct cggagtaatg catcagctta tgagaaacgt tcagaatatt gcgaccgtga    3360
catggcaaag agtgatctta gtatggcatc acaattggat cctctaagga cttatcctta    3420
ccgatatagg gctgcaggtg agtctcatat gagtggttct attatcccgt gttttctcct    3480
gattattcat gatggtaact tggtgaggga ggggaattgt agctgtgatt gtaatttgca    3540
agccattttt gtgtttcaaa tattatctgt ggcatttgta tagccatgat ggttttatta    3600
ctgtcttaga ttccagggta caatcttcaa tgctgttgtt ttttaccaaa ttttttccta    3660
taaactgatt tgtctgcata acttcataga catattttag ttttccatga aaaaaatagt    3720
agttgatgac tttccttaga tttactatgt aacatttaaa tgaatgaaaa atcactgtgt    3780
ttatctttct gctttctttg tttacttgtt tatataccccc aactcaaatg ccaaatgttt    3840
atgttgacca cccatgattt atttaagttt cccctctaaa aatgcttttt gtctgaattt    3900
gtggcattaa tcatgcagtt actcagaaac attatattgc ataagtattg caggaaatga    3960
cttgtggaat tttcacagtt atgcagtaaa aactgaccat cgttgctgta aatgttgaca    4020
gaaaatcatg gctgttcata ggtttcctgt tcatagcacg cctatcaaat catacattat    4080
tgtagggtac atgttcattt tgctttgttt tatcatatca agagtgatca gttatgaaga    4140
gatcttttga gtttgtgcct atccgtgtgg ctttgtatgc ttatgttctg acttttggtc    4200
ttggttcatg gtgagatact tttgtttgcc atgagcatct tgatagagca atatgaacac    4260
aatatattag aacctctgca acctgttatc aacttctgac tcaaactctg tttaccagtt    4320
ttaatggatg atcataagga agctgaggca atagaagagc tttcaagagc cattgatttt    4380
aagccagatc tgcaactatt acatcttcga gcggcatttt atgattcaat gggtgatttt    4440
gtctctgcag tccgggactg tgaagcagcc ctttgtcttg atcctaatca taatgagatt    4500
cttgatctct gtaataaagc acgggagcat attcgagaac caaagtga              4548
```

<210> SEQ ID NO 10
<211> LENGTH: 954
<212> TYPE: PRT
<213> ORGANISM: Glycine max

<400> SEQUENCE: 10

```
Met Gln His Ser Ile Phe Ala Ser Met Arg Ser Leu Lys Ile Met Asp
1               5                   10                  15

Gly Cys Lys Gly Thr Gln Val Tyr Ala Ile Asn Pro Ser Ser Ala Thr
            20                  25                  30

Gly Gly Gly Ile Gly Glu Lys Leu Leu Gln Gln Leu His Asp His Ile
        35                  40                  45

Lys Ser His Thr Leu Arg Thr Lys Ser Val Arg Asn Leu Gln Pro Pro
    50                  55                  60

Asn Met Thr Thr Pro Ser Glu Val Phe Val Ser Asp Gly Ser Leu Leu
65                  70                  75                  80

Pro Tyr Gly Leu Pro Met Thr Asp Leu Leu Glu Pro Lys Ile Glu Pro
                85                  90                  95

Ser Leu Val Ser Val Asp Phe Val Glu Thr Leu Ala Gly Val Tyr Arg
            100                 105                 110

Arg Thr Glu Asp Arg His Gln Phe Asp Arg Ser Glu Val Tyr Leu Glu
        115                 120                 125

Gln Cys Ala Val Phe Gln Gly Leu Ala Asp Pro Lys Leu Phe Arg Arg
    130                 135                 140
```

```
Ser Leu Arg Ala Ala Arg Gln His Ala Ile Asn Val His Ala Lys Val
145                 150                 155                 160

Val Leu Ser Ala Trp Leu Arg Tyr Glu Arg Arg Glu Asp Glu Leu Ile
                165                 170                 175

Gly Ser Ser Leu Met Asp Cys Ser Gly Arg Asn Leu Glu Cys Pro Arg
            180                 185                 190

Thr Thr Leu Val Pro Gly Tyr Asp Pro Glu Leu Val Phe Asp Ser Cys
        195                 200                 205

Ala Cys Thr Gly Ala Arg Ala Gly Asn Gly Asp Asn Asp Asn Asp Asp
    210                 215                 220

Ala Met Ala Ile Val Val Asp Glu Gln Cys Ser Thr Ser Glu Glu Glu
225                 230                 235                 240

Glu Glu Asp Gly Asp Met Ser Phe Cys Val Gly Asp Asp Glu Ile Lys
            245                 250                 255

Cys Asn Arg Phe Asn Ile Ala Ser Leu Ser Arg Pro Phe Lys Ile Met
            260                 265                 270

Leu Tyr Gly Gly Phe Ile Glu Ser Thr Arg Glu Lys Ile Asn Phe Ser
        275                 280                 285

Arg Asn Cys Phe Ser Val Glu Ala Leu Arg Ala Ala Glu Val Phe Ser
    290                 295                 300

Arg Arg Lys Arg Leu Ser His Leu Glu Pro Lys Val Ile Leu Glu Leu
305                 310                 315                 320

Leu Ser Leu Ala Asn Arg Phe Cys Cys Glu Met Lys Asn Ala Cys
            325                 330                 335

Asp Ala His Leu Ala Ser Leu Val Cys Asp Ile Asp Asp Ala Leu Leu
        340                 345                 350

Leu Val Glu Tyr Gly Leu Glu Glu Thr Ala Tyr Leu Leu Val Ala Ala
        355                 360                 365

Cys Leu Gln Val Phe Leu Arg Glu Leu Pro Gly Ser Met Gln Ser Leu
    370                 375                 380

Ser Val Val Lys Ile Phe Cys Ser Pro Glu Gly Arg Asp Arg Leu Ala
385                 390                 395                 400

Leu Ala Gly His Ala Ser Phe Val Leu Tyr Tyr Phe Leu Ser Gln Ile
            405                 410                 415

Ala Met Glu Glu Glu Met Arg Ser Asn Thr Thr Val Met Leu Leu Glu
            420                 425                 430

Arg Leu Val Glu Cys Ala Lys Asp Gly Trp Glu Lys Gln Val Ala Phe
        435                 440                 445

His Leu Leu Gly Val Val Met Leu Glu Arg Lys Glu Tyr Lys Asp Ala
450                 455                 460

Gln Tyr Trp Phe Gln Ala Ala Val Asp Ala Gly His Ala Tyr Ser Leu
465                 470                 475                 480

Val Gly Val Ala Arg Ala Lys Tyr Lys Arg Gly His Thr Tyr Ser Ala
            485                 490                 495

Tyr Lys Leu Met Asn Ser Leu Ile Ser Asp His Lys Pro Val Gly Trp
        500                 505                 510

Met Tyr Gln Glu Arg Ser Leu Tyr Cys Val Gly Lys Glu Lys Leu Met
        515                 520                 525

Asp Leu Met Ser Ala Thr Glu Leu Asp Pro Thr Leu Ser Phe Pro Tyr
530                 535                 540

Lys Phe Arg Ala Val Ser Phe Leu Glu Glu Asn Lys Ile Gly Pro Ala
545                 550                 555                 560

Ile Ala Glu Ile Asn Lys Ile Ile Gly Phe Lys Val Ser Pro Asp Cys
```

```
                565                 570                 575
Leu Glu Leu Arg Ala Trp Phe Leu Ile Ala Met Glu Asp Tyr Glu Gly
            580                 585                 590

Ala Leu Arg Asp Val Arg Ala Ile Leu Thr Leu Asp Pro Asn Tyr Met
            595                 600                 605

Met Phe Tyr Gly His Met His Gly Asp Gln Leu Val Glu Leu Leu Gln
610                 615                 620

Pro Phe Val Gln Gln Trp Ser Gln Ala Asp Cys Trp Ile Gln Leu Tyr
625                 630                 635                 640

Asp Arg Trp Ser Ser Val Asp Asp Ile Gly Ser Leu Ala Val Val His
                645                 650                 655

Gln Met Leu Ala Lys Asp Pro Gly Lys Ser Leu Leu Cys Phe Arg Gln
            660                 665                 670

Ser Leu Leu Leu Arg Leu Asn Cys Pro Lys Ser Ala Met Arg Ser
            675                 680                 685

Leu Arg Leu Ala Arg Asn His Ser Thr Ser Asp His Glu Arg Leu Val
            690                 695                 700

Tyr Glu Gly Trp Ile Leu Tyr Asp Thr Gly Tyr Arg Glu Glu Ala Leu
705                 710                 715                 720

Ala Lys Ala Glu Glu Ser Ile Ser Ile Arg Arg Ser Phe Glu Ala Tyr
                725                 730                 735

Phe Leu Lys Ala Tyr Ala Leu Ala Asp Ser Asn Leu Asp Ser Glu Ser
            740                 745                 750

Ser Lys Tyr Val Ile Cys Leu Leu Glu Glu Ala Leu Arg Cys Pro Leu
            755                 760                 765

Asp Gly Leu Arg Lys Gly Gln Ala Leu Asn Asn Leu Gly Ser Val Tyr
            770                 775                 780

Val Asp Cys Asp Lys Leu Asp Leu Ala Ala Asp Cys Tyr Met Asn Ala
785                 790                 795                 800

Leu Asn Ile Lys His Thr Arg Ala His Gln Gly Leu Ala Arg Val Tyr
                805                 810                 815

His Leu Lys Asn Leu Arg Lys Ala Ala Tyr Asp Glu Met Thr Lys Leu
            820                 825                 830

Ile Glu Lys Ala Arg Ser Asn Ala Ser Ala Tyr Glu Lys Arg Ser Glu
            835                 840                 845

Tyr Cys Asp Arg Asp Met Ala Lys Ser Asp Leu Ser Met Ala Ser Gln
850                 855                 860

Leu Asp Pro Leu Arg Thr Tyr Pro Tyr Arg Tyr Arg Ala Ala Val Leu
865                 870                 875                 880

Met Asp Asp His Lys Glu Ala Glu Ala Ile Glu Glu Leu Ser Arg Ala
                885                 890                 895

Ile Asp Phe Lys Pro Asp Leu Gln Leu Leu His Leu Arg Ala Ala Phe
            900                 905                 910

Tyr Asp Ser Met Gly Asp Phe Val Ser Ala Val Arg Asp Cys Glu Ala
            915                 920                 925

Ala Leu Cys Leu Asp Pro Asn His Asn Glu Ile Leu Asp Leu Cys Asn
            930                 935                 940

Lys Ala Arg Glu His Ile Arg Glu Pro Lys
945                 950

<210> SEQ ID NO 11
<211> LENGTH: 123
<212> TYPE: PRT
<213> ORGANISM: Artificial Sequence
```

<220> FEATURE:
<223> OTHER INFORMATION: Consensus Sequence of Conserved N-Terminal
      Domain
<220> FEATURE:
<221> NAME/KEY: UNSURE
<222> LOCATION: (1)..(123)
<223> OTHER INFORMATION: "Xaa" can be any amino acid

<400> SEQUENCE: 11

Phe Xaa Xaa Xaa Xaa Xaa Xaa Xaa Cys Xaa Arg Xaa Xaa Xaa Ala
1               5                   10                  15

Xaa Leu Ser Xaa Pro Xaa Xaa Xaa Xaa Leu Xaa Gly Xaa Phe Xaa Glu
            20                  25                  30

Xaa Xaa Xaa Xaa Xaa Xaa Xaa Xaa Xaa Xaa Xaa Xaa Xaa Xaa Xaa
        35                  40                  45

Xaa Met Xaa Xaa Xaa Xaa Xaa Xaa Ser Xaa Xaa Xaa Xaa Xaa Xaa
    50                  55                  60

Xaa Xaa Xaa Xaa Xaa Xaa Xaa Xaa Leu Xaa Xaa Ala Xaa Xaa Phe
65                  70                  75                  80

Cys Cys Xaa Xaa Leu Lys Xaa Xaa Cys Xaa Xaa Leu Xaa Xaa
            85                  90                  95

Xaa Xaa Xaa Xaa Xaa Ala Xaa Xaa Xaa Xaa Xaa Xaa Xaa Glu Xaa
            100                 105                 110

Xaa Xaa Xaa Xaa Leu Xaa Xaa Xaa Cys Leu Gln
        115                 120

<210> SEQ ID NO 12
<211> LENGTH: 240
<212> TYPE: PRT
<213> ORGANISM: Artificial Sequence
<220> FEATURE:
<223> OTHER INFORMATION: Consensus Sequence of Conserved C-Terminal
      Domain
<220> FEATURE:
<221> NAME/KEY: UNSURE
<222> LOCATION: (1)..(240)
<223> OTHER INFORMATION: "Xaa" can be any amino acid

<400> SEQUENCE: 12

Trp Ser Xaa Val Asp Asp Xaa Xaa Ser Leu Xaa Val Xaa Xaa Xaa Met
1               5                   10                  15

Leu Xaa Xaa Xaa Xaa Xaa Xaa Xaa Xaa Leu Xaa Phe Arg Gln Ser Leu
            20                  25                  30

Leu Leu Leu Arg Leu Asn Cys Xaa Xaa Xaa Ala Met Arg Xaa Leu Xaa
        35                  40                  45

Xaa Ala Xaa Xaa Xaa Xaa Xaa Xaa Xaa Glu Arg Leu Val Tyr Glu
    50                  55                  60

Gly Trp Xaa Leu Tyr Asp Xaa Gly Xaa Xaa Xaa Glu Xaa Leu Xaa Lys
65                  70                  75                  80

Ala Xaa Xaa Xaa Ile Xaa Xaa Xaa Arg Ser Phe Glu Ala Xaa Phe Leu
            85                  90                  95

Xaa Ala Tyr Xaa Leu Xaa Xaa Xaa Xaa Xaa Asp Xaa Xaa Xaa Xaa
            100                 105                 110

Xaa Val Xaa Xaa Xaa Leu Xaa Xaa Ala Xaa Xaa Cys Xaa Xaa Asp Xaa
        115                 120                 125

Leu Arg Lys Gly Gln Ala Xaa Asn Asn Xaa Gly Xaa Xaa Tyr Xaa Xaa
        130                 135                 140

Xaa Xaa Xaa Leu Asp Xaa Ala Xaa Xaa Xaa Tyr Xaa Xaa Ala Xaa Xaa
            145                 150                 155                 160

```
Xaa Xaa His Xaa Arg Ala Xaa Gln Gly Leu Ala Arg Val Xaa Xaa Leu
            165                 170                 175

Xaa Asn Xaa Xaa Xaa Xaa Ala Xaa Xaa Glu Met Thr Xaa Leu Xaa Glu
        180                 185                 190

Xaa Xaa Xaa Xaa Xaa Ala Xaa Ala Tyr Glu Lys Arg Ser Glu Tyr Xaa
    195                 200                 205

Xaa Arg Xaa Xaa Xaa Xaa Asp Leu Xaa Xaa Xaa Xaa Xaa Leu Asp
    210                 215                 220

Pro Xaa Arg Xaa Tyr Pro Tyr Arg Tyr Arg Ala Ala Val Leu Met Asp
225                 230                 235                 240

<210> SEQ ID NO 13
<211> LENGTH: 36
<212> TYPE: DNA
<213> ORGANISM: Artificial Sequence
<220> FEATURE:
<223> OTHER INFORMATION: probe

<400> SEQUENCE: 13
tcgacccacg cgtccgaaaa aaaaaaaaaa aaaaaa                              36
```